United States Patent
Wrana

(10) Patent No.: US 7,105,636 B1
(45) Date of Patent: Sep. 12, 2006

(54) SARA PROTEINS

(75) Inventor: Jeffrey L. Wrana, Toronto (CA)

(73) Assignee: HSC Research and Development Limited Partnership, Toronto (CA)

( * ) Notice: Subject to any disclaimer, the term of this patent is extended or adjusted under 35 U.S.C. 154(b) by 0 days.

(21) Appl. No.: 09/744,167

(22) PCT Filed: Jul. 20, 1999

(86) PCT No.: PCT/CA99/00656

§ 371 (c)(1),
(2), (4) Date: Sep. 20, 2001

(87) PCT Pub. No.: WO00/05360

PCT Pub. Date: Feb. 3, 2000

(30) Foreign Application Priority Data

Jul. 20, 1998 (CA) ............................................. 2237701
Dec. 10, 1998 (CA) ............................................ 2253647

(51) Int. Cl.
*A61K 38/16* (2006.01)
*C07H 21/02* (2006.01)

(52) U.S. Cl. ..................... 530/350; 536/23.1; 536/23.6; 935/60

(58) Field of Classification Search ................ 536/23.1, 536/23.6; 935/60; 530/350
See application file for complete search history.

(56) References Cited

OTHER PUBLICATIONS

Tsukazaki et al., "SARA, a FYVE Domain Protein that Recruits Smad2 to the TGF_beta Receptor," Cell, 1998, vol. 95, pp. 779–791.*

Abdollah, S., Macías–Silva, M., Tsukazaki, T., Hayashi, H., Attisano, L., and Wrana, J.L. (1997). TβRI phosphorylation of Smad2 on Ser 465 and 467 is required for Smad2/Smad4 complex formation and signaling. J. Biol. Chem. 272, 27678–27685.

Attisano, L. and Wrana, J.L. (1998). Mads and Smads in TGFβ signaling. Curr. Op. Cell Biol. 10, 188–194.

B. Meckelein et al., (1998), Mol. Brain Research, v. 55, pp. 181–197.

Burd et al., (1998), Mol. Cell., 2, 157–162.

Chen, Y., Bhushan, A., and Vale, W. (1997b). Smad8 mediates the signaling of the receptor serine kinase. Proc. Natl. Acad. Sci. USA 94, 12938–12943.

Chen, Y., Lebrun, J.–J., and Vale, W. (1996). Regulation of transforming growth factor β– and activin–induced transcription by mammalian Mad proteins, Proc. Natl. Acad. Sci. USA 93, 12992–12997.

Dennler, S., Itoh, S., Vivien, D., ten Dijke, P., Huet, S., and Gauthier, J.–M. (1998). Direct binding of Smad3 and Smad4 to critical TGFβ–inducible elements in the promoter of human plasminogen activator inhibitor–type 1 gene. EMBO J. 17, 3091–3100.

Dyson, S. and Gurdon, J.B. (1998). The Intepretation of Position in a Morphogen Gradient as Revealed by Occupancy of Activin Receptors. Cell 93, 557–568.

E. Labbé et al., (1998), Molecular Cell, v. 2, pp. 109–120.
EMBL Sequence Database Accession No. EMHUM2.AB002303, KIAA0305.

(Continued)

*Primary Examiner*—Michael Borin
(74) *Attorney, Agent, or Firm*—Myers, Bigel, Sibley & Sajovec, P.A.

(57) ABSTRACT

A new family of proteins, the SARA proteins, has been identified. These proteins bind to receptor-regulated Smad proteins and modulate signal transduction by TGFβ, activin and bone morphogenetic protein.

9 Claims, 20 Drawing Sheets

OTHER PUBLICATIONS

EMBL Sequence Database, Accession No. EMHUM1:AF130419.

Faux, M. and Scott, J.D. (1996). Molecular glue: kinase anchoring and scaffold proteins. Cell 85, 9–12.

Gaullier et al., (1998), Nature, 394, 432–433.

Heldin, C.–H., Miyazono, K., and ten Dijke, P. (1997). TGF-□ signaling from cell membrane to nucleus through SMAD proteins. Nature. 390, 465–471.

Henis, Y.I., Moustakas, A., Lin, H.Y., and Lodish, H.F. (1994). The type II and III transforming growth factor–β receptors form homo–oligomers. J. Cell Biol. 126, 139–154.

Hoodless, P.A., Haerry, T., Abdollah, S., Stapleton, M., O'Connor, M.B., Attisano, L., and Wrana, J.L. (1996). MADR1, and MAD–related protein that functions in BMP2 signaling pathways. Cell 85, 489–500.

Kim, J., Johnson, K., Chen, H.J., Carroll, S., and Laughon, A. (1997). Drosophila Mad binds to DNA and directly mediates activation of *vestigial* by decapentaplegic. Nature 388, 304–308.

Kretzschmar, M. and Massagué, J. (1998). SMADs: mediators and regulators of TGF-□ signaling. Current Opinion in Genetics & Development 8, 103–111.

Kretzschmar, M., Liu, F., Hata, A., Doody, J., and Massagué, J. (1997). The TGF–β family mediator Smad1 is phosphorylated directly and activated functionally by the BMP receptor kinase. Genes Dev. 11, 984–995.

Labbé, E., Silvestri, C., Hoodless, P.A., Wrana, J.L., and Attisano, L. (1998). Smad2 and Smad3 positively and negatively regulate TGF□–dependent transcription through the forkhead DNA binding protein, FAST2. Molecular Cell in press.

Lagna, G., Hata, A., Hemmati–Brivanlou, A., and Massagué, J. (1996), Partnership between DPC4 and SMAD proteins in TGF–β signaling pathways. Nature 383, 832–836.

Liu, X., Sun, Y., Constantinescu, S.N., Karam, E., Weinberg, R.A., and Lodish, H.F. (1997b). Transforming growth factor □–induced phosphorylation of Smad3 is required for growth inhibition and transcriptional induction in epithelial cells. Proc. Natl. Acad. Sci. USA 94, 10669–10764.

M. Kretzschmar et al., (1998), Current Opinion in Genetics & Development, v. 8, pp. 103–111.

Macías–Silva, M., Abdollah, S., Hoodless, P.A., Pirone, R., Attisano, L., and Wrana, J.L. (1996). MADR2 is a substrate of the TGFβ receptor and its phosphorylation is required for nuclear accumulation and signaling. Cell 87, 1215–1224.

Nagase et al., (1997), DNA Research, v. 4, pp. 141–150.

Nakao, A., Imamura, T., Souchelnytskyi, S., Kawabata, M., Ishisaki, A., Oeda, E., Tamaki, K., Hanai, J.–i., Heldin, C.–H., Miyazono, K., and ten Dijke, P. (1997a). TGF–β receptor–mediated signaling through Smad2, Smad3 and Smad4. EMBO J. 16, 5353–5362.

Nakayama, T., Snyder, M.A., Grewal, S.S., Tsuneizumi, K., Tabata, T., and Christian, J.L. (1998). Xenopus Smad8 acts downstream of BMP–4 to modulate its activity during vertebrate embryonic patterning. Development 125, 857–867.

Nishimura, R., Kato, Y., Chen, D., Harris, S.E., Mundy, G.R., and Yoneda, T. (1998). Smad5 and DPC4 are key molecules in mediating BMP–2–induced osteoblastic differentiation of the pluripotent mesenchymal precursor cell line C2C12. J. Biol. Chem. 273, 1872–1879.

Patki et al., (1998), Nature, 394, 433–434.

Patterson, G., Koweek, A., Wong, A., Liu, Y., and Ruvkun, G. (1997). The DAF–3 Smad protein antagonizes TGF–β–related receptor signaling in the C. elegans dauer pathway. Genes and Dev.

Pawson, T. and Scott, J.D. (1997). Signaling through scaffold, anchoring and adaptor proteins. Science 278, 2075–2080.

Reddy, A.H. (1998), *Nature Biotechnology*, v. 16, pp. 247–252.

Savage, C., Das, P., Finelli, A., Townsend, S., Sun, C., Baird, S., and Padgett, R.(1996). The *C. elegans sma–2, sma–3* and *sma–4* genes define a novel conserved family of TGF–β pathway components. Proc. Natl. Acad. Sci. USA 93, 790–794.

Sekelsky, J.J., Newfeld, S.J., Raftery, L.A., Chartoff, E.H., and Gelbart, W.M. (1995). Genetic characterization and cloning of Mothers against dpp, a gene required for decapentaplegic function in Drosophila melanogaster. Genetics 139, 1347–1358.

Simonsen et al., (1998), Nature, 394, 494–495.

Souchelnytskyi, S., Tamaki, K., Engström, U., Wernstedt, C., ten Dijke, P., and Heldin, C.–H. (1997). Phosphorylation of $Ser^{465}$ and $Ser^{467}$ in the C Terminus of Smad2 Mediates Interaction with Smad4 and Is Required for Transforming Growth Factor–□ Signaling. J. Biol. Chem. 272, 28107–28115.

Stenmark et al., (1996), J. Biol. Chem., v. 271, pp. 24048–24054.

Tsukazaki, T., Chiang, T.A., Davison, A.F., Attisano, L., and Wrana, J.L. (1998).SARA, a FYVE domain protein that recruits Smad2 to the TGFβ receptor. Cell,95, 779–791.

Wiedemann et al., (1998), Nature, 394, 426–427.

Yingling, J.M., Datto, M.B., Wong, C., Frederick, J.P., Liberati, N.T., and Wang, X.–F. (1997). Tumour Suppressor Smad4 is a Transforming Growth Gactor □–Inducible DNA Binding Protein. Mol. Cell. Biol. 17, 7019–7028.

Zawel, L., Dai, J.L., Buckhaults, P., Zhou, S., Kinzler, K.W., Vogelstein, B., and Kern, S.E. (1998). Human Smad3 and Smad4 are sequence–specific transcription activators. Mol. Cell 1, 611–617.

Zhang, Y., Musci, T., and Derynck, R. (1997). The tumor suppressor SMAd4/DPC4 as a central mediator of Smad function. Curr. Biol. 7, 270–276.

* cited by examiner

SEQUENCE LISTING

<160> NUMBER OF SEQ ID NOS: 8

<210> SEQ ID NO 1
<211> LENGTH: 4839
<212> TYPE: DNA
<213> ORGANISM: Homo sapiens

<400> SEQUENCE: 1

```
gcatactgaa tcagcaggac tggctggtgg tgcagcagac atcatgagta agcaccgaga      60
agtctgttcc ttatcacgtg tgtaagggga aaaggtttta aacaagtctc ttaagtggtg     120
tttcctcacc gatggagaat acttccaag cagaagctta caacctggga caaggtgtta     180
gatgaatttg aacaaaacga agatgaaaca gtttcttcta ctttattgga tacaaagtgg     240
aataagattc tagatccccc ttctcaccgg ctgtcattta accctacttt ggccagtgtg     300
aatgaatctg cagtttctaa tgagtcacaa ccacaactga aagtcttctc cctggctcat     360
tcagctcccc tgaccacaga ggaagaggat cactgtgcta atggacagga ctgtaatcta     420
aatccagaga ttgccacaat gtggattgat gaaaatgctg ttgcagaaga ccagttaatt     480
aagagaaact atagttggga tgatcaatgc agtgctgttg aagtgggaga agaaaatgt      540
ggaaacctgg cttgtctgcc agatgagaag aatgttcttg ttgtagccgt catgcataac     600
tgtgataaaa ggacattaca aaacgattta caggattgta ataattataa tagtcaatcc     660
cttatggatg cttttagctg ttcactggat aatgaaaaca gacaaactga tcaatttagt     720
tttagtataa atgagtccac tgaaaaagat atgaattcag agaaacaaat ggatccattg     780
aatagaccga aaacagaggg gagatctgtt aaccatctgt gtcctacttc atctgatagt     840
ctagccagtg tctgttcccc ttcacaatta aaggatgacg gaagtatagg tagagacccc     900
tccatgtctg cgattacaag tttaacggtt gattcagtaa tctcatccca gggaacagat     960
ggatgtcctg ctgttaaaaa gcaagagaac tatataccag atgaggacct cactggcaaa    1020
atcagctctc ctaggacaga tctagggagt ccaaattcct tttcccacat gagtgagggg    1080
attttgatga aaaagagcc agcagaggag agcaccactg aagaatccct ccggtctggt    1140
ttacctttgc ttctcaaacc agacatgcct aatgggtctg gaaggaataa tgactgtgaa    1200
cggtgttcag attgccttgt gcctaatgaa gttagggctg atgaaaatga aggttatgaa    1260
catgaagaaa ctcttggcac tacagaattc cttaatatga cagagcattt ctctgaatct    1320
caggacatga ctaattggaa gttgactaaa ctaaatgaga tgaatgatag ccaagtaaac    1380
gaagaaaagg aaaagtttct acagattagt cagcctgagg cactaatgg tgatagtgga    1440
ggacagtgtg ttggattggc agatgcaggt ctagatttaa aaggaacttg cattagtgaa    1500
agtgaagaat gtgatttctc cactgttata gacacaccag cagcaaatta tctatctaat    1560
ggttgtgatt cctatggaat gcaagaccca ggtgtttctt ttgttccaaa gactttaccc    1620
tccaaagaag attcagtaac agaagaaaaa gaaatagagg aaagcaagtc agaatgctac    1680
tcaaatattt atgaacagag aggaaatgag gccacagaag ggagtggact acttttaaac    1740
agcactggtg acctaatgaa gaaaaattat ttacataatt tctgtagtca agttccatca    1800
gtgcttgggc aatcttcccc caaggtagta gcaagcctgc catctatcag tgttcctttt    1860
ggtggtgcaa gacccaagca accttctaat cttaaacttc aaattccaaa gccattatca    1920
gaccatttac aaaatgactt tcctgcaaac agtggaaata atactaaaaa taaaaatgat    1980
attcttggga aagcaaaatt agggaaaaac tcagcaacca atgtatgcag tccatctttg    2040
```

-continued

```
ggaaacatct ctaatgtcga tacaaatggg gaacatttag aaagttatga ggctgagatc    2100
tccactagac catgccttgc attagctcca gatagcccag ataatgatct cagagctggt    2160
cagtttggaa tttctgccag aaagccattc accacgctgg gtgaggtggc tccagtatgg    2220
gtaccggatt ctcaggctcc aaattgcatg aaatgtgaag ccaggtttac attcaccaaa    2280
aggaggcatc actgcagagc atgtgggaag gttttctgtg cttcctgctg tagcctgaaa    2340
tgtaaactgt tatacatgga cagaaaggaa gctagagtgt gtgtaatctg ccattcagtg    2400
ctaatgaatg ctcaagcctg ggagaacatg atgagtgcct caagccagag ccctaaccct    2460
aacaatcctg ctgaatactg ttctactatc cctcccttgc agcaagctca ggcctcagga    2520
gctctgagct ctccacctcc cactgtgatg gtacctgtgg gagttttaaa gcaccctgga    2580
gcagaagtgg ctcagcccag agagcagagg cgagtttggt ttgctgatgg gatcttgccc    2640
aatggagaag ttgctgatgc agccaaatta acaatgaatg gaacttcctc tgcaggaacc    2700
ctggctgtgt cacacgaccc agtcaagcca gtaactacca gtcctctacc agcagagacg    2760
gatatttgtc tattctctgg gagtataact caggttggaa gtcctgttgg aagtgcaatg    2820
aatcttattc ctgaagatgg ccttcctccc attctcatct ccactggtgt aaaaggagac    2880
tatgctgtgg aagagaaacc atcacagatt tcagtaatgc agcagttgga ggatggtggc    2940
cctgacccac ttgtatttgt tttaaatgca aatttgttgt caatggttaa aattgtaaat    3000
tatgtgaaca ggaagtgctg gtgtttcaca accaagggaa tgcatgcagt gggtcagtct    3060
gagatagtca ttcttctaca gtgtttaccg gatgaaaagt gtttgccaaa ggatatcttt    3120
aatcactttg tgcagcttta tcgggatgct ctggcaggga atgtggtgag caacttggga    3180
cattccttct tcagtcaaag tttccttggc agtaaagaac atggtggatt cttatatgtg    3240
acatctacct accagtcact gcaagaccta gtactcccaa ccccaccttla cttgtttggg    3300 attcttatcc agaaatggga aactccttgg gctaaagtat ttcctatccg tctgatgttg    3360
agacttggag ctgaatatcg actttatcca tgcccactat tcagtgtcag atttcggaag    3420
ccattgtttg gagagacggg gcataccatc atgaatcttc ttgcagactt cagaaattac    3480
cagtatacct tgccagtagt tcaaggtttg gtggttgata tggaagttcg gaaaactagc    3540
atcaaaattc ccagcaacag atacaatgag atgatgaaag ccatgaacaa gtccaatgag    3600
catgtcctgg caggaggtgc ctgcttcaat gaaaaggcag actctcatct tgtgtgtgta    3660
cagaatgatg atgaaacta tcagacccag gctatcagta ttcacaatca gcccagaaaa    3720
gtgactggtg ccagtttctt tgtgttcagt ggcgctctga atcctcttc tggataccttt   3780 gccaagtcca gtattgtgga agatggtgtt atggtccaga ttactgcaga gaacatggat    3840
tccttgaggc aggcactgcg agagatgaag gacttcacca tcacctgtgg gaaggcggac    3900
gcggaggaac cccaggagca catccacatc cagtgggtgg atgatgacaa gaacgttagc    3960
aagggtgtcg taagtcctat agatgggaag tccatggaga ctataacaaa tgtgaagata    4020
ttccatggat cagaatataa agcaaatgga aaagtaatca gatggacaga ggtgttttc     4080 ctagaaaacg atgaccagca caattgcctc agtgatcctg cagatcacag tagattgact    4140
gagcatgttg ccaaagcttt ttgccttgct ctctgtcctc acctgaaact tctgaaggaa    4200
gatggaatga ccaaactggg actacgtgtg acacttgact cagatcaggt tggctatcaa    4260
gcagggagca atggccagcc ccttccctcg cagtacatga atgatctgga tagcgccttg    4320
gtgccggtga tccatggagg ggcctgccag cttagtgagg gccccgttgt catggaactc    4380
```

```
atctttata ttctggaaaa catcgtataa acagagaaga cttcatttt ttctgttcag    4440 acttgttgca acagcagtca tacccaaatc atttgcactt taaaactgga agattaagct    4500
tttgttaaca ctattaatgg ggtggggaat agggtgggag tgggggtttg ggagacgggt    4560
gggaaagggt ggttgggggg accgatgttc cataattcta agtcttctat gcattgtcca    4620
ccaagaagat ctgggcagct tctgttcctg cacaacagtt atgctatcct tgcagctaat    4680 cccttctgt tactgtttag acaagaattc cgctcctctc tcaagattta cttatggtca    4740
tgtgctcaga aatgctcaaa tgggtacaac catcaccaag ggtgggatgg gagggcagag    4800
gggaaataaa atataaagca tcaaaaaaaa aaaaaaaa                            4839
```

<210> SEQ ID NO 2
<211> LENGTH: 1323
<212> TYPE: PRT
<213> ORGANISM: Homo sapiens

<400> SEQUENCE: 2

```
Met Trp Ile Asp Glu Asn Ala Val Ala Glu Asp Gln Leu Ile Lys Arg
  1               5                  10                  15

Asn Tyr Ser Trp Asp Asp Gln Cys Ser Ala Val Glu Val Gly Glu Lys
             20                  25                  30

Lys Cys Gly Asn Leu Ala Cys Leu Pro Asp Glu Lys Asn Val Leu Val
         35                  40                  45

Val Ala Val Met His Asn Cys Asp Lys Arg Thr Leu Gln Asn Asp Leu
     50                  55                  60

Gln Asp Cys Asn Asn Tyr Asn Ser Gln Ser Leu Met Asp Ala Phe Ser
 65                  70                  75                  80

Cys Ser Leu Asp Asn Glu Asn Arg Gln Thr Asp Gln Phe Ser Phe Ser
                 85                  90                  95

Ile Asn Glu Ser Thr Glu Lys Asp Met Asn Ser Glu Lys Gln Met Asp
            100                 105                 110

Pro Leu Asn Arg Pro Lys Thr Glu Gly Arg Ser Val Asn His Leu Cys
        115                 120                 125

Pro Thr Ser Ser Asp Ser Leu Ala Ser Val Cys Ser Pro Ser Gln Leu
    130                 135                 140

Lys Asp Asp Gly Ser Ile Gly Arg Asp Pro Ser Met Ser Ala Ile Thr
145                 150                 155                 160

Ser Leu Thr Val Asp Ser Val Ile Ser Ser Gln Gly Thr Asp Gly Cys
                165                 170                 175

Pro Ala Val Lys Lys Gln Glu Asn Tyr Ile Pro Asp Glu Asp Leu Thr
            180                 185                 190

Gly Lys Ile Ser Ser Pro Arg Thr Asp Leu Gly Ser Pro Asn Ser Phe
        195                 200                 205

Ser His Met Ser Glu Gly Ile Leu Met Lys Lys Glu Pro Ala Glu Glu
    210                 215                 220

Ser Thr Thr Glu Glu Ser Leu Arg Ser Gly Leu Pro Leu Leu Leu Lys
225                 230                 235                 240

Pro Asp Met Pro Asn Gly Ser Gly Arg Asn Asn Asp Cys Glu Arg Cys
                245                 250                 255

Ser Asp Cys Leu Val Pro Asn Glu Val Arg Ala Asp Glu Asn Glu Gly
            260                 265                 270

Tyr Glu His Glu Glu Thr Leu Gly Thr Thr Glu Phe Leu Asn Met Thr
        275                 280                 285

Glu His Phe Ser Glu Ser Gln Asp Met Thr Asn Trp Lys Leu Thr Lys
```

-continued

```
            290                 295                 300
Leu Asn Glu Met Asn Asp Ser Gln Val Asn Glu Lys Glu Lys Phe
305                 310                 315                 320
Leu Gln Ile Ser Gln Pro Glu Asp Thr Asn Gly Asp Ser Gly Gln
                325                 330                 335
Cys Val Gly Leu Ala Asp Ala Gly Leu Asp Leu Lys Gly Thr Cys Ile
                340                 345                 350
Ser Glu Ser Glu Glu Cys Asp Phe Ser Thr Val Ile Asp Thr Pro Ala
                355                 360                 365
Ala Asn Tyr Leu Ser Asn Gly Cys Asp Ser Tyr Gly Met Gln Asp Pro
370                 375                 380
Gly Val Ser Phe Val Pro Lys Thr Leu Pro Ser Lys Glu Asp Ser Val
385                 390                 395                 400
Thr Glu Glu Lys Glu Ile Glu Glu Ser Lys Ser Glu Cys Tyr Ser Asn
                405                 410                 415
Ile Tyr Glu Gln Arg Gly Asn Glu Ala Thr Glu Gly Ser Gly Leu Leu
                420                 425                 430
Leu Asn Ser Thr Gly Asp Leu Met Lys Lys Asn Tyr Leu His Asn Phe
                435                 440                 445
Cys Ser Gln Val Pro Ser Val Leu Gly Gln Ser Ser Pro Lys Val Val
    450                 455                 460
Ala Ser Leu Pro Ser Ile Ser Val Pro Phe Gly Gly Ala Arg Pro Lys
465                 470                 475                 480
Gln Pro Ser Asn Leu Lys Leu Gln Ile Pro Lys Pro Leu Ser Asp His
                485                 490                 495
Leu Gln Asn Asp Phe Pro Ala Asn Ser Gly Asn Asn Thr Lys Asn Lys
                500                 505                 510
Asn Asp Ile Leu Gly Lys Ala Lys Leu Gly Glu Asn Ser Ala Thr Asn
                515                 520                 525
Val Cys Ser Pro Ser Leu Gly Asn Ile Ser Asn Val Asp Thr Asn Gly
                530                 535                 540
Glu His Leu Glu Ser Tyr Glu Ala Glu Ile Ser Thr Arg Pro Cys Leu
545                 550                 555                 560
Ala Leu Ala Pro Asp Ser Pro Asp Asn Asp Leu Arg Ala Gly Gln Phe
                565                 570                 575
Gly Ile Ser Ala Arg Lys Pro Phe Thr Thr Leu Gly Glu Val Ala Pro
                580                 585                 590
Val Trp Val Pro Asp Ser Gln Ala Pro Asn Cys Met Lys Cys Glu Ala
                595                 600                 605
Arg Phe Thr Phe Thr Lys Arg Arg His His Cys Arg Ala Cys Gly Lys
610                 615                 620
Val Phe Cys Ala Ser Cys Cys Ser Leu Lys Cys Lys Leu Leu Tyr Met
625                 630                 635                 640
Asp Arg Lys Glu Ala Arg Val Cys Val Ile Cys His Ser Val Leu Met
                645                 650                 655
Asn Ala Gln Ala Trp Glu Asn Met Met Ser Ala Ser Ser Gln Ser Pro
                660                 665                 670
Asn Pro Asn Asn Pro Ala Glu Tyr Cys Ser Thr Ile Pro Pro Leu Gln
                675                 680                 685
Gln Ala Gln Ala Ser Gly Ala Leu Ser Ser Pro Pro Thr Val Met
                690                 695                 700
Val Pro Val Gly Val Leu Lys His Pro Gly Ala Glu Val Ala Gln Pro
705                 710                 715                 720
```

```
Arg Glu Gln Arg Arg Val Trp Phe Ala Asp Gly Ile Leu Pro Asn Gly
            725                 730                 735

Glu Val Ala Asp Ala Ala Lys Leu Thr Met Asn Gly Thr Ser Ser Ala
        740                 745                 750

Gly Thr Leu Ala Val Ser His Asp Pro Val Lys Pro Val Thr Thr Ser
            755                 760                 765

Pro Leu Pro Ala Glu Thr Asp Ile Cys Leu Phe Ser Gly Ser Ile Thr
    770                 775                 780

Gln Val Gly Ser Pro Val Gly Ser Ala Met Asn Leu Ile Pro Glu Asp
785                 790                 795                 800

Gly Leu Pro Pro Ile Leu Ile Ser Thr Gly Val Lys Gly Asp Tyr Ala
                805                 810                 815

Val Glu Glu Lys Pro Ser Gln Ile Ser Val Met Gln Gln Leu Glu Asp
            820                 825                 830

Gly Gly Pro Asp Pro Leu Val Phe Val Leu Asn Ala Asn Leu Leu Ser
        835                 840                 845

Met Val Lys Ile Val Asn Tyr Val Asn Arg Lys Cys Trp Cys Phe Thr
    850                 855                 860

Thr Lys Gly Met His Ala Val Gly Gln Ser Glu Ile Val Ile Leu Leu
865                 870                 875                 880

Gln Cys Leu Pro Asp Glu Lys Cys Leu Pro Lys Asp Ile Phe Asn His
                885                 890                 895

Phe Val Gln Leu Tyr Arg Asp Ala Leu Ala Gly Asn Val Val Ser Asn
            900                 905                 910

Leu Gly His Ser Phe Phe Ser Gln Ser Phe Leu Gly Ser Lys Glu His
        915                 920                 925

Gly Gly Phe Leu Tyr Val Thr Ser Thr Tyr Gln Ser Leu Gln Asp Leu
    930                 935                 940

Val Leu Pro Thr Pro Tyr Leu Phe Gly Ile Leu Ile Gln Lys Trp
945                 950                 955                 960

Glu Thr Pro Trp Ala Lys Val Phe Pro Ile Arg Leu Met Leu Arg Leu
                965                 970                 975

Gly Ala Glu Tyr Arg Leu Tyr Pro Cys Pro Leu Phe Ser Val Arg Phe
            980                 985                 990

Arg Lys Pro Leu Phe Gly Glu Thr Gly His Thr Ile Met Asn Leu Leu
        995                 1000                1005

Ala Asp Phe Arg Asn Tyr Gln Tyr Thr Leu Pro Val Val Gln Gly Leu
    1010                1015                1020

Val Val Asp Met Glu Val Arg Lys Thr Ser Ile Lys Ile Pro Ser Asn
1025                1030                1035                1040

Arg Tyr Asn Glu Met Met Lys Ala Met Asn Lys Ser Asn Glu His Val
                1045                1050                1055

Leu Ala Gly Gly Ala Cys Phe Asn Glu Lys Ala Asp Ser His Leu Val
            1060                1065                1070

Cys Val Gln Asn Asp Asp Gly Asn Tyr Gln Thr Gln Ala Ile Ser Ile
        1075                1080                1085

His Asn Gln Pro Arg Lys Val Thr Gly Ala Ser Phe Phe Val Phe Ser
    1090                1095                1100

Gly Ala Leu Lys Ser Ser Ser Gly Tyr Leu Ala Lys Ser Ser Ile Val
1105                1110                1115                1120

Glu Asp Gly Val Met Val Gln Ile Thr Ala Glu Asn Met Asp Ser Leu
                1125                1130                1135
```

-continued

```
Arg Gln Ala Leu Arg Glu Met Lys Asp Phe Thr Ile Thr Cys Gly Lys
        1140                1145                1150
Ala Asp Ala Glu Glu Pro Gln Glu His Ile His Ile Gln Trp Val Asp
    1155                1160                1165
Asp Asp Lys Asn Val Ser Lys Gly Val Val Ser Pro Ile Asp Gly Lys
    1170                1175                1180
Ser Met Glu Thr Ile Thr Asn Val Lys Ile Phe His Gly Ser Glu Tyr
1185                1190                1195                1200
Lys Ala Asn Gly Lys Val Ile Arg Trp Thr Glu Val Phe Phe Leu Glu
        1205                1210                1215
Asn Asp Asp Gln His Asn Cys Leu Ser Asp Pro Ala Asp His Ser Arg
        1220                1225                1230
Leu Thr Glu His Val Ala Lys Ala Phe Cys Leu Ala Leu Cys Thr Gln
        1235                1240                1245
Leu Lys Leu Leu Lys Gly Asp Gly Met Thr Lys Leu Gly Leu Arg Val
        1250                1255                1260
Thr Leu Asp Ser Asp Gln Val Gly Tyr Gln Ala Gly Ser Asn Gly Gln
1265                1270                1275                1280
His Leu Pro Ser Gln Tyr Met Asn Asp Phe Asp Ser Asp Leu Val Lys
        1285                1290                1295
Met Ile His Gly Gly Ala Cys Gln Leu Ser Glu Gly Pro Val Val Met
        1300                1305                1310
Glu Leu Ile Phe Tyr Ile Leu Glu Asn Ile Val
        1315                1320

<210> SEQ ID NO 3
<211> LENGTH: 6632
<212> TYPE: DNA
<213> ORGANISM: Homo sapiens

<400> SEQUENCE: 3
actcccggcc ggggtagctc ttcactcctc agcgcgacgt cgtgtcgagt tcccaaaaag     60
ctccgcaggg gctgtaggga ggtgatctca tccattaaca gctgtgtgtt gccagttccc    120
aaatctttat ctatctcaga cttctctcct gcattccaga ttcttatatt cagctgcctt    180
ttggatatct ctcccaggat gttctcaagg catacaagaa ttaaattctg aataagtctg    240
caggtaggat ggacagttat tttaaagcag ctgtcagtga cttggacaaa ctccttgatg    300
attttgaaca gaacccagat gaacaagatt atctcgcaga tgtacaaaat gcatatgatt    360
ctaaccactg ctcagtttct tcagagttgg cttcctcaca gcgaacttca ttgctcccaa    420
aagaccaaga gtgcgttaat agttgtgcct catcagaaac aagctatgga acaaatgaga    480
gttccctgaa tgaaaaaaca ctcaagggac ttacttctat acaaaatgaa aaaaatgtaa    540
caggacttga tcttctttct tctgtggatg tggtacttc agatgaaatc cagccgttat    600
atatgggacg atgtagtaaa cctatctgtg atctgataag tgacatgggt aacttagttc    660
atgcaaccaa tagtgaagaa gatattaaaa aattattgcc agatgatttt aagtctaatg    720
cagattcctt gattggattg gatttatctt cagtgtcaga tactccctgt gtttcttcaa    780
cagaccatga tagtgatact gtcagagaac aacagaatga tatcagttct gaattacaaa    840
atagagaaat cggaggaatc aaagaattgg gtataaaagt agatacaaca ctttcagatt    900
cctataatta cagtggaaca gaaaatttaa agataaaaa gatctttaat cagttagaat    960
caattgttga ttttaacatg tcatctgctt tgactcgaca aagttccaaa atgtttcatg   1020
ccaaagacaa gctacaacac aagagccagc catgtggatt actaaaagat gttggcttag   1080
```

-continued

```
taaaagagga agtagatgtg gcagtcataa ctgccgcaga atgtttaaaa gaagagggca    1140
agacaagtgc tttgacctgc agccttccga aaaatgaaga tttatgctta aatgattcaa    1200
attcaagaga tgaaaatttc aaattacctg acttttcctt tcaggaagat aagactgtta    1260
taaaacaatc tgcacaagaa gactcaaaaa gtttagacct taaggataat gatgtaatcc    1320
aagattcctc ttcagcttta catgtttcca gtaaagatgt gccgtcctca ttgtcctgtc    1380
ttcctgcgtc tgggtctatg tgtggatcat taattgaaag taaagcacgg ggtgattttt    1440
tacctcagca tgaacataaa gataatatac aagatgcagt gactatacat gaagaaatac    1500
agaacagtgt tgttctaggt ggggaaccat tcaaagagaa tgatcttttg aaacaggaaa    1560
aatgtaaaag catactcctt cagtcattaa ttgaagggat ggaagacaga aagatagatc    1620
ctgaccagac agtaatcaga gctgagtctt tggatggtgg tgacaccagt tctacagttg    1680
tagaatctca agagggcttt tctggcactc atgtcccaga gtcttctgat tgttgtgaag    1740
gttttattaa tacttttcca agcaatgata tggatgggca agacttagat tactttaata    1800
ttgatgaagg cgcaaaaagt ggcccactaa ttagtgatgc tgaacttgat gcctttctga    1860
cagaacagta tcttcagacc actaacataa agtcttttga agaaaatgta aatgactcta    1920
aatcgcaaat gaatcagata gatatgaaag gcttagatga tggaaacatc aataatatat    1980
atttcaatgc agaagcagga gctattgggg aaagtcatgg tattaatata atttgtgaaa    2040
cagttgataa acaaaataca atagaaaatg gcctttcttt aggagaaaaa agcactattc    2100
cagttcaaca agggttacct accagtaagt ctgagattac aaatcaatta tcagtctctg    2160
atattaacag tcaatctgtt ggaggggcca gacctaagca attgtttagc cttccatcaa    2220
gaacaaggag ttcaaaggac ctgaataagc cagatgttcc agatacaata gaaagtgaac    2280
ccagcacagc agataccgtt gttccaatca cttgtgctat agattctaca gctgatccac    2340
aggttagctt caactctaat tacattgata tagaaagtaa ttctgaaggt ggatctagtt    2400
tcgtaactgc aaatgaagat tctgtacctg aaaacacttg caaagaaggc ttggttttgg    2460
gccagaaaca gcctacttgg gttcctgatt cagaagctcc aaactgtatg aactgccaag    2520
tcaaatttac ttttaccaaa cggcgacacc attgccgagc atgtgggaaa gtattttgtg    2580
gtgtctgttg taataggaag tgtaaactgc aatatctaga aaaggaagca agagtatgtg    2640
tagtctgcta tgaaactatt agtaaagctc aggcatttga aaggatgatg agtccaactg    2700
gttctaatct taagtctaat cattctgatg aatgtactac tgtccagcct cctcaggaga    2760
accaaacatc cagtataacct tcaccagcaa ctttgccagt ctcagcactt aaacaaccag    2820
gtgttgaagg actatgttcc aaagaacaga gagagtatg gtttgcagat ggtatattgc    2880
ccaatggtga agttgcagat acaacaaaat tatcatctgg aagtaaaaga tgttctgaag    2940
actttagtcc tctctcacct gatgtgccta tgacagtaaa cacagtggat cattcccatt    3000
ctactacagt ggaaaagcca aacaatgaga caggagatat tacaagaaat gagataattc    3060
agagtcctat ttctcaggtt ccatcagtgg aaaaattgtc tatgaacaca ggaaatgagg    3120
ggttacctac ttctggttca tttacactag atgatgatgt ttttgcagaa actgaagaac    3180 catcagtcc tactggtgtc ttagttaaca gcaatttacc tattgctagt atttcagatt    3240
ataggttact gtgtgatatt aacaagtatg tctgcaataa gattagtctt ctacctaatg    3300
atgaggacag tttgccccca cttctggttg catctggaga aaagggatca gtgcctgtag    3360
tagaagaaca tccatctcat gagcagatca ttttgctct tgaaggtgaa ggctttcatc    3420
```

```
ctgttacatt tgtcctaaat gctaatctac tcgtgaatgt caaattcata ttttattcct    3480
cagacaaata ttggtacttt tcaaccaatg gattgcatgg cttgggacag gcagaaatta    3540
ttattctatt gttatgtttg ccaaatgaag atactattcc taaggacatc ttcagactat    3600
ttatcaccat atataaggat gctctaaaag gaaaatacat agaaacttg gacaatatta    3660 cctttactga gagttttctc agtagcaagg atcacggagg attcctgttt attacaccta    3720
cttttcagaa acttgatgat ctctcattac caagtaatcc ttttctttgt ggaattctta    3780
tccagaagct tgagattccc tgggcaaagg ttttttcctat gcgtttaatg ttgagattgg    3840
gtgcagaata taaagcatat cctgctcctc taacaagcat cagaggccga aaacctcttt    3900
ttggagaaat aggacacact attatgaact tacttgttga ccttcgaaat taccagtata    3960
ccttgcataa tatagatcaa ctgttgattc atatggaaat gggaaaaagc tgcataaaaa    4020
taccacggaa aaagtacagt gatgtaatga aagtactaaa ttcttccaat gagcatgtca    4080
ttagcattgg agcaagtttc agtacagaag cagattctca tctagtctgt atacagaatg    4140
atggaattta tgaaacacag gccaacagtg ccactggcca tcctagaaaa gtgacaggtg    4200
caagttttgt ggtattcaat ggagctctaa aaacatcttc aggatttctt gctaagtcca    4260
gcatagttga agatggctta atggtacaaa taactccaga gaccatgaat ggcttgcggc    4320
tagctttacg agaacagaaa gactttaaaa ttacatgtgg gaaagttgat gcagtagacc    4380
tgagagaata cgtggatatc tgctgggtag atgctgaaga aaaggaaac aaaggagtta    4440 tcagttcagt ggatggaata tcattacaag gatttccaag tgaaaaaata aaactggaag    4500
cagattttga aaccgatgag aagattgtaa aatgtaccga ggtgttctac tttctaaagg    4560
accaggattt atctatttta tcaacttctt atcagttttgc aaaagaaata gccatggctt    4620
gtagtgctgc gctgtgccct cacctgaaaa ctctaaaaag taatgggatg aataaaattg    4680
gactcagagt ttccattgac actgatatgg ttgaatttca ggcaggatct gaaggccaac    4740
ttctgcctca gcattatcta aatgatcttg atagtgctct gatacctgtg atccatggtg    4800
ggacctccaa ctctagtttta ccattagaaa tagaattagt gttttttcatt atagaacatc    4860 tttttttagtg aaagaatgtg ccatattaca tattgcaacc taatttgtta aaactaactc    4920
cagcactaaa gctgaaatgc cacaaacact aaaagtataa atatgtctga ttttttgaaac    4980 acataagctt tgctctttag gcaggaatga tcttttcaaa tcattagcac aatatttaaa    5040
tatctaaaaa tttaagagat ccatactttc tgtagcttta caattaattt aagtactaaa    5100
aagacaagga tttcttttaa gaaatttata gcatttactg tgttatttaa atgctaagcc    5160
aaagtatctg cacttaggta tacctctttta tgccaataat gattttaatg aaggctcttt    5220
tcagatgtaa cctatgaag gaaatatctg ctttgtgtat atgccagtta gaatactggt    5280
ttctaaagtc tgtcaaattg tatttcagtg gcacaaaaac cagttttgag gtcttagact    5340
tataattctt tgaataaaac tgataactta tttgtataat tggagtggag acctacctcc    5400
ataattagat aaactctttt tggattataa tcagaatttt gcctttttc ttctcaaatt    5460 attacatatg tatgtattat atatccacat atatagtttt ccctgattaa atggatatta    5520
aaataattgc gggtgcttca ggactttttg cttctatatt taagtatatt gttttttatag    5580 caagaacata ttctgaatgt tttataaatc tttaataatt tatatgtagg taatatttt    5640 gtatcacaat gcattatttt tttttcctcct tccttccaa actataccac tgtatttacc    5700
acttctaaga gtgactgacg acgggccaga tgacccttga agtagtcatt atgtagcaat    5760
aaatgaagcc tgaaacaggt ttttttactt ccactttaat ccttagaaat ttcttggcaa    5820
```

-continued

```
cttcgcatat tttcattgac actggtgtat aagtataaat ttaaatgaac taattacttt      5880
tgcatatttt aaattcttta tatggtagtt attttttata acaggatatt aacataagtt      5940
aaatcctatg tatttgaaat tgttacagag ctttcctctt tacttcaaac agcaaaaaag      6000 tgggggcat attgtagtcc tgtcatttaa gttatgtaaa aaatttaatc attatttga       6060 tgctttaaac attctcatgt gtaatatatg tttttgtatc aaaaacactc atatatttca      6120
agaaaaagaa attatgttaa atagccctgt tttaagaaaa atatttatga agcatctcaa      6180
cttgaagatc aagtcaaagt tataactcag gatctgaggt ctcaagctag gagagactga      6240
gaattttaat cagtttgggc atatagtttg gactgaatca catctgtagt acttagccaa      6300
agacaatttg gaggagaata tcagccttct ggaagtagct acttcctgaa caatgtaaag      6360
tgtcgcagat attcaataaa atggcaacct gttataattt gtgaaattta ttgaaatggt      6420
gtaagatgaa aacaattgca tatcaaaccc aatttatgtt ttctaaatat agtgtatgta      6480
ttctgccatg taagtaattg aacagtctta aaataaccaa atggtagagg gctgttccat      6540
gatgggacag ctttggattt gttttcataa aatctctaca ttcaataaaa attggaatta      6600
tgtgcctgaa gtttggaggc acattttgaa gt                                   6632
```

<210> SEQ ID NO 4
<211> LENGTH: 1539
<212> TYPE: PRT
<213> ORGANISM: Homo sapiens

<400> SEQUENCE: 4

```
Met Asp Ser Tyr Phe Lys Ala Ala Val Ser Asp Leu Asp Lys Leu Leu
 1               5                  10                  15

Asp Asp Phe Glu Gln Asn Pro Asp Glu Gln Asp Tyr Leu Gln Asp Val
                20                  25                  30

Gln Asn Ala Tyr Asp Ser Asn His Cys Ser Val Ser Ser Glu Leu Ala
            35                  40                  45

Ser Ser Gln Arg Thr Ser Leu Leu Pro Lys Asp Gln Glu Cys Val Asn
        50                  55                  60

Ser Cys Ala Ser Ser Glu Thr Ser Tyr Gly Thr Asn Glu Ser Ser Leu
 65                  70                  75                  80

Asn Glu Lys Thr Leu Lys Gly Leu Thr Ser Ile Gln Asn Glu Lys Asn
                85                  90                  95

Val Thr Gly Leu Asp Leu Leu Ser Ser Val Asp Gly Gly Thr Ser Asp
            100                 105                 110

Glu Ile Gln Pro Leu Tyr Met Gly Arg Cys Ser Lys Pro Ile Cys Asp
        115                 120                 125

Leu Ile Ser Asp Met Gly Asn Leu Val His Ala Thr Asn Ser Glu Glu
    130                 135                 140

Asp Ile Lys Lys Leu Leu Pro Asp Asp Phe Lys Ser Asn Ala Asp Ser
145                 150                 155                 160

Leu Ile Gly Leu Asp Leu Ser Ser Val Ser Asp Thr Pro Cys Val Ser
                165                 170                 175

Ser Thr Asp His Asp Ser Asp Thr Val Arg Glu Gln Gln Asn Asp Thr
            180                 185                 190

Ser Ser Glu Leu Gln Asn Arg Glu Ile Gly Gly Ile Lys Glu Leu Gly
        195                 200                 205

Ile Lys Val Asp Thr Thr Leu Ser Asp Ser Tyr Asn Tyr Ser Gly Thr
    210                 215                 220
```

```
Glu Asn Leu Lys Asp Lys Lys Ile Phe Asn Gln Leu Glu Ser Ile Val
225                 230                 235                 240

Asp Phe Asn Met Ser Ser Ala Leu Thr Arg Gln Ser Ser Lys Met Phe
            245                 250                 255

His Ala Lys Asp Lys Leu Gln His Lys Ser Gln Pro Cys Gly Leu Leu
            260                 265                 270

Lys Asp Val Gly Leu Val Lys Glu Glu Val Asp Val Ala Val Ile Thr
            275                 280                 285

Ala Ala Glu Cys Leu Lys Glu Glu Gly Lys Thr Ser Ala Leu Thr Cys
        290                 295                 300

Ser Leu Pro Lys Asn Glu Asp Leu Cys Leu Asn Asp Ser Asn Ser Arg
305                 310                 315                 320

Asp Glu Asn Phe Lys Leu Pro Asp Phe Ser Phe Gln Glu Asp Lys Thr
                325                 330                 335

Val Ile Lys Gln Ser Ala Gln Glu Asp Ser Lys Ser Leu Asp Leu Lys
            340                 345                 350

Asp Asn Asp Val Ile Gln Asp Ser Ser Ala Leu His Val Ser Ser
            355                 360                 365

Lys Asp Val Pro Ser Ser Leu Ser Cys Leu Pro Ala Ser Gly Ser Met
370                 375                 380

Cys Gly Ser Leu Ile Glu Ser Lys Ala Arg Gly Asp Phe Leu Pro Gln
385                 390                 395                 400

His Glu His Lys Asp Asn Ile Gln Asp Ala Val Thr Ile His Glu Glu
                405                 410                 415

Ile Gln Asn Ser Val Val Leu Gly Gly Glu Pro Phe Lys Glu Asn Asp
            420                 425                 430

Leu Leu Lys Gln Glu Lys Cys Lys Ser Ile Leu Leu Gln Ser Leu Ile
        435                 440                 445

Glu Gly Met Glu Asp Arg Lys Ile Asp Pro Asp Gln Thr Val Ile Arg
    450                 455                 460

Ala Glu Ser Leu Asp Gly Gly Asp Thr Ser Ser Thr Val Val Glu Ser
465                 470                 475                 480

Gln Glu Gly Leu Ser Gly Thr His Val Pro Glu Ser Ser Asp Cys Cys
                485                 490                 495

Glu Gly Phe Ile Asn Thr Phe Ser Ser Asn Asp Met Asp Gly Gln Asp
                500                 505                 510

Leu Asp Tyr Phe Asn Ile Asp Glu Gly Ala Lys Ser Gly Pro Leu Ile
            515                 520                 525

Ser Asp Ala Glu Leu Asp Ala Phe Leu Thr Glu Gln Tyr Leu Gln Thr
530                 535                 540

Thr Asn Ile Lys Ser Phe Glu Glu Asn Val Asn Asp Ser Lys Ser Gln
545                 550                 555                 560

Met Asn Gln Ile Asp Met Lys Gly Leu Asp Asp Gly Asn Ile Asn Asn
                565                 570                 575

Ile Tyr Phe Asn Ala Glu Ala Gly Ala Ile Gly Glu Ser His Gly Ile
            580                 585                 590

Asn Ile Ile Cys Glu Thr Val Asp Lys Gln Asn Thr Ile Glu Asn Gly
        595                 600                 605

Leu Ser Leu Gly Glu Lys Ser Thr Ile Pro Val Gln Gln Gly Leu Pro
    610                 615                 620

Thr Ser Lys Ser Glu Ile Thr Asn Gln Leu Ser Val Ser Asp Ile Asn
625                 630                 635                 640

Ser Gln Ser Val Gly Gly Ala Arg Pro Lys Gln Leu Phe Ser Leu Pro
```

```
                        645                 650                 655
Ser Arg Thr Arg Ser Ser Lys Asp Leu Asn Lys Pro Asp Val Pro Asp
                    660                 665                 670

Thr Ile Glu Ser Glu Pro Ser Thr Ala Asp Thr Val Val Pro Ile Thr
                675                 680                 685

Cys Ala Ile Asp Ser Thr Ala Asp Pro Gln Val Ser Phe Asn Ser Asn
            690                 695                 700

Tyr Ile Asp Ile Glu Ser Asn Ser Glu Gly Gly Ser Ser Phe Val Thr
705                 710                 715                 720

Ala Asn Glu Asp Ser Val Pro Glu Asn Thr Cys Lys Glu Gly Leu Val
                725                 730                 735

Leu Gly Gln Lys Gln Pro Thr Trp Val Pro Asp Ser Glu Ala Pro Asn
                740                 745                 750

Cys Met Asn Cys Gln Val Lys Phe Thr Phe Thr Lys Arg Arg His His
            755                 760                 765

Cys Arg Ala Cys Gly Lys Val Phe Cys Gly Val Cys Cys Asn Arg Lys
        770                 775                 780

Cys Lys Leu Gln Tyr Leu Glu Lys Glu Ala Arg Val Cys Val Val Cys
785                 790                 795                 800

Tyr Glu Thr Ile Ser Lys Ala Gln Ala Phe Glu Arg Met Met Ser Pro
                805                 810                 815

Thr Gly Ser Asn Leu Lys Ser Asn His Ser Asp Glu Cys Thr Thr Val
                820                 825                 830

Gln Pro Pro Gln Glu Asn Gln Thr Ser Ser Ile Pro Ser Pro Ala Thr
            835                 840                 845

Leu Pro Val Ser Ala Leu Lys Gln Pro Gly Val Glu Gly Leu Cys Ser
850                 855                 860

Lys Glu Gln Lys Arg Val Trp Phe Ala Asp Gly Ile Leu Pro Asn Gly
865                 870                 875                 880

Glu Val Ala Asp Thr Thr Lys Leu Ser Ser Gly Ser Lys Arg Cys Ser
                885                 890                 895

Glu Asp Phe Ser Pro Leu Ser Pro Asp Val Pro Met Thr Val Asn Thr
            900                 905                 910

Val Asp His Ser His Ser Thr Thr Val Glu Lys Pro Asn Asn Glu Thr
        915                 920                 925

Gly Asp Ile Thr Arg Asn Glu Ile Ile Gln Ser Pro Ile Ser Gln Val
    930                 935                 940

Pro Ser Val Glu Lys Leu Ser Met Asn Thr Gly Asn Glu Gly Leu Pro
945                 950                 955                 960

Thr Ser Gly Ser Phe Thr Leu Asp Asp Val Phe Ala Glu Thr Glu
                965                 970                 975

Glu Pro Ser Ser Pro Thr Gly Val Leu Val Asn Ser Asn Leu Pro Ile
            980                 985                 990

Ala Ser Ile Ser Asp Tyr Arg Leu Leu Cys Asp Ile Asn Lys Tyr Val
        995                 1000                1005

Cys Asn Lys Ile Ser Leu Leu Pro Asn Asp Glu Asp Ser Leu Pro Pro
    1010                1015                1020

Leu Leu Val Ala Ser Gly Glu Lys Gly Ser Val Pro Val Val Glu Glu
1025                1030                1035                1040

His Pro Ser His Glu Gln Ile Ile Leu Leu Glu Gly Glu Gly Phe
                1045                1050                1055

His Pro Val Thr Phe Val Leu Asn Ala Asn Leu Leu Val Asn Val Lys
            1060                1065                1070
```

-continued

```
Phe Ile Phe Tyr Ser Ser Asp Lys Tyr Trp Tyr Phe Ser Thr Asn Gly
    1075                1080                1085

Leu His Gly Leu Gly Gln Ala Glu Ile Ile Ile Leu Leu Cys Leu
    1090                1095                1100

Pro Asn Glu Asp Thr Ile Pro Lys Asp Ile Phe Arg Leu Phe Ile Thr
1105                1110                1115                1120

Ile Tyr Lys Asp Ala Leu Lys Gly Lys Tyr Ile Glu Asn Leu Asp Asn
            1125                1130                1135

Ile Thr Phe Thr Glu Ser Phe Leu Ser Ser Lys Asp His Gly Gly Phe
        1140                1145                1150

Leu Phe Ile Thr Pro Thr Phe Gln Lys Leu Asp Asp Leu Ser Leu Pro
    1155                1160                1165

Ser Asn Pro Phe Leu Cys Gly Ile Leu Ile Gln Lys Leu Glu Ile Pro
    1170                1175                1180

Trp Ala Lys Val Phe Pro Met Arg Leu Met Leu Arg Leu Gly Ala Glu
1185                1190                1195                1200

Tyr Lys Ala Tyr Pro Ala Pro Leu Thr Ser Ile Arg Gly Arg Lys Pro
            1205                1210                1215

Leu Phe Gly Glu Ile Gly His Thr Ile Met Asn Leu Leu Val Asp Leu
        1220                1225                1230

Arg Asn Tyr Gln Tyr Thr Leu His Asn Ile Asp Gln Leu Leu Ile His
    1235                1240                1245

Met Glu Met Gly Lys Ser Cys Ile Lys Ile Pro Arg Lys Lys Tyr Ser
    1250                1255                1260

Asp Val Met Lys Val Leu Asn Ser Ser Asn Glu His Val Ile Ser Ile
1265                1270                1275                1280

Gly Ala Ser Phe Ser Thr Glu Ala Asp Ser His Leu Val Cys Ile Gln
            1285                1290                1295

Asn Asp Gly Ile Tyr Glu Thr Gln Ala Asn Ser Ala Thr Gly His Pro
        1300                1305                1310

Arg Lys Val Thr Gly Ala Ser Phe Val Val Phe Asn Gly Ala Leu Lys
    1315                1320                1325

Thr Ser Ser Gly Phe Leu Ala Lys Ser Ser Ile Val Glu Asp Gly Leu
    1330                1335                1340

Met Val Gln Ile Thr Pro Glu Thr Met Asn Gly Leu Arg Leu Ala Leu
1345                1350                1355                1360

Arg Glu Gln Lys Asp Phe Lys Ile Thr Cys Gly Lys Val Asp Ala Val
            1365                1370                1375

Asp Leu Arg Glu Tyr Val Asp Ile Cys Trp Val Asp Ala Glu Glu Lys
        1380                1385                1390

Gly Asn Lys Gly Val Ile Ser Ser Val Asp Gly Ile Ser Leu Gln Gly
    1395                1400                1405

Phe Pro Ser Glu Lys Ile Lys Leu Glu Ala Asp Phe Glu Thr Asp Glu
    1410                1415                1420

Lys Ile Val Lys Cys Thr Glu Val Phe Tyr Phe Leu Lys Asp Gln Asp
1425                1430                1435                1440

Leu Ser Ile Leu Ser Thr Ser Tyr Gln Phe Ala Lys Glu Ile Ala Met
            1445                1450                1455

Ala Cys Ser Ala Ala Leu Cys Pro His Leu Lys Thr Leu Lys Ser Asn
        1460                1465                1470

Gly Met Asn Lys Ile Gly Leu Arg Val Ser Ile Asp Thr Asp Met Val
    1475                1480                1485
```

```
Glu Phe Gln Ala Gly Ser Glu Gly Gln Leu Leu Pro Gln His Tyr Leu
    1490                1495                1500
Asn Asp Leu Asp Ser Ala Leu Ile Pro Val Ile His Gly Gly Thr Ser
1505                1510                1515                1520
Asn Ser Ser Leu Pro Leu Glu Ile Glu Leu Val Phe Phe Ile Ile Glu
           1525                1530                1535
His Leu Phe

<210> SEQ ID NO 5
<211> LENGTH: 4823
<212> TYPE: DNA
<213> ORGANISM: Xenopus

<400> SEQUENCE: 5
ctgtaagttt gactatgtag gaaagcattt ctgttatcta tgaagtatgt tttagagtca       60
gaccaataac taaacggttt tctttttttt gtttatttcc cctcagatga gactgtctct      120
ccaaagctat tagatgctaa gtggaatcaa atcttagaac cgcattcaca taaagtcgct      180
gataactccg cccttgacaa tgtctgtaaa tcaatcattg ctattgaagc tcatctcaaa      240
gtcaggtcac ccggcttgtc agcccttgtg aggtccacat atgtgaatgg agaagtaggt      300
attgtggcac ctgaaatgcc aaaaatggtg ataggagaca ccattatggc agaggattca      360
cttttttaaca acactggtcc ctctgaaatt gtatgcaacc catctactgt ggagagtcaa      420
agtttacaag ctttagatga tcaatcagtg aatattcaca atgaaaaaag tgttctgctc      480
gctgatggct tttcaccatg cagtagcccc aaaagtatta taaactttga ctgcttgacc      540
atggataacg aaatgccttt gcacagtcaa atgagtgttg atgacaatga caaagaaact      600
gtaacaattt cagtccttcc aacaatcata caggatacta gtaacgtaag cacagaccca      660
gctatcaata aacctggcac taaagaaccc catagagcat taaggaaac cacatcagtt      720
attctgcctg aaataaagcc ttactccaca tgtgctgccc tttcgtttga aaataacaat      780
aaggttccca gttatcaatt aaataataca gatctactca gcgtttcacc agtggttgaa      840
gcatgtagtg agcagcagca aaaacataca tcttccttgc atgaagaaaa acttttttgaa      900
ggtgtttctg caacggagtc cttgtcagcc actgctgcgg aaactgtact ggataatgag      960
gctctccgta gtgctgaatt cttttgacatt gttgtaaaga acttttctga ctcttgtgtg     1020
attaatggcg acttgactaa aagttgtggc ctctctcaag aaagcaatga aaagttttgt     1080
gcaagtaaag agtttgaagg agggtagat gctaatgtct tgttggaaaa tgcatgtgta     1140
gcttataaag aagcaataga tttgcctgaa gaaaatggaa ctaatgcacc aatgtctctg     1200
tacaatgggt gtgattccta tggaatgaaa aacccagccg tagctcaaaa cccaaagaat     1260
ttaccttcaa agaagattc tgtgacagaa gaaaaagaaa ttgaagaaag caagtcagaa     1320
tactatactg gtgtttatga acaacaaaga gaagatgatg ttacagagag aggtggactt     1380
ctgttaaatg ctaaggctga ccaaatgaag aacaatttgc atagtctttg taatcaggtt     1440
ccatccatgc atgggcaaac atcaccaaaa aagggcaaga ttgtgcaatc tctcagtgtt     1500
ccatacggtg gagcacgcac taagcagcca actcatctca aactccatat tccaaagcca     1560
ttgtctgaaa tgttgcagag cgatctcatt cctccaaatg ctggctgcag ctctaaatac     1620
aaaaatgaca tgttaaacaa atcaaatcag ggggataacc tgatttcaga atcactgcgt     1680
gaggattctg cagtgcgcag ccctgttact gatgctaatg gtgatttccc tggagaatac     1740
aggggacctg gcagcttgtg ccttgcagtg tctccagaca gccagacaa cgatctgctt     1800
```

```
gccgggcagt tgggggtacc catctctaag ccatttacta ctctagggga agtggctcca    1860
gtctgggtgc cagattccca agcaccaaac tgcatgaagt gcgaggccag atttacattt    1920
accaaaagga ggcatcactg ccgagcttgt ggaaaggtgt tctgtgctgc ttgttgcagt    1980
ctaaaatgca aactacagta catggataaa aaggaggctc gtgtgtgtgt tatttgtcat    2040
tctgtgctta tgaatgctca agcatgggag aacatgttaa gtgcatcggt ccaaagccca    2100
aatccaaata atcctgctga atactgctca actatccctc cgatgcagca ggcacaagct    2160
tcaggagcac tgagttcccc acctcccact gtcatggtgc cagtgggtgt gttaaaacat    2220
ccaggaactg aagggtcaca gtcaaaggaa cagcgccgtg tttggtttgc tgatggaata    2280
ttacccaacg gagagactgc tgactcagat aatgcaaacg taactacagt ggctgggaca    2340
cttactgtgt cacataccaa caattccaca tcttcagagt ctgagaacac ctctggattc    2400
tgtggaagta taactcaggt tggcagtgca atgaacctta ttccagaaga tgggcttcct    2460
cctatactaa tctctactgg agtaaaagga gattacgcag ttgaggaacg cccttcccag    2520
atgtctgtga tgcagcaact agaggaagga ggaccagatc ctttggtttt tgttctaaat    2580
gcaaatcttt tggccatggt taagatcgtg aactatgtta acaggaaatg ctggtgcttt    2640
actacaaagg gaatgcatgc agtgggccag gctgagatcg taatcctgtt gcagtgcctg    2700
cctgatgaga agtgcctgcc gagggacctg tttagccatt tgttgagct gtatcaggag    2760 gcaattgcag gtaatgtagt ggggaacctg gggcattcct tcctcagcca gagtttcctg    2820
ggtagtaagg atcatggtgg atttctttat gttgcaccaa cctaccagtc cctccaggac    2880
ctggttcttc ctgcagagcc gtacttgttt ggaatcctta ttcaaaagtg ggagactcca    2940
tgggccaaag tgttccccat tcggcttatg ctgcgtttag gtgcagaata cagattgtac    3000
ccatgtccac tcttcagtgt tcgatacaga aaacctctgt ttggggaaac cggacacacc    3060
atcattaatg ttctagccga tttcagaaac tatcagtata ctctgccagt ggtgcagggc    3120
ttggtggtgg atatggaagt cagaaaaact agcattaaaa tccccagcaa tagatacaat    3180
gagatgatga agcaatgaa caaatccaat gagcatgtgt tggccatagg agcatgcttc    3240
aaccagatgg cagactctca ccttgtgtgt gtgcaaaacg atgatggcaa ttaccagacc    3300
caggcaatta gtatccacaa acaaccacgt aaagtgaccg gggccagctt ctttgtcttc    3360
agtggtgcac taaagtcttc ttccggatac ctggccaaat ccagcatagt agaagatggg    3420
gtaatggttc agatcaccgc agagagcatg gatgccctca gacagtccct tcgggagatg    3480
aaggatttca ccattacatg tggaaaagct gatgcagagg agtcacagga acatgtctat    3540
gtccagtggg tggaggatga caagaacttt aacaaaggag ttttttagtcc aatcgatggc    3600 aaaatcaatgg agtctgtgac cagcgtcaag attttcatg gctcagaata caaagctagt    3660
ggaaaaataa ttcgctggat agaggtcttc tttctggaca atgaggagca acagagtggc    3720
ctgagtgacc ctgctgatca cagccgactc actgaaaatg tggccaaagc attctgttta    3780
gcgctttgcc cacacctcaa gctactgaag gaagatggaa tgaccaggtt aggtctgcgg    3840
gtgtcactgg actcagacca ggttggatac caagctggga gcaatgggca actcctgcct    3900
gcccgataca ccaatgattt ggatggtgct ttggtaccag tgatacacgg gggcacatgc    3960 cagtaagtg aagggcctgt cagtatggag ctgatatttt atatccttga gaacatctcc    4020
taggaaagac acatgtgtct cctcacaaac tgccatcgcc caaaccattt gcactttaac    4080
cgcaaaagat tcatttttct tttcttttgc taacactagt attaggtcag ggtgcgagag    4140
gcagacacct gaactcttaa accttctatg cattttcaca gtaaggatca agctgcagct    4200
```

-continued

```
gggaatttcc tgttactaat ccaatgtggg acgttagaag tgatcggtgg cactgactat    4260
ctagctgttc aaccttctct ggctcctcta aggactctag tgccaggggg tgagacattc    4320
aagtttaaaa cgaaaactct aaatacaatc aggaatctca ctctgacctc atttaaatca    4380
tcactgcgac ttttttttcct gctcgcattc tttattttgc atcttactca agtttacatt    4440
gtcaagacca gcctaagcct tcagtccttt ctcaattaaa ctactcgtgc atggcaagga    4500
gactttcgtt gcacagcctg aaatatacca atcacttccc aaaccacaag catgaatcca    4560
acgttttcct gactggttgg ctctgctgtg aaagggacag caatattatt tttctacagt    4620
tgacaaaact tttgtctatg tctgtgtctc tcatgggggga tttgttgcct gatgggcagc    4680
ctccggagag aagaattcca cccgtgtgta atatacagtc taagtgtatg gtctgctatg    4740
taacacctgt tgcgcagtgc aaatgcactg actctctgga aggctataga gttttaaaaa    4800
cggttagtct tttaaaaaaa aaa                                            4823
```

<210> SEQ ID NO 6
<211> LENGTH: 1235
<212> TYPE: PRT
<213> ORGANISM: Xenopus

<400> SEQUENCE: 6

```
Met Pro Lys Met Val Ile Gly Asp Thr Ile Met Ala Glu Asp Ser Leu
 1               5                  10                  15

Phe Asn Asn Thr Gly Pro Ser Glu Ile Val Cys Asn Pro Ser Thr Val
                20                  25                  30

Glu Ser Gln Ser Leu Gln Ala Leu Asp Asp Gln Ser Val Asn Ile His
            35                  40                  45

Asn Glu Lys Ser Val Leu Leu Ala Asp Gly Phe Ser Pro Cys Ser Ser
        50                  55                  60

Pro Lys Ser Ile Ile Asn Phe Asp Cys Leu Thr Met Asp Asn Glu Met
 65                  70                  75                  80

Pro Leu His Ser Gln Met Ser Val Asp Asn Asp Lys Glu Thr Val
                85                  90                  95

Thr Ile Ser Val Leu Pro Thr Ile Ile Gln Asp Thr Ser Asn Val Ser
                100                 105                 110

Thr Asp Pro Ala Ile Asn Lys Pro Gly Thr Lys Glu Pro His Arg Ala
            115                 120                 125

Leu Lys Glu Thr Thr Ser Val Ile Leu Pro Glu Ile Lys Pro Tyr Ser
        130                 135                 140

Thr Cys Ala Ala Leu Ser Phe Glu Asn Asn Lys Val Pro Ser Tyr
145                 150                 155                 160

Gln Leu Asn Asn Thr Asp Leu Leu Ser Val Ser Pro Val Val Glu Ala
                165                 170                 175

Cys Ser Glu Gln Gln Lys His Thr Ser Ser Leu His Glu Glu Lys
                180                 185                 190

Leu Phe Glu Gly Val Ser Ala Thr Glu Ser Phe Ala Ala Thr Ala Ala
            195                 200                 205

Glu Thr Val Leu Asp Asn Glu Ala Leu Arg Ser Ala Glu Phe Phe Asp
        210                 215                 220

Ile Val Val Lys Asn Phe Ser Asp Ser Cys Val Ile Asn Gly Asp Leu
225                 230                 235                 240

Thr Lys Ser Cys Gly Leu Ser Gln Glu Ser Asn Glu Lys Phe Cys Ala
                245                 250                 255
```

-continued

```
Ser Lys Glu Phe Glu Gly Gly Val Asp Ala Asn Val Leu Leu Glu Asn
            260                 265                 270
Ala Cys Val Ala Tyr Lys Glu Ala Ile Asp Leu Pro Glu Asn Gly
        275                 280                 285
Thr Asn Ala Pro Met Ser Leu Tyr Asn Gly Cys Asp Ser Tyr Gly Met
    290                 295                 300
Lys Asn Pro Ala Val Ala Gln Asn Pro Lys Asn Leu Pro Ser Lys Glu
305                 310                 315                 320
Asp Ser Val Thr Glu Glu Lys Glu Ile Glu Glu Ser Lys Ser Glu Tyr
                325                 330                 335
Tyr Thr Gly Val Tyr Glu Gln Gln Arg Glu Asp Val Thr Glu Arg
            340                 345                 350
Gly Gly Leu Leu Leu Asn Ala Lys Ala Asp Gln Met Lys Asn Asn Leu
            355                 360                 365
His Ser Leu Cys Asn Gln Val Pro Ser Met His Gly Gln Thr Ser Pro
    370                 375                 380
Lys Lys Gly Lys Ile Val Gln Ser Leu Ser Val Pro Tyr Gly Gly Ala
385                 390                 395                 400
Arg Thr Lys Gln Pro Thr His Leu Lys Leu His Ile Pro Lys Pro Leu
                405                 410                 415
Ser Glu Met Leu Gln Ser Asp Leu Ile Pro Pro Asn Ala Gly Cys Ser
            420                 425                 430
Ser Lys Tyr Lys Asn Asp Met Leu Asn Lys Ser Asn Gln Gly Asp Asn
        435                 440                 445
Leu Ile Ser Glu Ser Leu Arg Glu Asp Ser Ala Val Arg Ser Pro Val
    450                 455                 460
Thr Asp Ala Asn Gly Asp Phe Pro Gly Glu Tyr Arg Gly Pro Gly Ser
465                 470                 475                 480
Leu Cys Leu Ala Val Ser Pro Asp Ser Pro Asp Asn Asp Leu Leu Ala
                485                 490                 495
Gly Gln Phe Gly Val Pro Ile Ser Lys Pro Phe Thr Thr Leu Gly Glu
            500                 505                 510
Val Ala Pro Val Trp Val Pro Asp Ser Gln Ala Pro Asn Cys Met Lys
            515                 520                 525
Cys Glu Ala Arg Phe Thr Phe Thr Lys Arg Arg His His Cys Arg Ala
530                 535                 540
Cys Gly Lys Val Phe Cys Ala Ala Cys Cys Ser Leu Lys Cys Lys Leu
545                 550                 555                 560
Gln Tyr Met Asp Lys Lys Glu Ala Arg Val Cys Val Ile Cys His Ser
                565                 570                 575
Val Leu Met Asn Ala Gln Ala Trp Glu Asn Met Leu Ser Ala Ser Val
            580                 585                 590
Gln Ser Pro Asn Pro Asn Asn Pro Ala Glu Tyr Cys Ser Thr Ile Pro
        595                 600                 605
Pro Met Gln Gln Ala Gln Ala Ser Gly Ala Leu Ser Ser Pro Pro
    610                 615                 620
Thr Val Met Val Pro Val Gly Val Leu Lys His Pro Gly Thr Glu Gly
625                 630                 635                 640
Ser Gln Ser Lys Glu Gln Arg Arg Val Trp Phe Ala Asp Gly Ile Leu
                645                 650                 655
Pro Asn Gly Glu Thr Ala Asp Ser Asp Asn Ala Asn Val Thr Thr Val
            660                 665                 670
Ala Gly Thr Leu Thr Val Ser His Thr Asn Asn Ser Thr Ser Ser Glu
```

```
                675                 680                 685
Ser Glu Asn Thr Ser Gly Phe Cys Gly Ser Ile Thr Gln Val Gly Ser
            690                 695                 700
Ala Met Asn Leu Ile Pro Glu Asp Gly Leu Pro Pro Ile Leu Ile Ser
705                 710                 715                 720
Thr Gly Val Lys Gly Asp Tyr Ala Val Glu Glu Arg Pro Ser Gln Met
                725                 730                 735
Ser Val Met Gln Gln Leu Glu Glu Gly Gly Pro Asp Pro Leu Val Phe
                740                 745                 750
Val Leu Asn Ala Asn Leu Leu Ala Met Val Lys Ile Val Asn Tyr Val
                755                 760                 765
Asn Arg Lys Cys Trp Cys Phe Thr Thr Lys Gly Met His Ala Val Gly
            770                 775                 780
Gln Ala Glu Ile Val Ile Leu Leu Gln Cys Leu Pro Asp Glu Lys Cys
785                 790                 795                 800
Leu Pro Arg Asp Leu Phe Ser His Phe Val Glu Leu Tyr Gln Glu Ala
                805                 810                 815
Ile Ala Gly Asn Val Val Gly Asn Leu Gly His Ser Phe Leu Ser Gln
            820                 825                 830
Ser Phe Leu Gly Ser Lys Asp His Gly Gly Phe Leu Tyr Val Ala Pro
                835                 840                 845
Thr Tyr Gln Ser Leu Gln Asp Leu Val Leu Pro Ala Glu Pro Tyr Leu
            850                 855                 860
Phe Gly Ile Leu Ile Gln Lys Trp Glu Thr Pro Trp Ala Lys Val Phe
865                 870                 875                 880
Pro Ile Arg Leu Met Leu Arg Leu Gly Ala Glu Tyr Arg Leu Tyr Pro
                885                 890                 895
Cys Pro Leu Phe Ser Val Arg Tyr Arg Lys Pro Leu Phe Gly Glu Thr
            900                 905                 910
Gly His Thr Ile Ile Asn Val Leu Ala Asp Phe Arg Asn Tyr Gln Tyr
            915                 920                 925
Thr Leu Pro Val Val Gln Gly Leu Val Val Asp Met Glu Val Arg Lys
            930                 935                 940
Thr Ser Ile Lys Ile Pro Ser Asn Arg Tyr Asn Glu Met Met Lys Ala
945                 950                 955                 960
Met Asn Lys Ser Asn Glu His Val Leu Ala Ile Gly Ala Cys Phe Asn
                965                 970                 975
Gln Met Ala Asp Ser His Leu Val Cys Val Gln Asn Asp Asp Gly Asn
            980                 985                 990
Tyr Gln Thr Gln Ala Ile Ser Ile His Lys Gln Pro Arg Lys Val Thr
            995                 1000                1005
Gly Ala Ser Phe Phe Val Phe Ser Gly Ala Leu Lys Ser Ser Ser Gly
        1010                1015                1020
Tyr Leu Ala Lys Ser Ser Ile Val Glu Asp Gly Val Met Val Gln Ile
1025                1030                1035                1040
Thr Ala Glu Ser Met Asp Ala Leu Arg Gln Ser Leu Arg Glu Met Lys
                1045                1050                1055
Asp Phe Thr Ile Thr Cys Gly Lys Ala Asp Ala Glu Glu Ser Gln Glu
            1060                1065                1070
His Val Tyr Val Gln Trp Val Glu Asp Lys Asn Phe Asn Lys Gly
        1075                1080                1085
Val Phe Ser Pro Ile Asp Gly Lys Ser Met Glu Ser Val Thr Ser Val
        1090                1095                1100
```

```
Lys Ile Phe His Gly Ser Glu Tyr Lys Ala Ser Gly Lys Ile Ile Arg
1105                1110                1115                1120

Trp Ile Glu Val Phe Phe Leu Asp Asn Glu Glu Gln Gln Ser Gly Leu
                1125                1130                1135

Ser Asp Pro Ala Asp His Ser Arg Leu Thr Glu Asn Val Ala Lys Ala
        1140                1145                1150

Phe Cys Leu Ala Leu Cys Pro His Leu Lys Leu Lys Glu Asp Gly
            1155                1160                1165

Met Thr Arg Leu Gly Leu Arg Val Ser Leu Asp Ser Asp Gln Val Gly
    1170                1175                1180

Tyr Gln Ala Gly Ser Asn Gly Gln Leu Leu Pro Ala Arg Tyr Thr Asn
1185                1190                1195                1200

Asp Leu Asp Gly Ala Leu Val Pro Val Ile His Gly Gly Thr Cys Gln
                1205                1210                1215

Leu Ser Glu Gly Pro Val Ser Met Glu Leu Ile Phe Tyr Ile Leu Glu
            1220                1225                1230

Asn Ile Ser
    1235

<210> SEQ ID NO 7
<211> LENGTH: 2678
<212> TYPE: DNA
<213> ORGANISM: Xenopus

<400> SEQUENCE: 7 agttttatttt tcagaagacg ttgcatcttt attttaaaca ttaagtttca ctatgtagta      60
aaacattact gttgtatata cagtatgttg tagacatata acgtaactgt ttgctttgtg     120 cttctttcc tcctcagatg aaactgtctt tccaaagctg ttagatgcta agtggaatca     180
attcttagaa ccacattcgc ataaagtcac tgataaacca gctcttgaca atgtctgtaa     240
atcaatcatt gctattgaag ctcatctcaa agtcaggtca cccagcttga cagcccttgc     300
aaggtccaca tatgtgaatg gagaagtagg tattgtgact cctgaaatgc taaaatggt      360 gataggagac accgatatgg cagaggattc acttttaaac actggtccct ctgaaattgt     420
atgcaactct attgtggaga gtcaaagttt agaagtttta gatgatgtac cagtgagtat     480
taacaatgaa aaagtgttc ttcttgatga tggattttct ccgtacagta gccccaaaag     540
tgttctaaac tctgcttgct tgaccatgaa taacggaaag ccctcacacg gtcaaaaaat     600
tgttaatgac caagataaag aagctgtaac aatttcagtc cttccaatga tcatacagga     660
tactactaac gtaagcacag acccagcttt caataaatct ggcactgaag aagcttatag     720
tgcattaaaa caaccacat cagttattct gcctgaaata aagccttatt ccatacaggc     780 tgcccttttca tgtgaaaata tcaacaagat acccagatgt caattaaata atacagatct     840
actcagcatt tcaccagtgg ttgaagcatg tagtgagaag cagcaaaatc atacaacttc     900
cttgcatgaa aaaaacttg cagctgtgtc tgcaactgcg ttctttccag tcactgctgc     960
tgaaactgta ctaggtaatg aagctctcca tagtgctgat tttttttgaca ttgttgtaaa    1020 gaacgtttct gactcgtgtg tgtttaatgg tgacctaact agaactaatg gactctcaca    1080
agaaaacaat gaaatgtttt atgcaagtaa agagttggaa ggaggggtag atgctaatat    1140
cttattggaa gatgcatgca tagcttataa agaaagaata gatttgtctg aagaaaatgg    1200
aactaatgca ccaatgtatc tgtacaatgg gtgtgattcc tatggaatga aaaccctgc    1260 tgtacgtcaa aacccaaaga atttaccatc aaaagaagat tctgtgacag aagaaaaaga    1320
```

-continued

```
aattgaagaa agcaagtcag aatactattc tggtgtttat gaacaacaga aggaagatga    1380
cataactgag agaggtggag tcttgttaaa tgccaaggtt gaccaaatga agaacagttt    1440
gcatagtctt tataatccgg ttccatccat gcatgggcaa acctcaccaa aaaagggcaa    1500
gattgtgcaa tccctcagtg ttccatatgg tggagctcgc cccaagcagc caactcatct    1560
caaactcaat attccacagc cattgtctga aatgttacag tgtgatctca ttccgccaaa    1620
tgctggatgc agctctaaaa acaaaaatga catgttaaac aaatcaaatc gggggggataa    1680 cctgatttca gaatcactac gtgaggaagt gcacagccct gttactgata caaatggtga    1740
agtccctcga gaaacaggg gacctggcag cctgtgcctt gcagtgtctc cagacagccc    1800
tgacaatgat ctgcttgctg acagtttgg ggtacccatc tctaagccat ttactactct    1860 agggggatgtg gctccagtct gggtgccaga ttcccaagca ccaaactgca tgaagtgcga    1920
ggccagattt acatttacca aaggaggca tcactgccga gcttgtggaa aggtatgtaa    1980
agaaatgtgg tgtttcatca gggcaacagt aatcacggca aattattcat aacaaaatgt    2040
gttcagcaga ttcagttaaa gtagacttat aagttacaca gtaacaattc atctgctcag    2100
cctcattttg aagtagataa aatatatttt attaggaaac tctggggaga tataagggaa    2160
agcttgccta aaagtagatg ttctgtatat tatttggtag tcaaagatga tttcatgaaa    2220
aaaggttatt tgtaaaaagt acaaaatggg tagagactac acaataaaaa gtaaggagta    2280
aaaaactagg tatgtaacgt atattaaaat aattttatga ttttaatatt tactgcacat    2340
tttctacagt gcagtgattt gtataaccat gcaattatca aatgcttagt gccttcacac    2400
aaagtgcctt taataaaaat tatttttataa attatcatat tttctttata tgtagtcatc    2460
atcttttttg tctcatttct tggaatcgtt ctacttatgt tctactgata tgttttttac    2520
ccgagaccta tcttgtcctc taaagtaatt ggcttgtcaa ctggctgtag ggggattttc    2580
agagttatag cttagtactg ttaatgagcc ataggttgaa atagtgctct agatttacat    2640
gttgtacaac agttattgca atatgtgtag ggggggg                            2678
```

<210> SEQ ID NO 8
<211> LENGTH: 561
<212> TYPE: PRT
<213> ORGANISM: Xenopus

<400> SEQUENCE: 8

```
Met Pro Lys Met Val Ile Gly Asp Thr Asp Met Ala Glu Asp Ser Leu
  1               5                  10                  15

Phe Asn Thr Gly Pro Ser Glu Ile Val Cys Asn Ser Ile Val Glu Ser
             20                  25                  30

Gln Ser Leu Glu Val Leu Asp Asp Val Pro Val Ser Ile Asn Asn Glu
         35                  40                  45

Lys Ser Val Leu Asn Ser Ala Cys Leu Thr Met Asn Asn Gly Lys Pro Ser
     50                  55                  60

Ser Val Leu Asn Ser Ala Cys Leu Thr Met Asn Asn Gly Lys Pro Ser
 65                  70                  75                  80

His Gly Gln Lys Ile Val Asn Asp Gln Asp Lys Glu Ala Val Thr Ile
                 85                  90                  95

Ser Val Leu Pro Met Ile Ile Gln Asp Thr Thr Asn Val Ser Thr Asp
            100                 105                 110

Pro Ala Phe Asn Lys Ser Gly Thr Glu Glu Ala Tyr Ser Ala Leu Lys
        115                 120                 125
```

```
Gln Thr Thr Ser Val Ile Leu Pro Glu Ile Lys Pro Tyr Ser Ile Gln
    130                 135                 140

Ala Ala Leu Ser Cys Glu Asn Ile Asn Lys Ile Pro Arg Cys Gln Leu
145                 150                 155                 160

Asn Asn Thr Asp Leu Leu Ser Ile Ser Pro Val Val Glu Ala Cys Ser
                165                 170                 175

Glu Lys Gln Gln Asn His Thr Thr Ser Leu His Glu Lys Lys Leu Ala
                180                 185                 190

Ala Val Ser Ala Thr Ala Phe Phe Pro Val Thr Ala Ala Glu Thr Val
            195                 200                 205

Leu Gly Asn Glu Ala Leu His Ser Ala Asp Phe Phe Asp Ile Val Val
        210                 215                 220

Lys Asn Val Ser Asp Ser Cys Val Phe Asn Gly Asp Leu Thr Arg Thr
225                 230                 235                 240

Asn Gly Leu Ser Gln Glu Asn Asn Glu Met Phe Tyr Ala Ser Lys Glu
                245                 250                 255

Leu Glu Gly Gly Val Asp Ala Asn Ile Leu Leu Glu Asp Ala Cys Ile
                260                 265                 270

Ala Tyr Lys Glu Arg Ile Asp Leu Ser Glu Glu Asn Gly Thr Asn Ala
        275                 280                 285

Pro Met Tyr Leu Tyr Asn Gly Cys Asp Ser Tyr Gly Met Lys Asn Pro
    290                 295                 300

Ala Val Arg Gln Asn Pro Lys Asn Leu Pro Ser Lys Glu Asp Ser Val
305                 310                 315                 320

Thr Glu Glu Lys Glu Ile Glu Glu Ser Lys Ser Glu Tyr Tyr Ser Gly
                325                 330                 335

Val Tyr Glu Gln Gln Lys Glu Asp Asp Ile Thr Glu Arg Gly Gly Val
                340                 345                 350

Leu Leu Asn Ala Lys Val Asp Gln Met Lys Asn Ser Leu His Ser Leu
        355                 360                 365

Tyr Asn Pro Val Pro Ser Met His Gly Gln Thr Ser Pro Lys Lys Gly
    370                 375                 380

Lys Ile Val Gln Ser Leu Ser Val Pro Tyr Gly Gly Ala Arg Pro Lys
385                 390                 395                 400

Gln Pro Thr His Leu Lys Leu Asn Ile Pro Gln Pro Leu Ser Glu Met
                405                 410                 415

Leu Gln Cys Asp Leu Ile Pro Asn Ala Gly Cys Ser Ser Lys Asn
                420                 425                 430

Lys Asn Asp Met Leu Asn Lys Ser Asn Arg Gly Asp Asn Leu Ile Ser
                435                 440                 445

Glu Ser Leu Arg Glu Glu Val His Ser Pro Val Thr Asp Thr Asn Gly
        450                 455                 460

Glu Val Pro Arg Glu Asn Arg Gly Pro Gly Ser Leu Cys Leu Ala Val
465                 470                 475                 480

Ser Pro Asp Ser Pro Asp Asn Asp Leu Leu Ala Gly Gln Phe Gly Val
                485                 490                 495

Pro Ile Ser Lys Pro Phe Thr Thr Leu Gly Asp Val Ala Pro Val Trp
                500                 505                 510

Val Pro Asp Ser Gln Ala Pro Asn Cys Met Lys Cys Glu Ala Arg Phe
                515                 520                 525
```

```
Thr Phe Thr Lys Arg Arg His His Cys Arg Ala Cys Gly Lys Val Cys
    530                 535                 540

Lys Glu Met Trp Cys Phe Ile Arg Ala Thr Val Ile Thr Ala Asn Tyr
545                 550                 555                 560

Ser
```

SARA PROTEINS

RELATED APPLICATION INFORMATION

This application claims the benefit under 35 U.S.C. § 371 from PCT Application No. PCT/CA99/00656, filed Jul. 20, 1999, the disclosure of which is incorporated by reference herein in its entirety, which claims the benefit of Canadian Application Serial No. 2,237,701, filed Jul. 20, 1998 and Canadian Application Serial No. 2,253,647, filed Dec. 10, 1998, the disclosures of which are incorporated by reference herein in their entirety.

FIELD OF THE INVENTION

The invention relates to a family of proteins, the SARA proteins, which bind to receptor-regulated Smad proteins and are involved in appropriate localization of these Smad proteins for receptor activation.

BACKGROUND OF THE INVENTION

The Transforming Growth Factor-beta (TGFβ) superfamily, whose members include TGFβs, activins and bone morphogenetic proteins (BMPs), have wide ranging effects on cells of diverse origins (Attisano and Wrana, 1998; Heldin et al., 1997; Kretzschmar and Massagué, 1998). Signaling by these secreted factors is initiated upon interaction with a family of cell-surface transmembrane serine/threonine kinases, known as type I and type II receptors. Ligand induces formation of a typeI/typeII heteromeric complex which permits the constitutively active type II receptor to phosphorylate, and thereby activate, the type I receptor (Wrana et al., 1994). This activated type I receptor then propagates the signal to a family of intracellular signaling mediators known as Smads (Attisano and Wrana, 1998; Heldin et al., 1997; Kretzschmar and Massagué, 1998).

The first members of the Smad family identified in invertebrates were the *Drosophila* MAD and the *C. elegans* sma genes (sma-2, sma-3 and sma4; Savage et al., 1996; Sekelsky et al., 1995). Currently, the family includes additional invertebrate Smads, as well as nine vertebrate members, Smad1 through 9 (Attisano and Wrana, 1998; Heldin et al., 1997; Kretzschmar and Massagué, 1998). Smad proteins contain two conserved amino (MH1) and carboxy (MH2) terminal regions separated by a more divergent linker region. In general, Smad proteins can be subdivided into three groups; the receptor-regulated Smads, which include Smad 1, 2, 3, 5 and 8, Mad, sma-2 and sma-3; the common Smads, Smad4 and Medea, and the antagonistic Smads, which include Smad6, 7 and 9, DAD and daf-3 (Heldin et al., 1997; Nakayama et al., 1998; Patterson et al., 1997).

Numerous studies with vertebrate Smad proteins have provided insights into the differential functions of these proteins in mediating signaling. Receptor-regulated Smads are direct substrates of specific type I receptors and the proteins are phosphorylated on the last two serines at the carboxy-terminus within a highly conserved SSXS motif (Abdollah et al., 1997; Kretzschmar et al., 1997; Liu et al., 1997b; Macias-Silva et al., 1996; Souchelnytskyi et al., 1997). Interestingly, Smad2 and Smad3 are substrates of TGFβ or activin receptors and mediate signaling by these ligands (Liu et al., 1997b; Macias-Silva et al., 1996; Nakao et al., 1997a), whereas Smad1, 5 and 8 appear to be targets of BMP receptors and thereby propagate BMP signals (Chen et al., 1997b; Hoodless et al., 1995; Kretzschmar et al., 1997; Nishimura et al., 1998). Once phosphorylated, these Smads bind to the common Smad, Smad4, which lacks the carboxy-terminal phosphorylation site and is not a target for receptor phosphorylation (Lagna et al., 1996; Zhang et al., 1997). Heteromeric complexes of the receptor-regulated Smad and Smad4 translocate to the nucleus where they function to regulate the transcriptional activation of specific target genes. The antagonist Smads, Smad6, 7 and 9 appear to function by blocking ligand-dependent signaling by preventing access of receptor-regulated Smads to the type I receptor or possibly by blocking formation of heteromeric complexes with Smad4 (reviewed in Heldin et al., 1997).

Analysis of the nuclear function of Smads has demonstrated that Smads can act as transcriptional activators and that some Smads, including *Drosophila* Mad, and the vertebrate Smad3 and Smad4, can bind directly to DNA, albeit at relatively low specificity and affinity (Dennler et al., 1998; Kim et al., 1997; Labbé et al., 1998; Yingling et al., 1997; Zawel et al., 1998).

Localization of Smads is critical in controlling their activity and Smad phosphorylation by the type I receptor regulates Smad activity by inducing nuclear accumulation (Attisano and Wrana, 1998; Heldin et al., 1997; Kretzschmar and Massagué, 1998). However, little is known about how Smad localization is controlled prior to phosphorylation and how this might function in modulating receptor interactions with its Smad substrates.

SUMMARY OF THE INVENTION

Smad proteins (Smads) transmit signals from transmembrane ser/thr kinase receptors to the nucleus. Mammalian and non-mammalian proteins have been identified which interact directly with Smads and are designated the Smad Anchor for Receptor Activation or SARA proteins.

The invention provides cDNA sequences encoding this previously undescribed family of SARA proteins which bind to receptor-regulated Smad proteins and ensure appropriate localization of these Smad proteins for activation by a Type I receptor of a TGFβ, activin or BMP signaling pathway.

For example, TGFβ signaling induces dissociation of Smad2 or Smad3 from a SARA protein with concomitant formation of Smad2/Smad4 or Smad3/Smad4 complexes and nuclear translocation. In the absence of signaling, SARA functions to recruit a particular Smad (eg. Smad2 or Smad3) to distinct subcellular sites in the cell and interacts with the TGFβ superfamily receptor complex in cooperation with the particular receptor regulated Smad. Mutations in hSARA1 that cause mislocalization of Smad2, and interfere with receptor association, inhibit receptor-dependent transcriptional responses, indicating that regulation of Smad localization is essential for TGFβ superfamily signaling. The invention provides a novel component of the signal transduction pathway that functions to anchor Smads to specific subcellular sites for activation by the Type I receptor of the TGFβ, activin or BMP signaling pathways.

The SARA proteins are characterised by the presence of three domains, a double zinc finger or FYVE domain responsible for the subcellular localisation of the SARA protein or SARA-Smad complex, a Smad-binding domain which mediates the interaction or binding of one or more species of Smad protein and a carboxy terminal domain which mediates association with the TGFβ superfamily receptor. The FYVE domain may bind phosphatidyl inositol-3-phosphate.

In accordance with one embodiment, the invention provides isolated polynucleotides comprising nucleotide sequences encoding SARA proteins.

In accordance with a further series of embodiments, the invention provides an isolated polynucleotide selected from the group consisting of
(a) a nucleotide sequence encoding a human SARA protein;
(b) a nucleotide sequence encoding a mammalian SARA protein;
(c) a nucleotide sequence encoding a non-mammalian SARA protein;
(d) a nucleotide sequence encoding the human SARA amino acid sequence of Table 2 (hSARA1: Sequence ID NO:2);
(e) a nucleotide sequence encoding the human SARA amino acid sequence of Table 4 (hSARA2: Sequence ID NO:4);
(f) a nucleotide sequence encoding the *Xenopus* SARA amino acid sequence of Table 6 (XSARA1: Sequence ID NO:6);
(g) a nucleotide sequence encoding the *Xenopus* SARA amino acid sequence of Table 8 (XSARA2: Sequence ID NO:8).

In accordance with a further embodiment, the invention provides the nucleotide sequences of Table 1 (human SARA1 or hSARA 1), Table 3 (human SARA2 or hSARA 2), Table 5 (*Xenopus* SARA1 or XSARA 1) and Table 7 (*Xenopus* SARA2 or XSARA 2).

In accordance with a further embodiment, the invention provides recombinant vectors including the polynucleotides disclosed herein and host cells transformed with these vectors.

The invention further provides a method for producing SARA proteins, comprising culturing such host cells to permit expression of a SARA protein-encoding polynucleotide and production of the protein.

The invention also includes polynucleotides which are complementary to the disclosed nucleotide sequences, polynucleotides which hybridize to these sequences under high stringency and degeneracy equivalents of these sequences.

In accordance with a further embodiment, the invention provides antisense molecules which may be used to prevent expression of a SARA protein. Such antisense molecules can be synthesised by methods known to those skilled in the art and include phosphorothioates and similar compounds.

The invention further includes polymorphisms and alternatively spliced versions of the disclosed SARA genes and proteins wherein nucleotide or amino acid substitutions or deletions do not substantially affect the functioning of the gene or its encoded protein.

The invention also enables the identification and isolation of allelic variants or homologues of the described SARA genes, and their corresponding proteins, using standard hybridisation screening or PCR techniques.

The invention provides a method for identifying allelic variants or homologues of the described SARA genes, comprising
choosing a nucleic acid probe or primer capable of hybridizing to a SARA gene sequence under stringent hybridisation conditions;
mixing the probe or primer with a sample of nucleic acids which may contain a nucleic acid corresponding to the variant or homologue; and
detecting hybridisation of the probe or primer to the nucleic acid corresponding to the variant or homologue.

In accordance with a further embodiment, the invention provides fragments of the disclosed polynucleotides, such as polynucleotides of at least 10, preferably 15, more preferably 20 consecutive nucleotides of the disclosed polynucleotide sequences. These fragments are useful as probes and PCR primers or for encoding fragments, functional domains or antigenic determinants of SARA proteins.

In accordance with a further embodiment, the invention provides substantially purified SARA proteins, including the proteins of Table 2 (hSARA1), Table 4 (hSARA2), Table 6 (XSARA1) and Table 8 (XSARA2).

In accordance with one embodiment, a SARA protein has a FYVE domain, a Smad binding domain (SBD) and an amino acid sequence having at least 50% overall identity with the amino acid sequence of hSARA1 (Sequence ID NO:2).

In accordance with a preferred embodiment, a SARA protein has a FYVE domain having at least 65% identity of amino acid sequence with the FYVE domain of hSARA1 and a C-terminal sequence of 550 consecutive amino acids which have at least 50% identity with the C-terminal 550 amino acid residues of hSARA1.

In accordance with a more preferred embodiment, a SARA protein has a FYVE domain having at least 65% identity of amino acid sequence with the FYVE domain of hSARA1 and wherein the portion of the SBD corresponding to amino acid residues 721 to 740 of hSARA1 has at least 80% identity with that portion of hSARA1.

The invention further provides a method for producing antibodies which selectively bind to a SARA protein comprising the steps of
administering an immunogenically effective amount of a SARA immunogen to an animal;
allowing the animal to produce antibodies to the immunogen; and
obtaining the antibodies from the animal or from a cell culture derived therefrom.

The invention further provides substantially pure antibodies which bind selectively to an antigenic determinant of a SARA protein. The antibodies of the invention include polyclonal antibodies, monoclonal antibodies and single chain antibodies.

The invention includes analogues of the disclosed protein sequences, having conservative amino acid substitutions therein. The invention also includes fragments of the disclosed protein sequences, such as peptides of at least 6, preferably 10, more preferably 20 consecutive amino acids of the disclosed protein sequences.

The invention further provides polypeptides comprising at least one functional domain or at least an antigenic determinant of a SARA protein.

In accordance with a further embodiment, the invention provides peptides which comprise SARA protein Smad binding domains and polynucleotides which encode such peptides.

In accordance with a further embodiment, the invention provides a Smad binding domain peptide selected from the group consisting of
(a) SASSQSPNPNNPAEYCSTIPPLQQAQAS-GALSSPPPTVMVPVGV LKHPGAEVAQPREQR-RVWFADGILPNGEVADAAKLTMNGTSS; and
(b) amino acids 589 to 672 of the XSARA1 sequence of Table 9.

The invention includes fragments and variants of these Smad binding domain peptides which retain the ability to bind a Smad protein.

In accordance with a further embodiment, the invention provides peptides which comprise SARA protein FYVE domains and polynucleotides which encode such peptides.

In accordance with a further embodiment, the invention provides a FYVE domain peptide selected from the group consisting of (a) amino acids 587 to 655 of the hSARA1 sequence of Table 9;
(b) amino acids 510 to 578 of the XSARA1 sequence of Table 9; and
(c) the consensus amino acid sequence of Table 10.

The invention includes fragments and variants of these FYVE domain peptides which retain the function of the parent peptide.

In accordance with a further embodiment, the invention provides peptides which comprise SARA protein TGFβ receptor interacting domains and polynucleotides which encode such peptides.

In accordance with a further embodiment, the invention provides a TGFβ receptor interacting domain peptide comprising amino acids 751 to 1323 of the hSARA1 sequence of Table 9.

The invention includes fragments and variants of these TGFβ receptor binding domain peptides which retain the binding ability of the parent peptide.

The invention further provides methods for modulating signaling by members of the TGFβ superfamily which signal through pathways which involve a SARA protein.

Modulation of signaling by a TGFβ superfamily member through such a pathway may be effected, for example, by increasing or reducing the binding of the SARA protein involved in the pathway with its binding partner.

In accordance with a further embodiment, TGFβ superfamily signaling, including TGFβ signaling, by a pathway involving a SARA protein described herein may be modulated by modulating the binding of the SARA protein to a Smad binding partner, by modulating the binding of its FYVE domain to its binding partner or by modulating the binding of the SARA protein to a TGFβ superfamily receptor, such as the TGFβ receptor.

For example, the binding of a SARA protein to a Smad binding partner may be inhibited by a deletion mutant of the protein lacking either the SBD domain or the FYVE domain or by the SARA protein Smad binding domain peptides or FYVE domain peptides described herein, and effective fragments or variants thereof. The binding of a SARA protein to a TGFβ superfamily receptor may be inhibited by a deletion mutant of the protein lacking a C terminal portion or by the SARA protein TGFβ receptor binding domain peptides described herein, and effective fragments and variants thereof.

In accordance with a further embodiment, TGFβ superfamily signaling, including TGFβ signaling, by a pathway involving a SARA protein may be modulated by modulating the binding of the SARA protein FYVE domain to phosphatidyl inositol-3-phosphate, by increasing or decreasing the availability of phosphatidyl inositol-3-phosphate or by administration of agonists or antagonists of phosphatidyl inositol-3phosphate kinase.

The invention also provides a method of modulating a TGFβ superfamily signaling pathway involving phosphatidyl inositol-3-phosphate, including a TGFβ signaling pathway, by increasing or decreasing the availability of SARA protein or by modulating the function of SARA protein.

The invention further provides methods for preventing or treating diseases characterised by an abnormality in a TGFβ superfamily member signaling pathway which involves a SARA protein, by modulating signaling in the pathway, as described above.

TGFβ signaling is important in wound healing, and excessive signaling is associated with scarring, with arthritis and with fibrosis in numerous diseases, including fibrosis of the liver and kidney. TGFβ signaling is also involved in modulating inflammatory and immune responses and can contribute to tumour progression.

The invention thus provides methods for modulating TGFβ-dependent cell proliferation or fibrogenesis.

The BMP signaling pathways are important in tissue morphogenesis and in protecting tissues and restoring or regenerating tissues after tissue damage, for example in bone, kidney, liver and neuronal tissue (see, for example, (Reddy, A. H. (1998), *Nature Biotechnology*, v. 16, pp. 247–252).

The invention further provides methods for modulating BMP-dependent phenotypic marker expression by modulating the interactions of SARA proteins involved in these BMP signaling pathways.

In accordance with a further embodiment, modified versions of a SARA protein may be provided as dominant-negatives that block TGFβ superfamily signaling. These modified versions of SARA could, for example, lack the Smad binding domain and thereby prevent recruitment of Smad or could lack the FYVE domain and thereby inhibit signaling by interfering with translocation.

These modified versions of SARA may be provided by gene therapy, for example using transducing viral vectors. Expression may be driven by inclusion in the vector of a promoter specific for a selected target cell type. Many examples of such specific promoters are known to those skilled in the art.

In a further embodiment, a normal version of a SARA protein such as hSARA1 could be provided by gene therapy to restore function in a disease wherein SARA is mutated or non-functional.

In a further embodiment, the invention provides a pharmaceutical composition comprising a purified SARA protein as active ingredient.

In accordance with a further embodiment, the invention provides non-human transgenic animals and methods for the production of non-human transgenic animals which afford models for further study of the SARA system and tools for screening of candidate compounds as therapeutics. For example, knock out animals, such as mice, may be produced with deletion of a SARA gene.

These animals may be examined for phenotypic changes and used to screen candidate compounds for effectiveness to reverse these changes.

In a further example, transgenic animals may be produced expressing a dominant negative mutant of a SARA protein, as described above, either generally or in specific targeted tissues.

The invention provides many targets for the development of small molecule drugs, including peptides and peptidomimetic drugs, to interfere with the interaction of the various binding partners described herein and thereby modulate signaling by members of the TGFβ superfamily, including TGFβ and BMPs.

The invention further provides methods for screening candidate compounds to identify those able to modulate signaling by a member of the TGFβ superfamily through a pathway involving a SARA protein.

For example, the invention provides screening methods for compounds able to bind to a SARA protein which are therefore candidates for modifying the activity of the SARA protein. Various suitable screening methods are known to those in the art, including immobilization of a SARA protein on a substrate and exposure of the bound SARA protein to candidate compounds, followed by elution of compounds which have bound to the SARA protein. The methods used to characterise the binding interactions of the SARA proteins disclosed herein, as fully described in the examples herein, may also be used to screen for compounds which are agonists or antagonists of the binding of a SARA protein.

This invention also provides methods of screening for compounds which modulate TGFβ superfamily signaling by detecting an alteration in the phosphorylation state of a SARA protein.

In accordance with a further embodiment, the invention provides a method for reducing or preventing TGFβ, activin or BMP signaling by inhibiting the activity of SARA. SARA activity may be inhibited by use of an antisense sequence to the SARA gene or by mutation of the SARA gene.

SUMMARY OF THE DRAWINGS

Certain embodiments of the invention are described, reference being made to the accompanying drawings, wherein:

FIG. 3: Transfected cells were metabolically labelled with [$^{32}$P]PO$_4$ and cell lysates subjected to immunoprecipitation with anti-Flag antibodies for visualization of hSARA1 phosphorylation (top panel) or with anti-Myc antibodies for Smad2 phosphorylation (middle panel). Immunoprecipitates were resolved by SDS-PAGE and visualized by autoradiography. The migrations of hSARA1 and Smad2 are indicated.

FIG. 4: Lysates from transiently transfected COS cells were subjected to immunoprecipitation with anti-Flag antibodies and Smad2 bound to hSARA1 was analyzed by immunoblotting with anti-Myc antibodies (IP: α-flag; blot: α-Myc).

FIG. 5: Lysates from transiently transfected COS cells were subjected to immunoprecipitation with anti-Flag antibodies and Smad2 bound to hSARA1 was analyzed by immunoblotting with anti-Myc antibodies (IP: α-flag, blot: α-Myc). Partial dissociation of hSARA1/Smad2 complexes induced by TGFβ signaling was enhanced by expression of Smad4.

FIG. 6: Cell lysates from transiently transfected COS cells were subjected to immunoprecipitation with anti-Flag antibodies directed towards Smad2. Immunoprecipitates were then immunoblotted using anti-Myc or anti-HA antibodies which recognize hSARA1 or Smad4, respectively. Coprecipitating SARA (α-myc blot) and Smad4 (α-HA blot) are indicated.

Panels A, B, C, Mv1Lu cells singly transfected with hSARA1 (A) or Smad2 (B) are shown. Cotransfection of Smad2 with the constitutively active TβRI (TβRI*) results in its accumulation in the nucleus (C).

Panel D, Mv1Lu cells were transfected with hSARA1 and Smad2 and the localization of hSARA1 (red, left photo) and Smad2 (green, centre photo) is shown. Colocalization of SARA and Smad2 is shown (right photo) and appears as yellow.

Panel E, Mv1Lu cells were transfected with hSARA1, Smad2 and activated TβRI (TβRI*) and the localization of hSARA (red, left photo) and Smad2 (green, centre photo) is shown. Colocalization of SARA and Smad2 is indicated (right photo). Note the shift to an orangy-red colour in the punctate spots and an intensification of Smad2 nuclear staining, indicative of dissociation of Smad2 from SARA and nuclear translocation.

Figure 7:
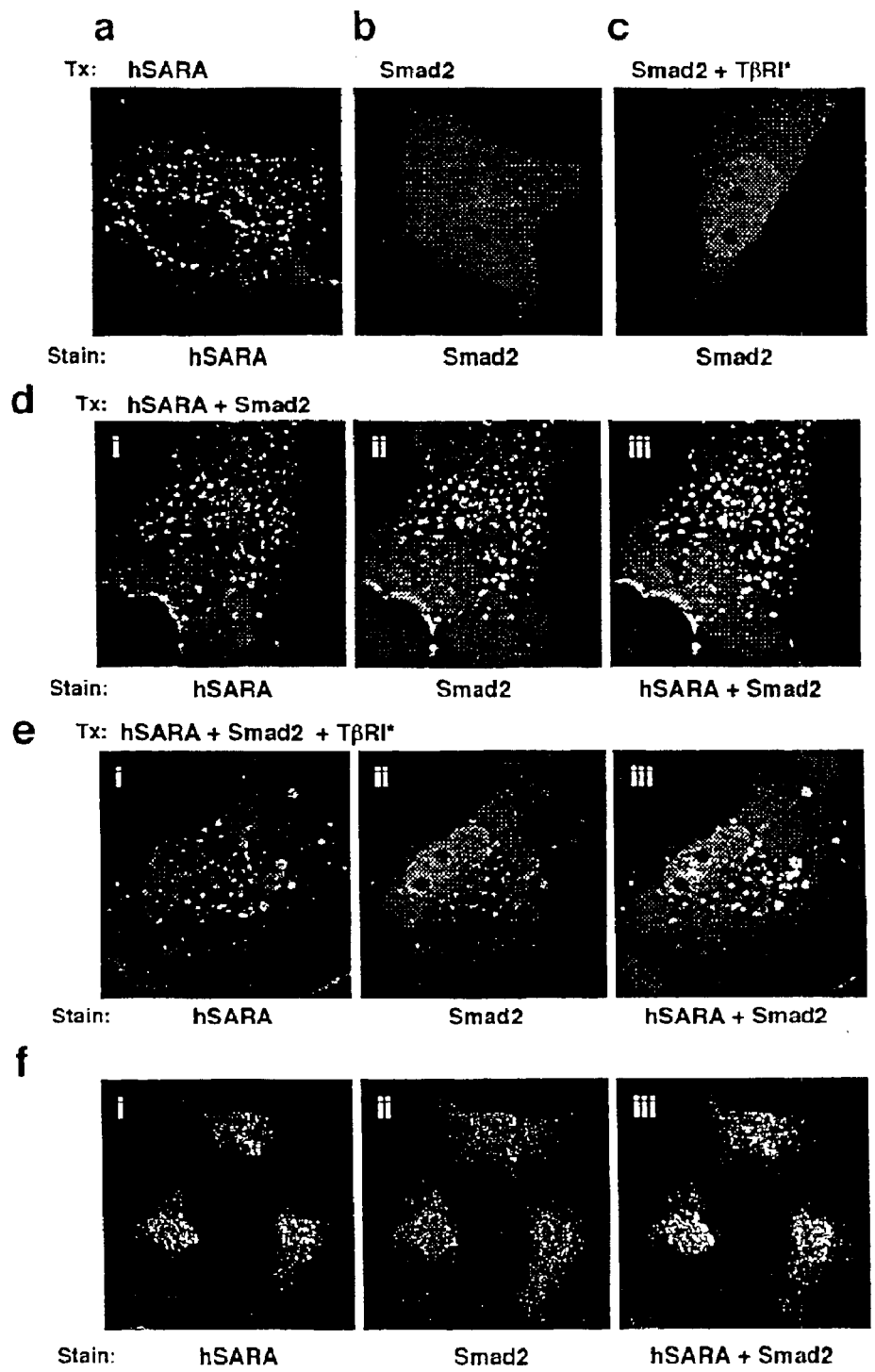
FIG. 7, panels A to E, shows photomicrographs of Mv1Lu cells transiently transfected with various combinations of Flag-Smad2, Myc-hSARA1, and constitutively active TβRI (TβRI*) as indicated (Tx). hSARA was visualized with the polyclonal Myc A14 antibody and Texas-Red conjugated goat-anti-rabbit IgG (red) and Smad2 was detected with an anti-Flag M2 monoclonal antibody followed by FITC-conjugated goat anti-mouse IgG (green). The subcellular localization of the expressed proteins was visualized by immunofluorescence and confocal microscopy.

FIG. 7, panel F, shows photomicrographs of Mv1Lu cells stained with rabbit, polyclonal anti-SARA antibody (left photo, green), goat, polyclonal anti-Smad 2/3 antibody (centre photo, red) and with both antibodies (right photo, yellow), showing co-localization of hSARA1 and Smad2.

Figure 8A:
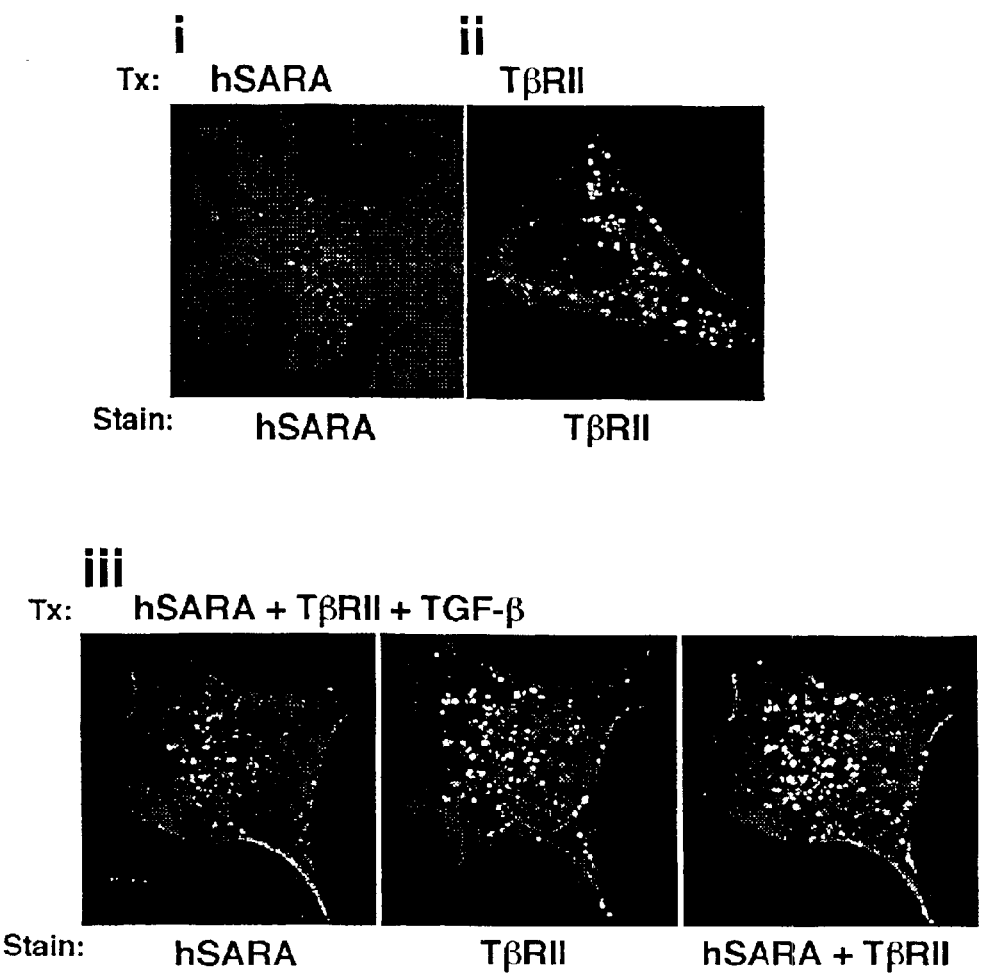

FIG. 8A shows photomicrographs of Mv1Lu cells transfected with either hSARA1 alone (panel i), TβRII alone (panel ii) or hSARA1 and TβRII together (panel iii), then treated with TGFβ and the localization of hSARA1 (red) and TβRII (green) determined by immunofluorescence and confocal microscopy. In cells coexpressing hSARA1 and TβRII, superimposing the staining revealed colocalization of the proteins as indicated by yellow staining in panel iii.

Figure 8B:
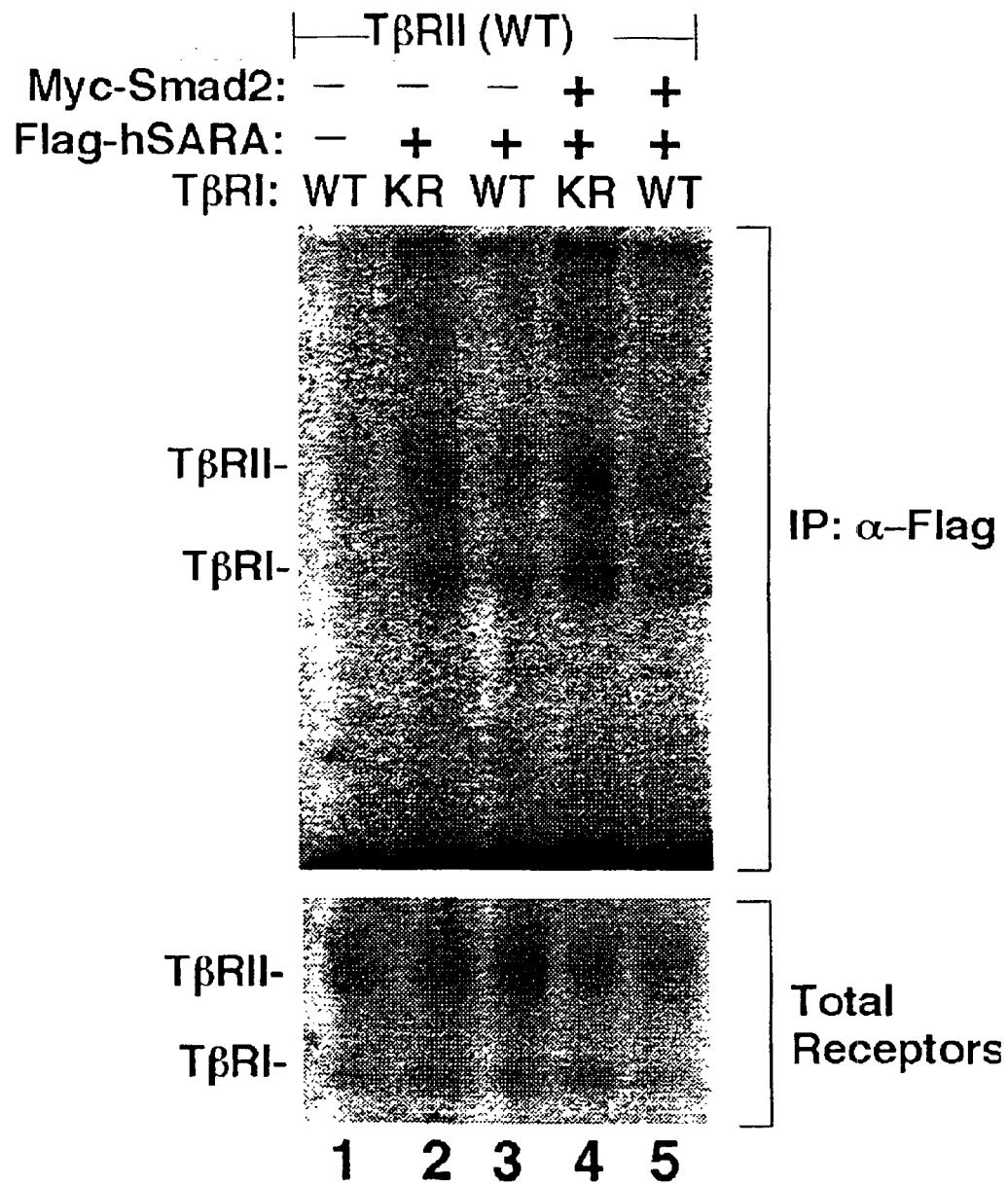

FIG. 8B shows affinity labelling of COS cells transiently transfected with various combinations of Flag-hSARA1, Myc-Smad2, wild type (WT) TβRII and either wild type or kinase-deficient (KR) versions of TβRI. Cells were affinity-labelled with [$^{125}$I]TGFβ and lysates immunoprecipitated with anti-Flag antibodies. Coprecipitating receptor complexes were visualized by SDS-PAGE and autoradiography. Equivalent receptor expression was confirmed by visualizing aliquots of total cell lysates (bottom panel).

Figure 9A:
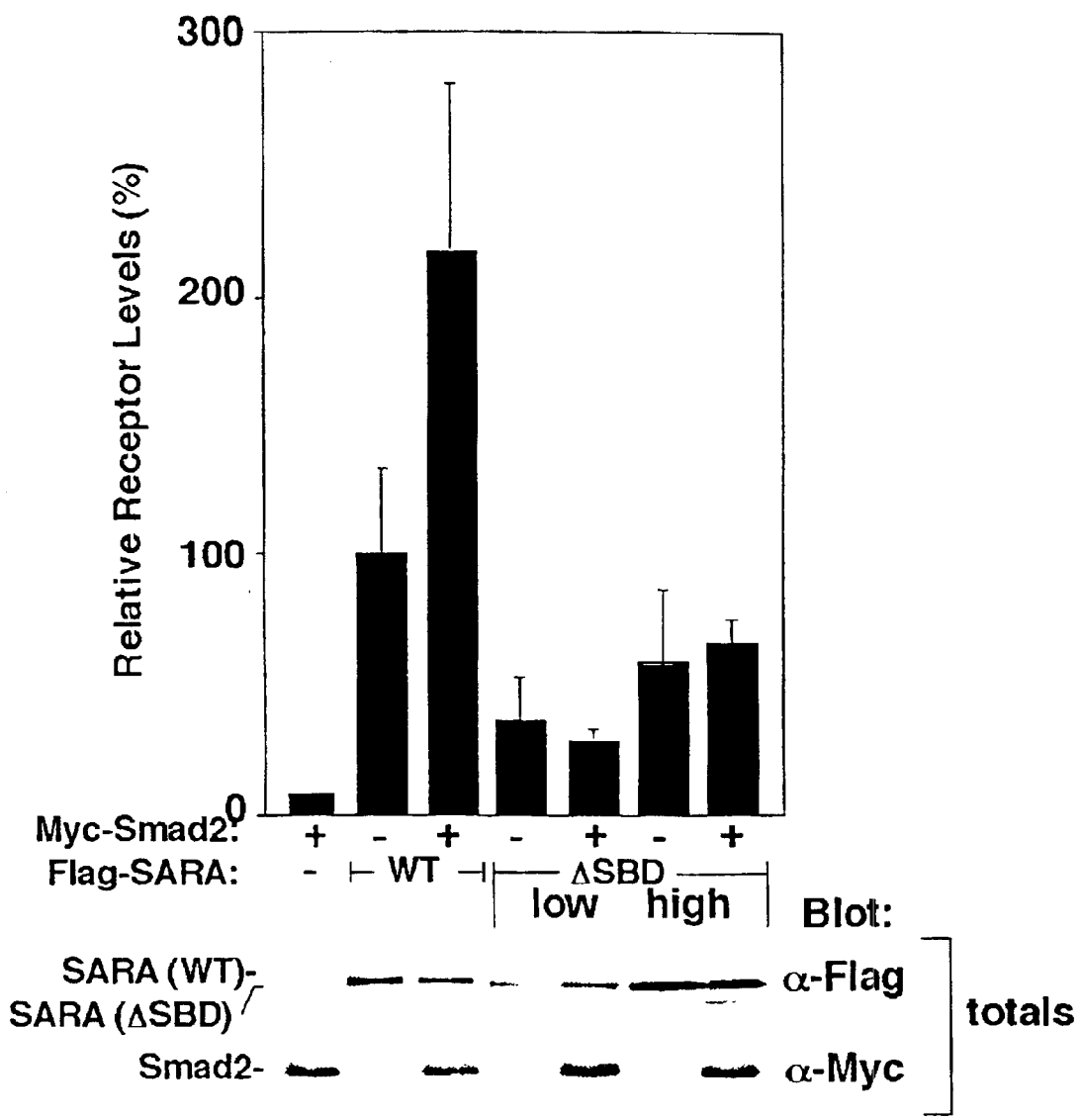

FIG. 9A shows COS cells transiently transfected with wild type TβRII and kinase deficient TβRI and various combinations of wild type Flag-hSARA1 (WT), a mutant version lacking the Smad2 binding domain (ΔSBD) and Myc-Smad2. The amount of receptor bound to SARA was determined by anti-Flag immunoprecipitation followed by gamma counting. Data is plotted as the average of three experiments±S.D. Protein expression was analyzed by immunoblotting aliquots of total cell lysates and the results from a representative experiment are shown (bottom panel).

Figure 9B:
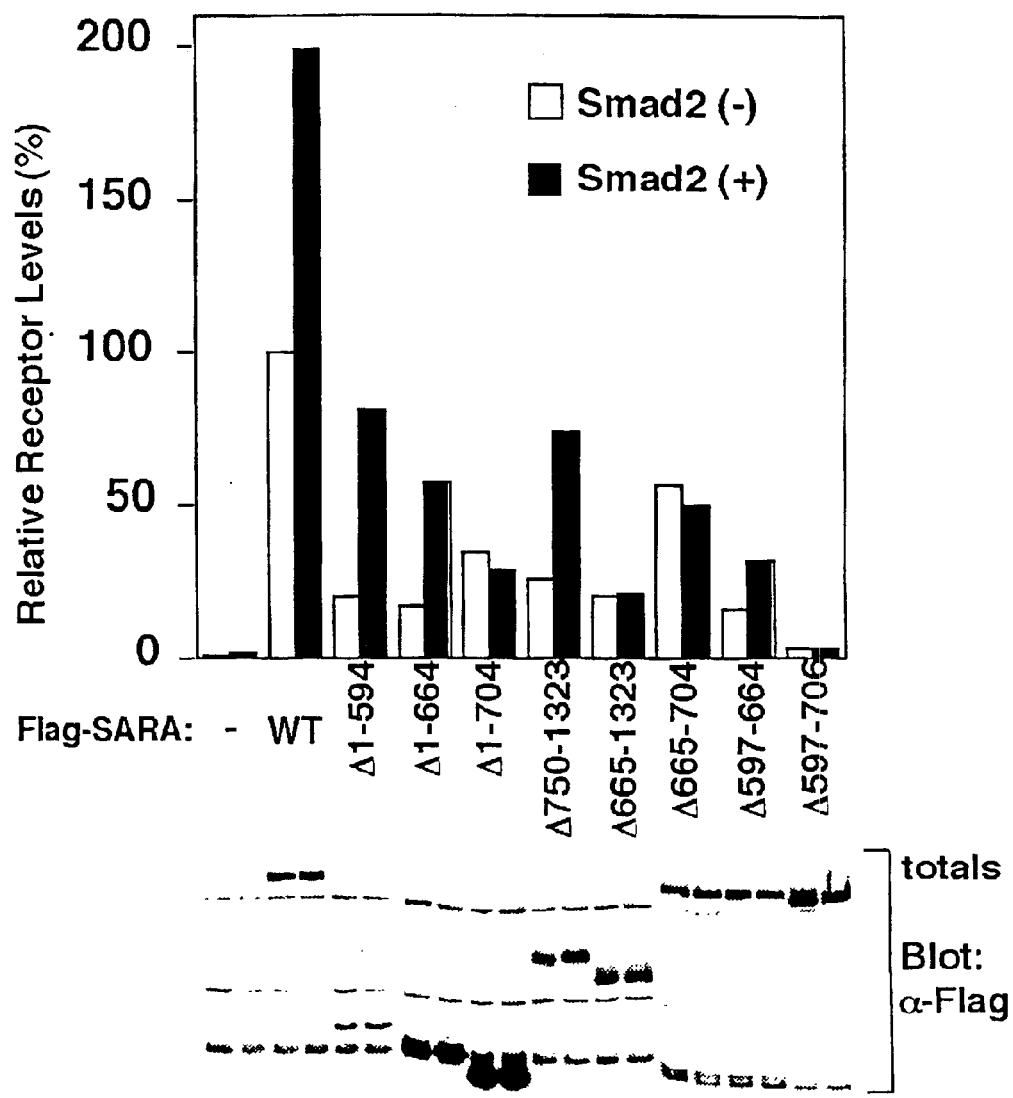

FIG. 9B shows COS cells transiently transfected with wild type TβRII and kinase-deficient TβRI and Flag-tagged wild type (WT) or mutant versions of hSARA1 with (black bars) or without (open bars) Myc-Smad2. The amount of receptor bound to hSARA1 was determined by anti-Flag immunoprecipitation followed by gamma counting. Protein expression was analyzed by immunoblotting aliquots of total cell lysates (bottom panel).

Figure 10:
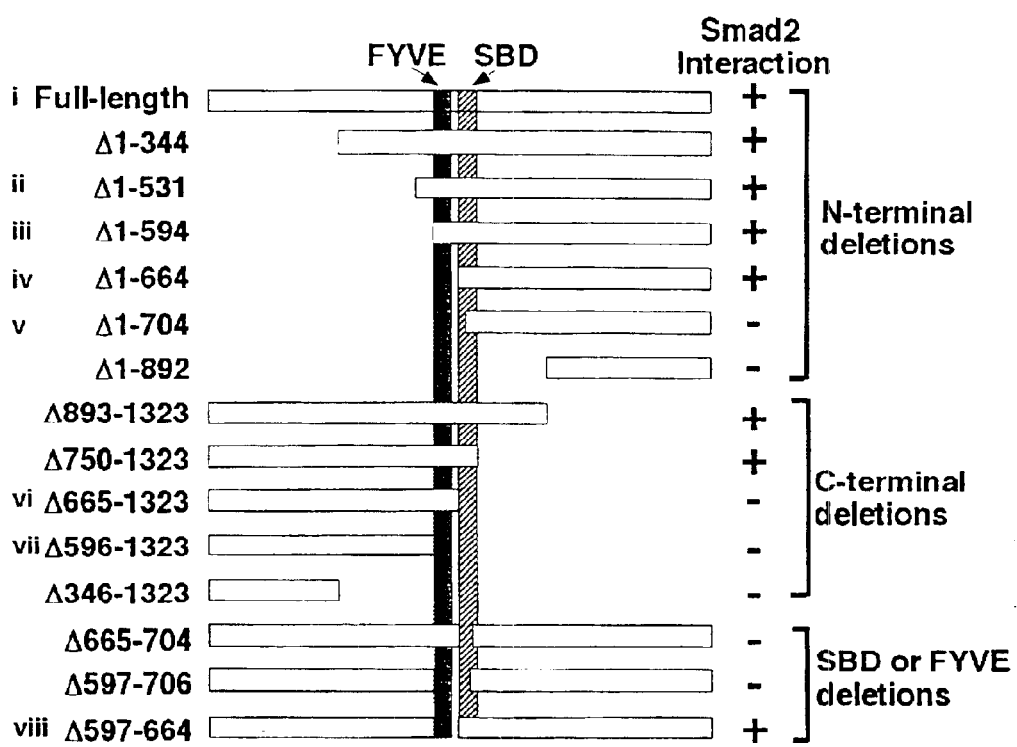

FIG. 10 is a schematic representation of mutant versions of SARA. The FYVE domain (shaded bar) and the Smad binding domain, SBD (striped bar), are indicated. COS cells transiently transfected with Flag-hSARA1 and Myc-Smad2 were immunoprecipitated with anti-Flag antibodies followed by immunoblotting with anti-Myc antibodies. The presence (+) or absence (−) of a hSARA1/Smad2 interaction is indicated (Smad2 interaction). Mutants used for the subsequent localization study are marked on the left (i–vi).

Figure 11A:
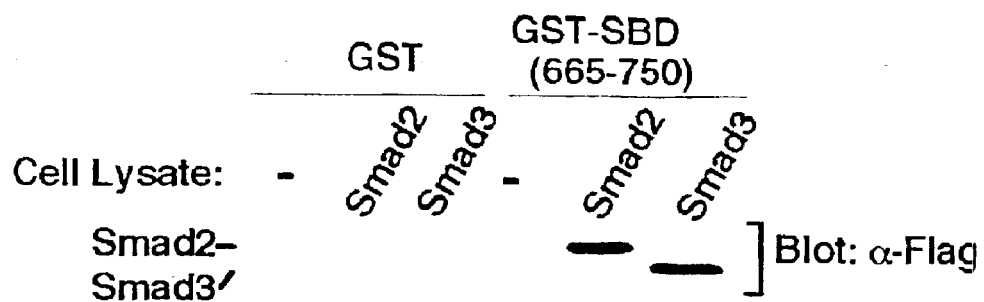

FIG. 11A shows an immunoblot of lysates from COS cells expressing Flag-tagged Smad2 or Smad3 incubated with GST alone or with GST-hSARA1 (665–750), which corresponds to the SBD; bound proteins were immunoblotted using anti-Flag antibodies. The presence of Smad2 and Smad3 bound to GST-hSARA1 (665–750) is indicated.

Figure 11B:
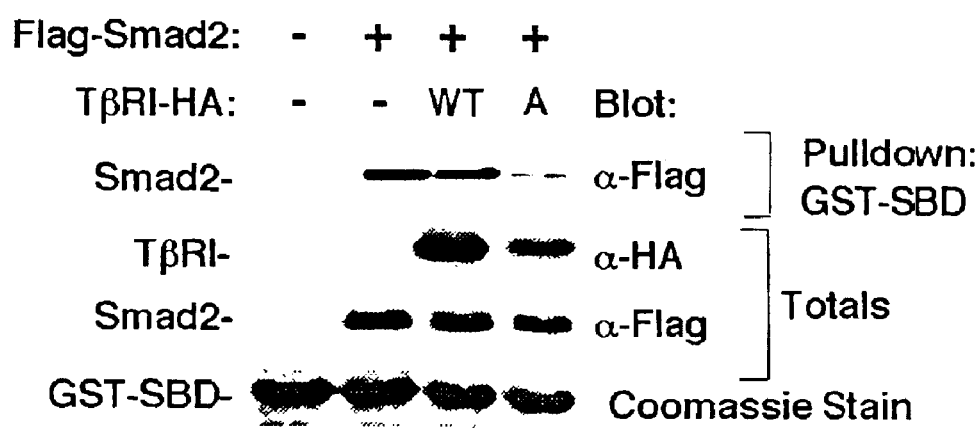

FIG. 11B shows an immunoblot of lysates, from COS cells expressing Flag-tagged Smad2 together with wild type (WT) or activated (A) type I receptor, incubated with GST-hSARA1 (665–750) (GST-SBD) and immunoblotted with anti-Flag antibodies. The expression levels of Smad2, each receptor and GST-hSARA1 (665–750) were determined by immunoblotting aliquots of total cell lysates.

Figure 12:
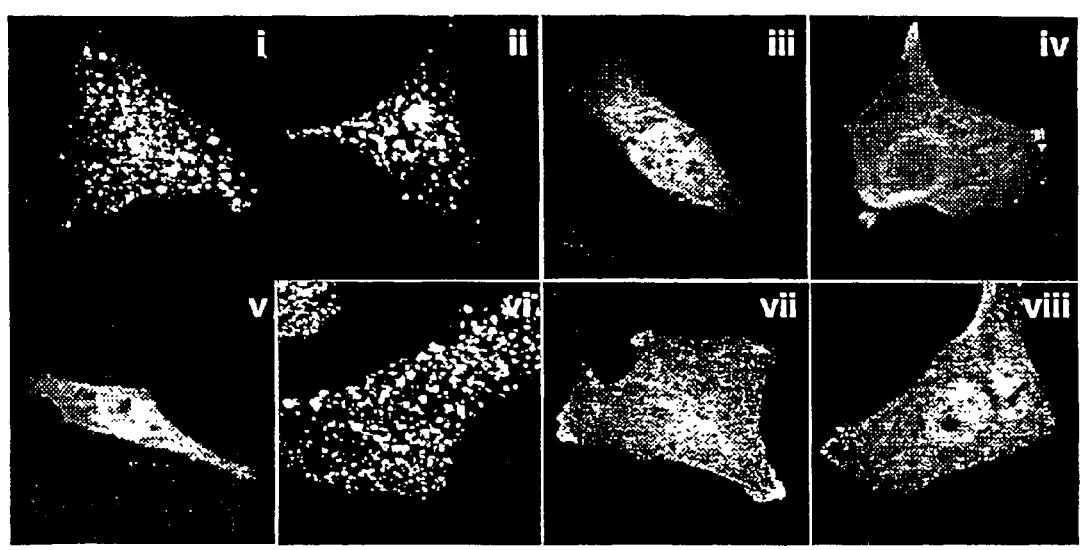

FIG. 12 shows the subcellular localization of hSARA1 mutants. Mv1Lu cells were transiently transfected with wild type (panel i) or mutant versions of Flag-hSARA1 (panels ii–viii, as marked on the left in FIG. 10). Proteins were visualized by immunofluorescence and confocal microscopy using a monoclonal anti-Flag M2 monoclonal antibody followed by FITC-conjugated goat anti-mouse IgG.

Figure 13:
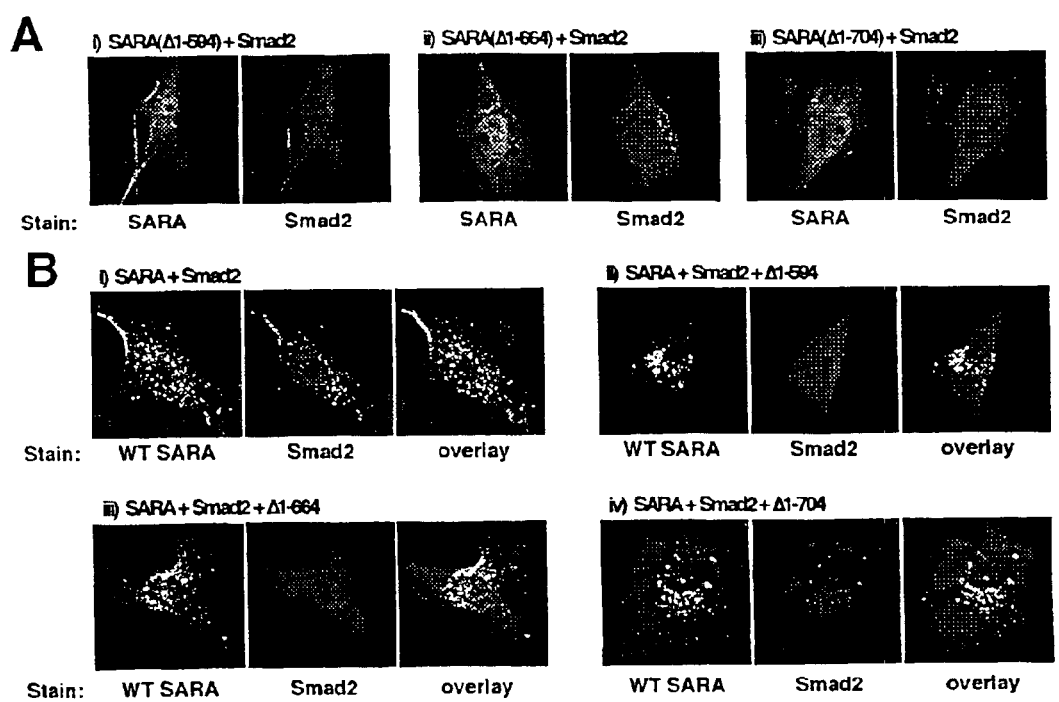

FIG. 13 shows photomicrographs of Mv1Lu cells transiently transfected with mutant versions of Myc-hSARA1 and Flag-Smad2 (panel A) or with wild type Myc-hSARA1, HA-Smad2 and mutant versions of hSARA1 (panel B). Protein subcellular localization was visualized by immunofluorescence and confocal microscopy. hSARA1 was visualized with the polyclonal Myc A14 antibody and FITC-conjugated goat anti-rabbit IgG (green), while Smad2 was detected with monoclonal antibodies followed by Texas Red-conjugated goat anti-mouse IgG (red). In B, overlaying the images reveals mislocalization of Smad2 as green speckles of SARA over red, diffuse Smad2 staining (panels ii and iii) and colocalization of hSARA1 and Smad2 appears as yellow spots (panels i and iv).

Figure 14:
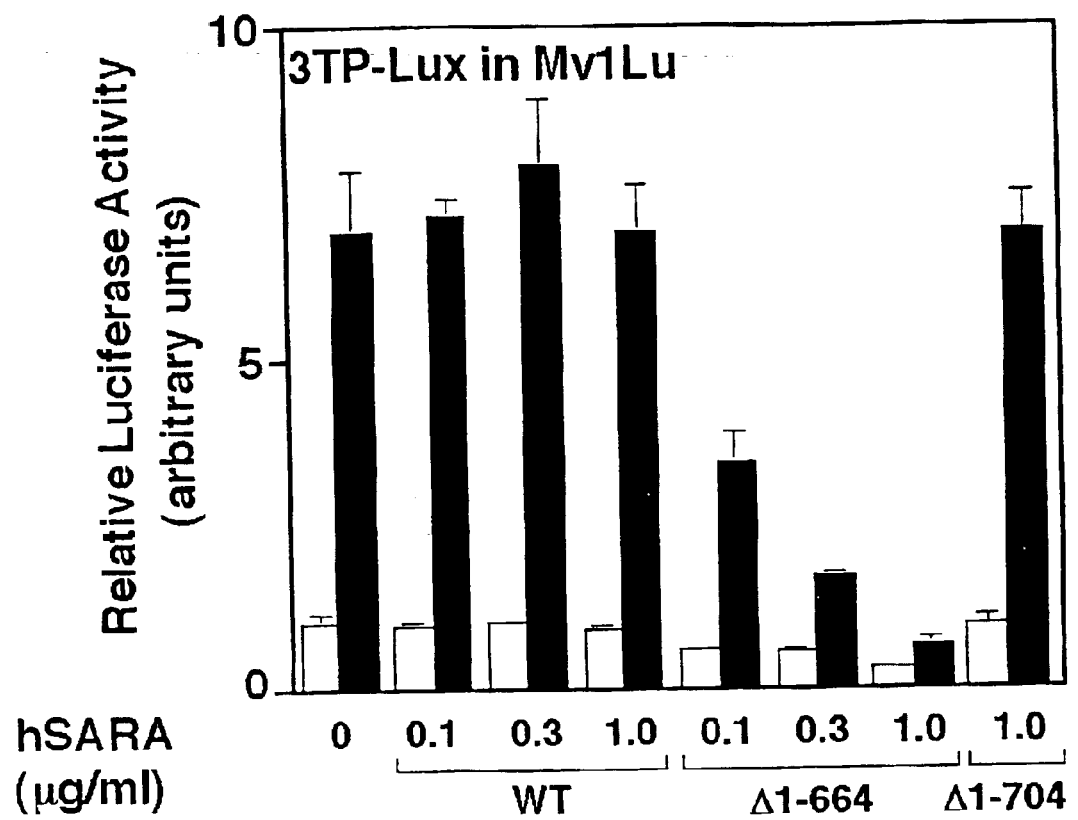

FIG. 14 shows luciferase activity of Mv1Lu cells transfected with 3TP-lux alone or together with the indicated amounts of wild type (WT) or mutant (Δ1–664 or Δ1–704) versions of hSARA1 and incubated in the presence (black bars) or absence (open bars) of TGFβ. Luciferase activity was normalized to β-galactosidase activity and is plotted as the mean±S.D. of triplicates from a representative experiment.

Figure 15:
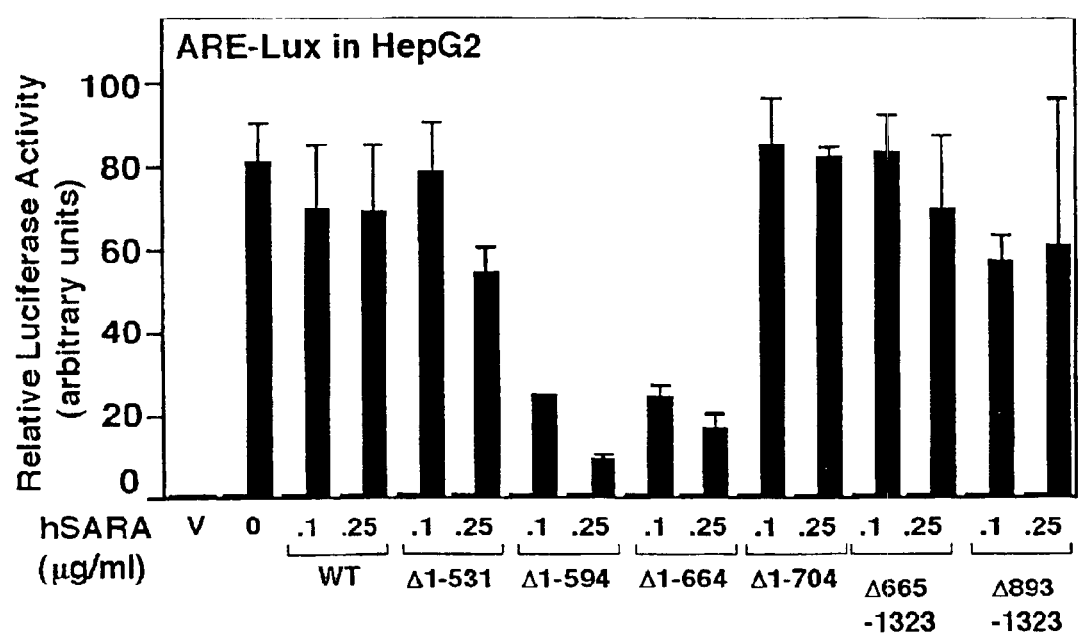

FIG. 15 shows luciferase activity of HepG2 cells transfected with ARE-Lux alone (v), or ARE-Lux and FAST2 alone or together with the indicated amounts of wild type (WT) or mutant versions of hSARA1. Transfected cells were incubated in the presence (black bars) or absence (open bars) of TGFβ and luciferase activity was normalized to β-galactosidase activity and is plotted as the mean±S.D. of triplicates from a representative experiment.

Figure 16:
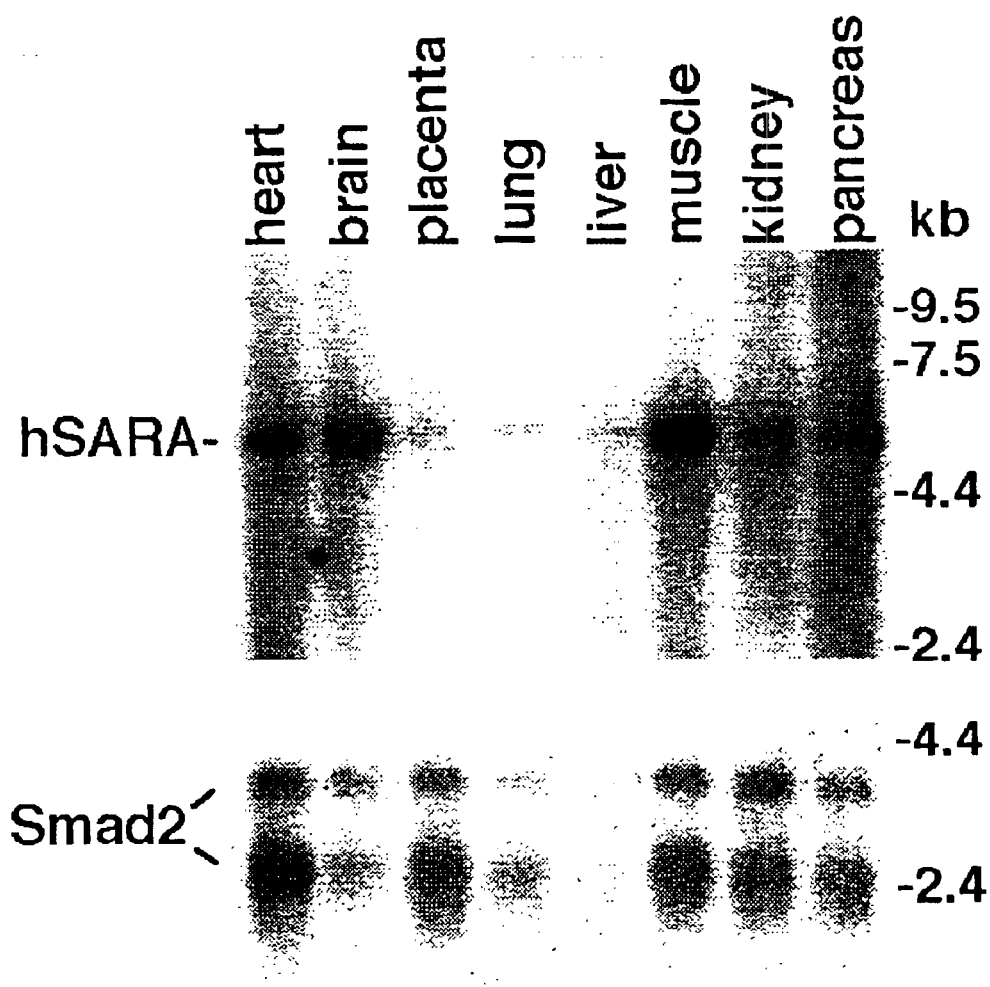

FIG. 16 shows a Northern blot of expression of hSARA1 (upper panel) and Smad2 (lower panel) in the indicated tissues.

Figure 17:
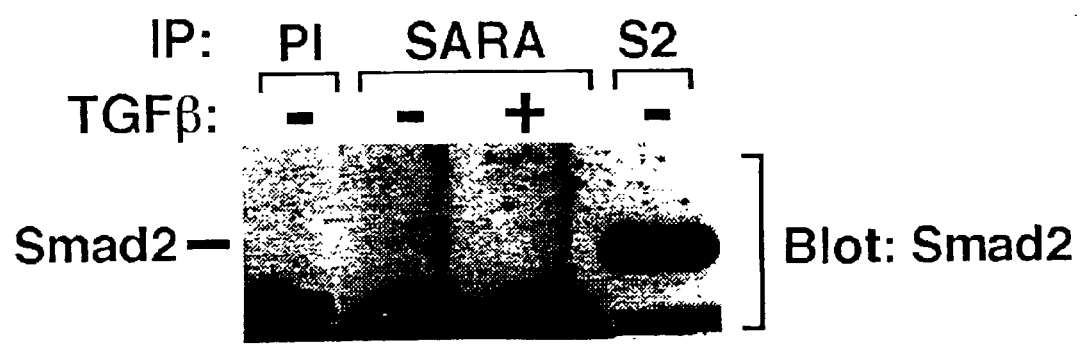

FIG. 17 shows an immunoblot of a HepG2 lysate immunoprecipitated (IP) with preimmune serum (PI), anti-hSARA1 polyclonal antibody (SARA) with and without pretreatment with TGFβ (− and +), or N19 anti-Smad2/3 antibody (S2), followed by immunoblotting with an anti-Smad2 antibody. The migration position of Smad2 is indicated (Smad2).

Figure 18:
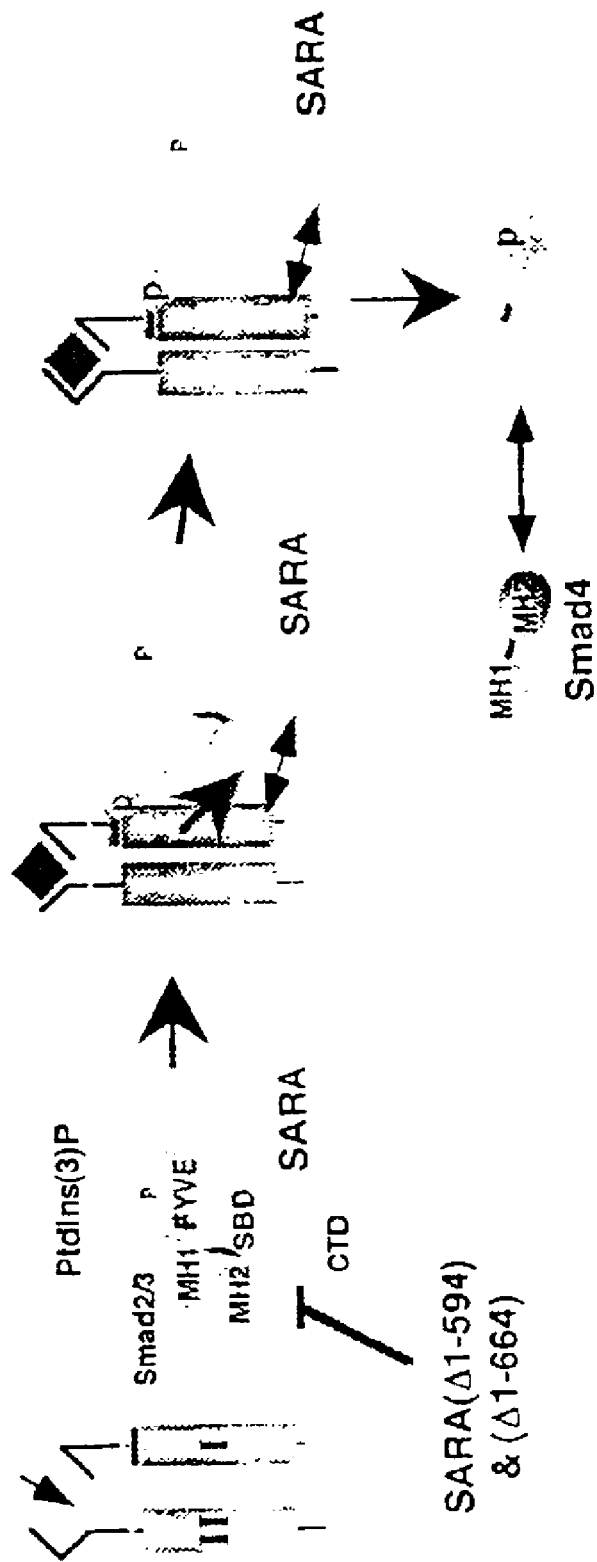

FIG. 18 shows a diagram of a model of the interaction of a SARA protein with a receptor regulated Smad, as exemplified by the interaction of hSARA1.

DETAILED DESCRIPTION OF THE INVENTION

This invention provides a family of proteins that play key roles in TGFβ, activin and bone morphogenetic protein (BMP) signal transduction pathways. In particular, the proteins of this family interact with specific Smad proteins to modulate signal transduction. These proteins are therefore designated as "Smad Anchor for Receptor Activation" or "SARA" proteins. SARA proteins are characterised by three distinct domains (1) a double zinc finger or FYVE domain responsible for the subcellular localization of the SARA protein or SARA-Smad complex, possibly through its association with PtdIns(3)P, (2) a Smad binding domain ("SBD") which mediates the interaction or binding of one or more species of Smad protein with the particular member of the SARA family and (3) a carboxy terminal domain which mediates interaction of SARA with members of the TGFβ superfamily of receptors.

FYVE domains have been identified in a number of unrelated signaling molecules that include FGD1, a putative guanine exchange factor for Rho/Rac that is mutated in faciogential dysplasia, the HGF receptor substrate Hrs-1 and its homolog Hrs-2, EEA1, a protein involved in formation of the early endosome and the yeast proteins FAB1, VPS27 and VAC1 (reviewed in Wiedemann and Cockcroft, 1998). Recently, analysis of a number of FYVE domains from yeast and mammals has revealed that this motif binds phosphatidyl inositol-3-phosphate (PtdIns(3)P) with high specificity and thus represents a novel signaling module that can mediate protein interaction with membranes (Burd and Emr, 1998; Gaullier et al., 1998; Patki et al., 1998; Simonsen et al., 1998; Wiedemann and Cockcroft, 1998). Comparison of the FYVE domains from the vertebrate proteins with that from SARA revealed extensive conservation of residues throughout the domain (Table 10). Thus, SARA contains a FYVE domain that may function to bind PtdIns(3)P, which has been implicated in intracellular vesicle transport.

For example, deletion of the FYVE domain in hSARA1 causes mislocalization of Smad2 or Smad3, interferes with TGFβ receptor interaction and inhibits TGFβ-dependent transcriptional responses.

Thus, the SARA proteins of the invention define a component of TGFβ superfamily signaling that fulfills an essential role in anchoring receptor regulated Smads to specific subcellular domains for activation by a TGFβ superfamily receptor.

Cloned DNA coding sequences and corresponding amino acid sequences for representative human and *Xenopus* SARA protein family members are shown in the Tables, as follows:

Tables 1 and 2—human SARA1 (hSARA1) cDNA (Sequence ID NO:1) and amino acid sequence (Sequence ID NO:2) respectively;

Tables 3 and 4—human SARA2 (hSARA2) cDNA (Sequence ID NO:3) and amino acid sequence (Sequence ID NO:4) respectively;

Tables 5 and 6—*Xenopus* SARA1 (XSARA1) cDNA (Sequence ID NO:5) and amino acid sequence (Sequence ID NO:6) respectively; and Tables 7 and 8—*Xenopus* SARA2 (XSARA2) cDNA (Sequence ID NO:7) and amino acid sequence (Sequence ID NO:8) respectively.

Table 9 shows a comparison of the amino acid sequences of XSARA1 and hSARA1. Identical residues (dark grey) and conservative changes (light grey), the FYVE domain (solid underline) and the Smad binding domain (dashed underline) are indicated. The sequences in XSARA1 used to design degenerate PCR primers for identifying hSARA1 are shown (arrows). The amino-terminal end of the partial *Xenopus* cDNA obtained in the expression screen is marked (asterisk).

The human SARA of Tables 1 and 2, identified as described in Example 2, regulates the subcellular localization of Smad2 and Smad3 and recruits these Smads into distinct subcellular domains. This SARA also interacts with TGFβ receptors and TGFβ signaling induces dissociation of Smad2 or Smad3 from the SARA protein with concomitant formation of Smad2/Smad4 complexes and nuclear translocation.

Table 10 shows alignment of the amino acid sequences of the FYVE domains from hSARA1, XSARA1, KIAA0305, FGD1, Hrs-1, Hrs-2 and EEA1. Identical residues (dark grey) and conservative changes (light grey) are marked. A consensus sequence (bottom) was derived from positions in which at least 6 out of 7 residues were conserved or when proteins contained one of only two alternate residues.

The regulation of the subcellular localization of components of signaling pathways can be key determinants in the effective initiation and maintenance of signaling cascades. Targeting of signal transduction proteins to specific subcellular regions is highly regulated, often through specific interactions with scaffolding or anchoring proteins (Faux and Scott, 1996; Pawson and Scott, 1997). Scaffolding proteins have been defined as proteins that bind to multiple kinases to coordinate the assembly of a cascade, while anchoring proteins are tethered to specific subcellular regions in the cell and can act to bring together components of a pathway. Regulating location of signaling components can thus coordinate the activity of a signaling network, maintain signaling specificity or facilitate activation of a pathway by localizing kinases together with their downstream substrates.

As described herein, a recombinantly produced human SARA protein bound directly and specifically to unphosphorylated Smad2 and Smad3. In addition, receptor-dependent phosphorylation induced Smad2 to dissociate from SARA, bind to Smad4 and translocate to the nucleus. Thus, the hSARA1 protein functions in TGFβ signaling upstream of Smad activation to recruit Smad2 to the TGFβ receptor by mediating the specific subcellular localization of Smad and by associating with the TGFβ receptor complex. Furthermore, inducing mislocalization of Smad2 by expressing a mutant of the hSARA1 protein blocks TGFβ-dependent transcriptional responses, indicating an essential role for SARA-mediated localization of Smads in signaling. Together, these results identify the cloned hSARA1 protein as a novel component of the TGFβ pathway that functions to anchor Smad2 to specific subcellular sites for activation by the TGFβ receptor kinase.

In vitro, receptor-regulated Smads are recognized by the receptor kinases and are phosphorylated on the C-terminal SSXS motif (Abdollah et al., 1997; Kretzschmar et al., 1997; Macias-Silva et al., 1996; Souchelnytskyi et al., 1997). This phosphorylation is similar to receptor-dependent phosphorylation in mammalian cells, suggesting that SARA is not absolutely required for recognition of Smads by the receptor complex. In intact cells, however, receptor-regulated Smads are cytosolic proteins that require activation by transmembrane serine/threonine kinase receptors. Consequently, Smads may require recruitment by SARA to interact with TGFβ superfamily receptors. Domains in which SARA is found correspond to regions where TGFβ receptors are also localised. TGFβ receptors display regionalized localization and hSARA1 recruits Smad2 to these domains. The identity of these intracellular domains is unclear. However, they contain receptors and recent evidence has shown that FYVE finger domains interact with membranes, so it is reasonable to suggest that these domains represent membrane vesicles. Thus, clustering of the TGFβ receptor, as previously described by Henis et al. (1994), may function to direct the receptor to hSARA1 and the Smad2 substrate. This activity may be most critical in vivo, where ser/thr kinase receptors are often found in low numbers and only a small proportion need to be activated for biological responses (Dyson and Gurdon, 1998). This activity is likely to be most critical in vivo, where ser/thr kinase receptors are often found in low numbers and only a small proportion need to be activated for biological responses (Dyson and Gurdon, 1998). This may impose on the pathway a stringent requirement for SARA to anchor Smads in these sites for receptor interaction.

The colocalization and association of hSARA1 with the TGFβ receptor defines a role for hSARA1 in recruiting Smad2 to the receptor kinase. Furthermore, deletion of the FYVE domain interferes with receptor binding, prevents the correct localization of hSARA1/Smad2 and blocks TGFβ signaling (see Example 8 below), suggesting that this is an important function in the pathway. Interestingly, the binding of the hSARA1 protein identified in Example 2 to the receptor was enhanced upon Smad2 expression and, on its own, SARA may interact inefficiently with the receptor. However, within the hSARA1/Smad complex, Smad2 might help drive association with the receptor through its recognition of the catalytic region of the kinase domain. Consistent with this, cooperation requires a kinase deficient type I receptor which also traps the Smad2 substrate (Macias-Silva et al., 1996). Thus, Smad2 may bind to the catalytic pocket of the type I kinase domain while hSARA1, which is not a substrate of the kinase, may interact with regions outside of the domain.

The human SARA protein identified in Example 2 did not interact with any of the other Smads tested, indicating that it functions specifically in Smad2 and Smad3 pathways (see Example 3). However, Smad5 localization in 293 cells displayed a remarkably similar pattern to that of this SARA protein (Nishimura et al., 1998) and similar patterns were observed for endogenous Smad1 or 5 in the kidney epithelial cell line, IMCD-3. Thus, localization of BMP-regulated Smads (for example, Smad1, Smad5 and Smad8) may also be regulated by a specific SARA family member.

The genes for two other SARA family member proteins were also identified and cloned. One of these, identified in *Xenopus* and designated XSARA2 (Tables 7 and 8), is related to XSARA1, while the other one, hSARA2 (Tables 3 and 4), is a human clone, related to the hSARA1 of Tables 1 and 2. This second human clone has been identified in EST clone KIAA0305. A comparison of the SBD from hSARA1 with a similar region from the KIAA0305 sequence indicated that the amino terminal half of the region of the SBD was highly divergent from the amino acid sequence encoded by KIAA0305. This suggests that the protein encoded by KIAA0305 may mediate binding with other as yet unidentified proteins, eg. other Smads. In contrast to the SBD, the FYVE domain of the KIAA0305 protein is more closely related to the hSARA1 FYVE domain (70% identity), suggesting that this protein may be an anchor for other Smad proteins that function either in the TGFβ pathway or in other signaling cascades, such as the BMP signal transduction pathway.

SARA is not Limiting in Smad Activation and TGFβ Superfamily Signaling

It was observed that elevating Smad2 levels can saturate hSARA1 and yield a diffuse distribution for Smad2. Thus, the level of the hSARA1 protein is a key determinant in controlling Smad2 localization. As a consequence, endogenous Smad2 may or may not display a hSARA1-like distribution, depending on the relative expression of the two proteins. Indeed, in Mv1Lu cells, endogenous Smad2 displays a punctate pattern with somne diffuse staining in the cytosol. While not meaning to limit the invention to a particular mechanism, the data are consistent with the view that once signaling has commenced, Smad2 dissociates from hSARA1, binds to Smad4 and translocates to the nucleus, freeing hSARA1 to recruit additional Smad2 from the cytosolic reservoir. This would provide a mechanism to allow quantitative activation of Smads in the presence of high levels of TGFβ signaling.

By functioning to recruit Smad2 to the TGFβ receptor, hSARA1 is located in an important regulatory position in the pathway. Thus, control of hSARA1 localization or protein levels, or its interaction with Smad2, could modulate TGFβ signaling. Further, disruption of normal hSARA1 function could potentially be involved in loss of TGFβ responsiveness that is a common feature during tumour progression.

Modular Domains in SARA

The function of hSARA1 in TGFβ signaling is mediated by three independent domains, the Smad binding domain (SBD) that mediates specific interaction with Smad2 and Smad3, the FYVE domain that targets hSARA1/Smad2 to specific subcellular sites and the carboxy terminus which mediates association with the TGFβ receptor. The *Xenopus* and mouse forkhead-containing DNA binding proteins, FAST1 and FAST2, bind specifically to Smad2 and Smad3 and like hSARA1, interact with the MH2 domains (Chen et al., 1996; Chen et at., 1997a; Labbé et al., 1998; Liu et al., 1997a). Comparison of the SBD from this SARA with the Smad Interaction Domain (SID) from these FAST proteins revealed no regions of obvious similarity. However, since hSARA1 acts upstream and FAST downstream of Smad activation, these proteins may employ structurally unrelated domains to distinguish unactivated versus activated forms of Smad2. Thus, the SBD of this SARA protein preferentially binds unphosphorylated monomeric Smad2 while the SID from FAST must bind phosphorylated Smad2 in heteromeric complexes with Smad4. By analogy, the SBD of other SARA family members may bind the unphosphorylated monomeric species of other Smads that mediate signal transduction in other pathways (eg. Smads 1, 5 or 8 in the BMP signal transduction pathway).

In hSARA1, the FYVE domain functions independently of the SBD, to mediate the subcellular targetting of the protein. The FYVE-finger motif has now been identified in at least 30 proteins from diverse species, such as FGD1, Hrs-1 and 2, and EEA1 (Gaullier et al., 1998; Wiedemann and Cockcroft, 1998). Recent advances have demonstrated that FYVE finger motifs from a variety of divergent proteins have a conserved function and bind phosphatidyl inositol-3-phosphate (Ptdlns(3)P) with high specificity (Burd et al., (1998); Patki (1998); Gaullier (1998)). Through this interaction, the FYVE finger can mediate protein interactions with phospholipid bilayers. However, Ptdlns(3)P is present ubiquitously on cell membranes and in the case of EEA1, further protein—protein interactions with Rab5-GTP are required in addition to the FYVE domain to target the protein to the correct membranes (Simonsen et al., 1998). Given that PtdIns(3)P binding by FYVE fingers is conserved in yeast and mammals, it is likely that the FYVE finger of hSARA1 similarly mediates interaction with the membrane. Furthermore, it is possible that additional protein—protein interactions may be required to direct hSARA1 to regions that contain the TGFβ receptors. The carboxy terminus of hSARA1, which is required for efficient interaction with the TGFβ receptor, may function in this capacity.

Together, these data define discrete domains in SARA that fulfill specific aspects of SARA function in TGFβ superfamily signaling. Without being limited to any particular mechanism, a possible model of the interaction of SARA with a receptor regulated Smad in TGFβ superfamily signaling, as exemplified by hSARA1 and its interactions with Smad2 in TGFβ signaling, is shown diagrammatically in FIG. 18. The FYVE domain likely functions to direct SARA to the membrane, perhaps through interactions with PtIns(3)P. It thus fulfills an important role in recruiting hSARA1 to specific subcellular domains that have been shown also to contain the TGFβ receptor. The SBD in turn functions to bind unactivated Smad2, thus recruiting the receptor substrate to this subcellular region. Once localized to this region, the C-terminal domain of hSARA1 functions with Smad2 bound to the SBD to promote interaction with the receptor complex. These three domains thus function cooperatively to recruit Smad2 to the TGFβ receptor.

Additional Roles for SARA

Controlling the localization of kinases and their substrates may allow not only for efficient recognition and phosphorylation but may also function to maintain specificity and suppress crosstalk between signaling pathways. Thus, by controlling Smad localization, a SARA family member protein could additionally function to maintain the highly specific regulation of Smad phosphorylation by ser/thr kinase receptors that is observed in vivo and could prevent promiscuous phosphorylation by other kinases in the cell. Furthermore, through its interactions with a particular receptor, a SARA protein might function to control the activity or turnover of the receptor complex. Alternatively, SARA may also fulfill scaffolding functions to coordinate the receptor-dependent activation of Smads with other as yet unidentified components of a signaling pathway.

Nucleic Acids

In accordance with one series of embodiments, the present invention provides isolated nucleic acids corresponding to, or related to, the human and *Xenopus* SARA nucleic acid sequences disclosed herein. In addition to the SARA nucleotide sequences disclosed herein, one of ordinary skill in the art is now enabled to identify and isolate homologues of the SARA genes described herein. One of ordinary skill in the art may screen preparations of genomic or cDNA from other species using probes or PCR primers derived from nucleotide sequences disclosed herein. In accordance with a further embodiment, the invention provides isolated nucleic acids of at least 10 consecutive nucleotides, preferably 15 consecutive nucleotides, more preferably 20 consecutive nucleotides of Sequences ID NO:1, Sequence ID NO:3, Sequence ID NO:5 and Sequence ID NO:7, up to the complete sequences. Short stretches of nucleotide sequence are useful as probes or primers useful for identification or amplification of the nucleic acids of the invention or for encoding fragments, functional domains or antigenic determinants of SARA proteins.

The invention also includes polynucleolides which are complementary to the disclosed sequences, polynucleotides which hybridise to these sequences at high stringency and degeneracy equivalents of these sequences.

Proteins

SARA proteins may be produced by culturing a host cell transformed with a DNA sequence encoding a selected SARA protein. The DNA sequence is operatively linked to an expression control sequence in a recombinant vector so that the protein may be expressed.

Host cells which may be transfected with the vectors of the invention may be selected from the group consisting of *E. coli, Pseudomonas, Bacillus subtillus*, or other *bacilli*, yeasts, fungi, insect cells or mammalian cells including human cells.

For transformation of a mammalian cell for expression of a SARA protein, the vector may be delivered to the cells by a suitable vehicle. Such vehicles including vaccinia virus, adenovirus, retrovirus, Herpes simplex virus and other vector systems known to those of skill in the art.

A SARA protein may also be recombinantly expressed as a fusion protein. For example, the SARA cDNA sequence is inserted into a vector which contains a nucleotide sequence encoding another peptide (e.g. GST-glutathione succinyl transferase). The fusion protein is expressed and recovered from prokaryotic (e.g. bacterial or baculovirus) or eukaryotic cells. The fusion protein can then be purified by affinity chromatography based upon the fusion vector sequence and the SARA protein obtained by enzymatic cleavage of the fusion protein.

The protein may also be produced by conventional chemical synthetic methods, as understood by those skilled in the art.

SARA proteins may also be isolated from cells or tissues, including mammalian cells or tissues, in which the protein is normnally expressed.

The protein may be purified by conventional purification methods known to those in the art, such as chromatography methods, high performance liquid chromatography methods or precipitation.

For example, anti-SARA antibodies may be used to isolate SARA protein which is then purified by standard methods.

Antibodies

The provision of the polynucleotide and amino acid sequences of SARA proteins provides for the production of antibodies which bind selectivety to a SARA protein or to fragments thereof. The term "antibodies" includes polyclonal antibodies, monoclonal antibodies, single chain antibodies and fragments thereof such as Fab fragments.

In order to prepare polyclonal antibodies, fusion proteins containing defined portions or all of a SARA protein can be synthesized in bacteria by expression of the corresponding DNA sequences, as described above. Fusion proteins are commonly used as a source of antigen for producing antibodies. Alternatively, the protein may be isolated and purified from the recombinant expression culture and used as source of antigen. Either the entire protein or fragments thereof can be used as a source of antigen to produce antibodies.

The purified protein is mixed with Freund's adjuvant and injected into rabbits or other appropriate laboratory animals. Following booster injections at weekly intervals, the animals are then bled and the serum isolated. The serum may be used directly or purified by various methods including affinity chromatography to give polyclonal antibodies.

Alternatively, synthetic peptides can be made corresponding to antigenic portions of a SARA protein and these may be used to inoculate the animals.

In a further embodiment, monoclonal anti-SARA antibodies may be produced by methods well known in the art. Briefly, the purified protein or fragment thereof is injected in Freund's adjuvant into mice over a suitable period of time, spleen cells are harvested and these are fused with a permanently growing myeloma partner and the resultant hybridomas are screened to identify cells producing the desired antibody. Suitable methods for antibody preparation may be found in standard texts such as Antibody Engineering, 2d. edition, Barreback, E D., Oxford University Press, (1995).

Transgenic Animals

In accordance with a further embodiment, the invention provides for the production of transgenic non-human animals which afford models for further study of the SARA family of proteins and also provide tools for the screening of the candidate compounds as therapeutics.

Animal species which are suitable for use include rats, mice, hamsters, guinea pigs, rabbits, dogs, cats, goats, sheep, pigs and non-human primates.

In accordance with one embodiment, a transgenic animal may be prepared carrying a heterologous SARA gene by inserting the gene into a germ line or stem cell using standard technique of oocyte microinjection, or transfection or microinjection into embryonic stem cells. The techniques of generating transgenic animals are now well known and fully described in the literature. For example, a laboratory manual in the manipulation of the mouse embryo describes standard laboratory techniques for the production of transgenic mice (Hogan et al. (1986), Manipulating the Mouse Embryo, Cold Spring Harbour Laboratory Press, Cold Spring Harbour, N.Y.).

In accordance with a further embodiment, the invention enables the inactivation or replacement of an endogenous SARA gene in an animal by homologous recombination. Such techniques are also fully described in the literature. Such techniques produce "knock-out" animals, with an inactivated gene, or "knock-in" animals, with a replaced gene.

EXAMPLES

The examples are described for the purposes of illustration and are not intended to limit in any way the scope of the invention.

Methods of molecular genetics, protein and peptide biochemistry and immunology referred to but not explicitly described in this disclosure and examples are reported in the scientific literature and are well known to those skilled in the art.

Example 1

Methods

Isolation of *Xenopus* and human SARA

To prepare a probe for library screening, the MH2 domain of Smad2 (amino acids 241–467) was subcloned into a modified pGEX4T-1 vector containing the protein kinase A recognition site derived from pGEX2TK (Pharmacia). This bacterial fusion protein was purified, labelled with [$^{32}$P] γATP and used as probe to screen a λZAP II *Xenopus* dorsal lip library as described (Chen and Sudol, 1995). A screen of 1×10$^6$ plaques yielded four phage which represented repeated isolates of the same clone. This partial cDNA contained a 2.1 kb open reading frame and 1 kb of 3' untranslated region (UTR). A full length clone was obtained by a combination of rescreening of the same dorsal lip library using a 670 base pair EcoRI/HpaI fragment at the 5' end of this clone and by 5' RACE (Gibco/BRL) using stage 10 *Xenopus* RNA.

To obtain a human homolog of *Xenopus* SARA, cDNA was synthesized from randomly primed total RNA isolated from HepG2 cells. This cDNA was subjected to polymerase chain reaction (PCR) using degenerate primers as described previously (Attisano et al., 1992). The 5' and 3' primers, designed to encode the zinc-finger motif, correspond to GC(A/C/G/T/)CC(A/C/G/T)AA(C/T)TG(C/TATGAA(A/C/G/T)TG(C/T) and (A/G)CA(A/G)TA(C/T)TC(A/C/G/T)GC(A/C/G/T)GG(A/G)TT(A/G)TT, respectively. A 150 base pair PCR product was sequenced and then used as probe for screening a λZAP human fetal brain cDNA library (Stratagene). Eight positive plaques were obtained, two of which contained an overlap of approximately 1 kb and covered the entire open reading frame. The sequence of the 5' UTR was confirmed by sequencing of an expressed sequence tag database clone (clone ID 260739).

Construction of Plasmids

For mammalian expression constructs of SARA, the open reading frame of hSARA was amplified by PCR and was subcloned into pCMV5 in frame with an amino-terminal Flag or Myc tag (Hoodless et al., 1996). The deletion mutants of pCMV5-Flag-hSaraΔ893–1323, Δ346–132, Δ893–1323, and Δ346–1323 were constructed by deletion of EcoRV-HindIII, XbaI-HindIII, SalI-EcoRV, and SalI-XbaI fragments, respectively. PCMV5-Flag-hSaraΔ1–594 and Δ1–686 were obtained by partial digestion with Asp718/SalI and for pCMV5-Flag-hSARA Δ665–1323 a Asp718/HindIII partial digest was used. PCMV5-Flag-hSARAΔ596–704 was constructed by deleting Asp718 fragment. The other hSARA mutants were constructed by PCR using appropriate primers. PCMV5B-Myc-Smad3 and Myc-Smad6, pGEX4T-1-Smad2/MH1 (amino acids 1–181), pGEX4T-1-Smad2/linker (amino acids 186–273), pGEX4T-1-Smad2/MH2 (amino acids 241–467) and pGEX4T-1-h SARA (amino acids 665–750) were constructed by PCR.

In Vitro Protein Interactions

In vitro transcription/translation reactions were performed using the TNT coupled reticulocyte lysate system (Promega) following the manufacturer's instructions using T3 RNA polymerase. Translation was carried out in the presence of [$^{35}$S]-methionine and labelled proteins were incubated with purified GST fusion proteins in TNTE buffer with 10% glycerol for 2 hours at 4° C. and then washed five times with the same buffer. Bound protein was separated by SDS-PAGE and visualized by autoradiography.

Immunoprecipitation and Immunoblotting

COS1 cells transfected with LipofectAMINE (GIBCO BRL) were lysed with lysis buffer (Wrana et al., 1994) and subjected to immunoprecipitation with either anti-Flag M2 (IBI, Eastern Kodak) or anti-Myc (9E10) monoclonal antibody followed by adsorption to protein-G sepharose. Precipitates were separated by SDS-PAGE, transferred to nitrocellulose membranes and immunoblotted as described previously (Hoodless et al., 1996).

Affinity-Labelling

LipofectAMINE transfected COS1 cells were incubated with 200 pM [$^{125}$I]TGFβ in media containing 0.2% bovine fetal serum at 37° C. for 30 minutes and receptors were cross-linked to ligand with DSS as described previously (Macias-Silva et al., 1996). Cell lysates were immunoprecipitated with anti-Flag antibody and receptors visualized by SDS-PAGE and autoradiography. In some cases, cross-linked [$^{125}$I]TGFβ was determined by gamma counting.

Subcellular Localization by Immunofluorescent Confocal Microscopy

Mv1Lu cells, plated on gelatin-coated Permanox chamber slides (Nunc), were transfected by the calcium phosphate-DNA precipitation method. Fixation, permeabilisation and reaction with the primary and secondary antibodies were described previously (Hoodless et al., 1996). Monoclonal anti-Flag antibodies were visualized by FITC-conjugated goat anti-mouse IgG (Jackson Laboratories) and polyclonal Myc antibody (A14, Santa Cruz) was visualized with Texas-Red-conjugated goat anti-rabbit IgG (Jackson Laboratories). Immunofluorescence was analyzed on a Leica confocal microscope.

Transcriptional Response Assay

Mv1Lu cells were transiently transfected with the reporter plasmid, p3TP-lux (Wrana et al., 1992), CMV-βgal and selected constructs using calcium phosphate transfection. Twenty-four hours after transfection, cells were incubated overnight with or without 50 pM TGFβ. Luciferase activity was measured using the luciferase assay system (Promega) in a Berthold Lumat LB 9501 luminometer and was normalized to β-galactosidase activity.

Example 2

Identification of SARA Family Members

The MH2 domain of Smad2 was fused to glutathione-S-transferase (GST) that included a kinase recognition site for protein kinase A (PKA). The bacterialy-expressed fusion protein was labelled to high specific activity using PKA (Chen and Sudol, 1995), and then used to screen a λZAPII expression library prepared from the dorsal blastopore lip of *Xenopus*. From this screen, four clones were identified, all of which presented a repeated isolate of a partial cDNA clone with no similarity to sequences in the GenBank database. To confirm that the product encoded by this clone interacted with Smad2, an in vitro transcription/translation system was used to produce [$^{35}$S]methionine-labelled protein. Translation of the cDNA yielded a protein product of approximately 80 kDa which corresponded in size to the longest open reading frame (ORF) identified in the sequence. Incubation of this product with bacterially-produced GST-Smad2 (MH2) resulted in efficient binding of the translated product to the fusion protein (data not shown). Interaction with full length Smad2 was also observed, whereas binding to bacterially-expressed Smad1 or Smad4 was not.

To isolate a full length cDNA, the partial clone identified in the interaction screen was used as a probe to rescreen the same blastopore lip library. Since the resulting clones lacked the 5' end, 5' RACE was conducted to obtain the entire coding sequence. Analysis of the complete cDNA sequence (Table 5) revealed a long open reading frame that was contiguous with that of the partial clone. The predicted protein, XSARA1, is 1235 amino acids long with an estimated molecular mass of 135 kDa (Table 6). Analysis of the full length cDNA sequence (Table 9) revealed a region in the middle portion of the predicted protein that had similarity to a double zinc finger domain (recently renamed the FYVE domain; Mu et al., 1995). The FYVE domain has been identified in a number of unrelated signaling molecules that include FGD1, a putative guanine exchange factor for Rho/

Rac that is mutated in faciogenital dysplasia (Pasteris et al., 1994), the HGF receptor substrate Hrs-1 and its homolog Hrs-2 (Bean et al., 1997; Komada and Kitamura, 1995), EEA1, a protein involved in formation of the early endosome (Mu et al., 1995) and the yeast proteins FAB1, VPS27 and VAC1 (Piper et al., 1995; Weisman and Wickner, 1992; Yamamoto et al., 1995). Comparison of the FWE domains from the vertebrate proteins with that from SARA revealed extensive conservation of residues throughout the domain (Table 10). Thus, SARA contains a FYVE domain that may fulfill important functions in diverse proteins.

To investigate the role of SARA in TGFβ superfamily signaling in mammalian cells, a human homologue was identified. Using a carboxy-terminal portion of XSARA1, a human library was screened and a protein was identified that was distantly related to *Xenopus* SARA (34% identity) and which was also sequenced as an EST (KIAA0305). However, no homologs closer to XSARA were identified. Thus, degenerate oligonucleotide primers were designed encoding amino acids in XSARA1 (Table 9) and HepG2 RNA was used as template for degenerate PCR. A related sequence was identified and this partial cDNA was used to screen a human brain cDNA library. Four overlapping clones, encoding a long open reading frame were identified and a search of the EST database with this sequence led to the identification of additional overlapping cDNA clones from libraries derived from T cells, uterus, endothelial cells and melanocytes. Analysis of the contiguous sequence revealed a long open reading frame that had a consensus start codon preceded by stop codons in all three reading frames (Table 1). Comparison of the predicted protein hSARA1 (Table 2), from this cDNA with XSARA1 (Table 9) revealed an overall identity of 62%, with a divergent 558 residue amino terminal domain (35% identity) followed by a closely related carboxy terminus (85% identity).

Example 3 hSARA Interacts Specifically with Smad2 and Smad3

Figure 1:
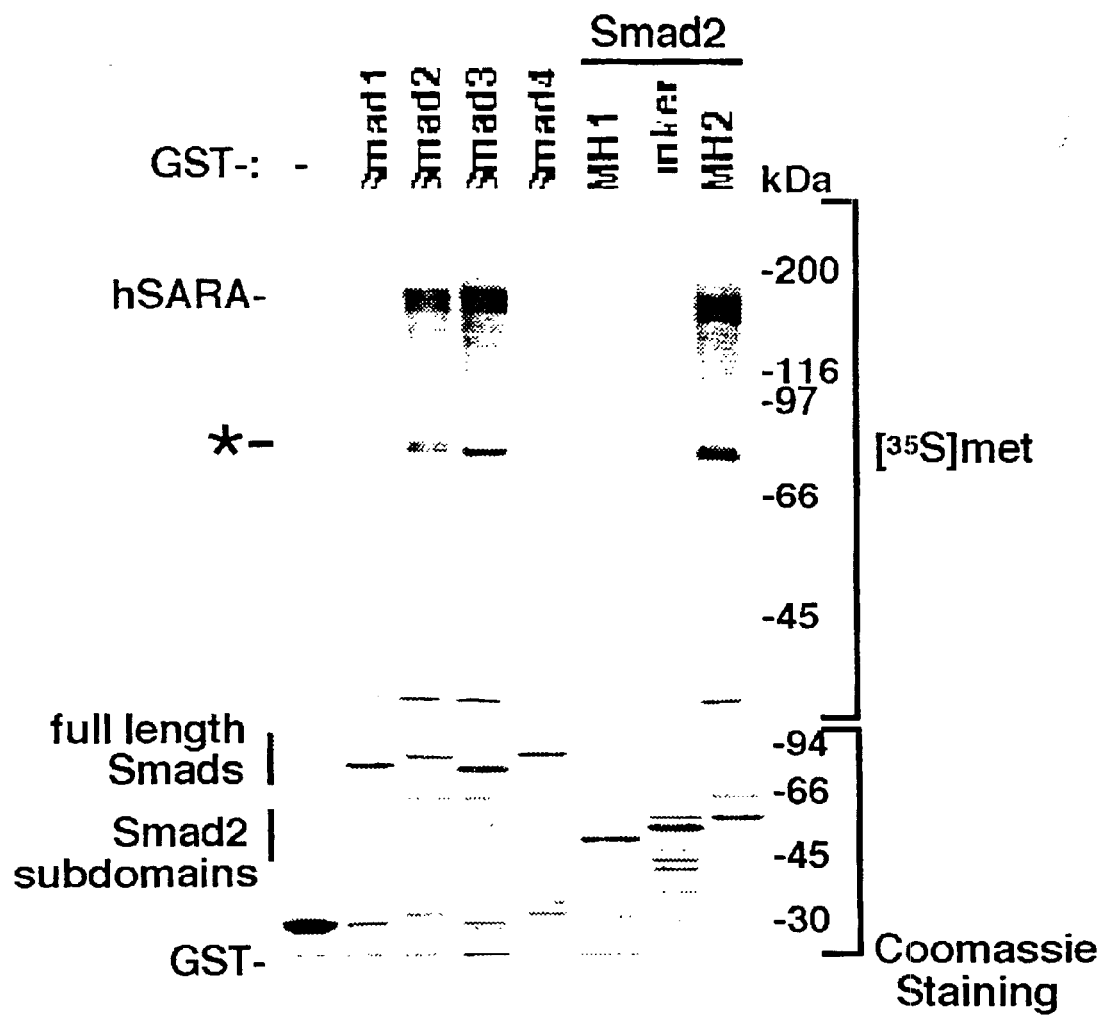
FIG. 1 (top panel) shows interaction of full length hSARA1 with bacterially expressed Smads. Full length SARA protein was produced in an in vitro transcription/translation system in the presence of [$^{35}$S]methionine and was incubated with glutathione-sepharose beads coated with bacterially-expressed GST fusion proteins of the indicated Smads or Smad2 subdomains. Bound material was resolved by SDS-PAGE and visualized by autoradiography. Migration of full length hSARA1, and a translation product that initiates from an internal methionine located upstream of the Smad binding domain (asterisk) are indicated. The presence of approximately equivalent amounts of GST fusion proteins was confirmed by SDSPAGE and coomassie staining of a protein aliquot (bottom panel).

To characterize the interaction of hSARA with Smads, the full length protein was translated in vitro and tested for binding to bacterially-expressed Smad fusion proteins. Similar to the *Xenopus* clone, hSARA1 bound specifically to full length Smad2, but not Smad1 or Smad4 (FIG. 1). In addition, full length Smad3, which is highly related to Smad2, also interacted with hSARA1. To define the domains of Smad2 that bound hSARA, in bacteria various fragments of Smad2 corresponding to the MH1 domain, linker region and MH2 domain were expressed in bacteria. Similar to the *Xenopus* clone, hSARA interacted efficiently with fusion proteins that comprised the MH2 domain, while no association was detected between hSARA and either the MH1 or non-conserved linker domains (FIG. 1). Thus, hSARA1 specifically interacts with Smad2 through the MH2 domain.

Figure 2:
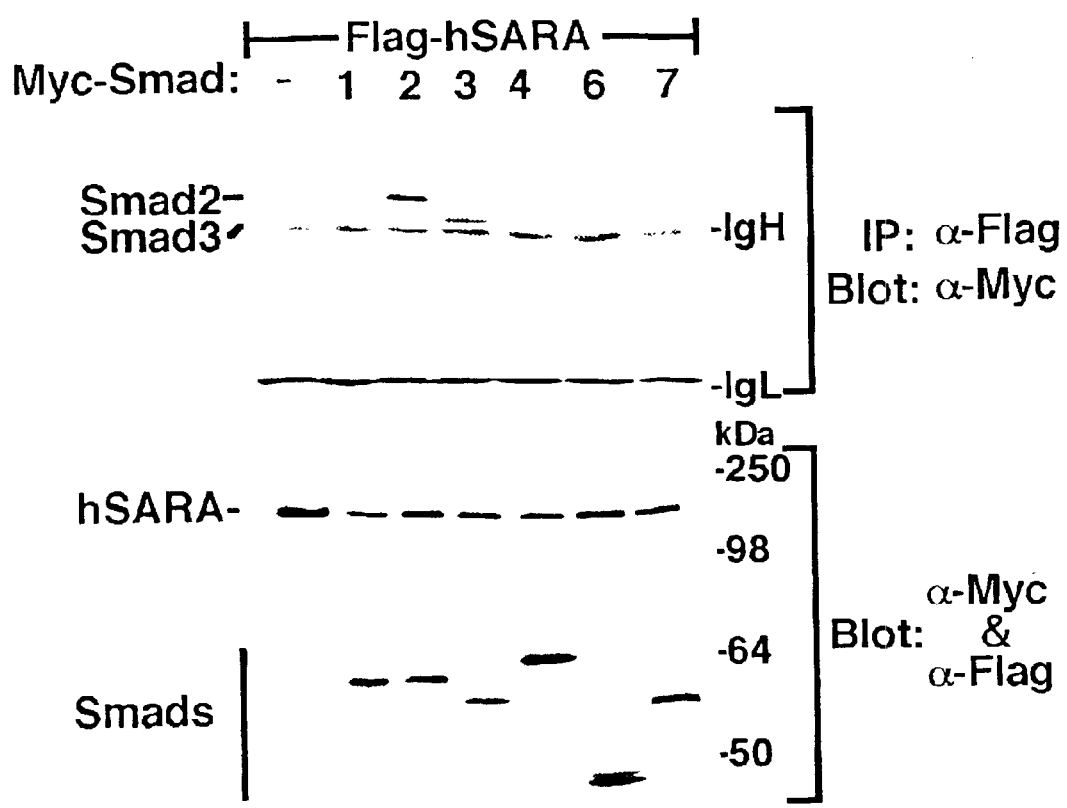
FIG. 2 shows interaction of hSARA with Smads in mammalian cells. COS cells were transfected with Flag-tagged hSARA1 (Flag-SARA) either alone or together with the indicated Myc-tagged Smad constructs. For Smad6, an alternative version lacking the MH 1 domain was used (Topper et al., 1997). Cell lysates were subjected to an anti-Flag immunoprecipitation and coprecipitating Smads detected by immunoblotting with anti-Myc antibodies. The migration of anti-Flag heavy and light chains (IgG) are marked. To confirm efficient expression of hSARA1 and the Smads, aliquots of total cell lysates were immunoblotted with the anti-Flag and anti-Myc antibodies (bottom panel). The migrations of hSARA1 and the Smads are indicated.

To confirm that hSARA also bound to Smads in mammalian cells, a Flag epitope tag was introduced at the amino terminus of the protein to create Flag-SARA. Transient expression of Flag-SARA in COS cells yielded a protein of the predicted molecular weight for SARA (FIG. 2) that was not present in untransfected cells (data not shown). To investigate the interaction of SARA with Smads, Flag-SARA was expressed in COS cells together with Myc-tagged versions of Smads 1, 2, 3, 4, 6 and 7. Cell lysates were subjected to anti-Flag immunoprecipitation followed by immunoblotting with anti-Myc antibodies. In other immunoprecipitates of cells expressing either Smad2 or Smad3, efficient coprecipitation of either Smad with Flag-hSARA1 was observed (FIG. 2). In contrast, none of the other Smads coprecipitated with hSARA1. Specific binding of this SARA family member to both Smad2 and Smad3 is consistent with the observation that these two proteins possess very closely related MH2 domains (97% identity) and are both activated by TGFβ or activin type I receptors (Liu et a., 1997b; Macias-Silva et al., 1996; Nakao et al., 1997a). Together, these results demonstrate that this SARA family member is a specific partner for receptor-regulated Smads of the TGFβ/activin signaling pathway.

Example 4

Phosphorylation of Smad2 Induces Dissociation from SARA

Figure 3:
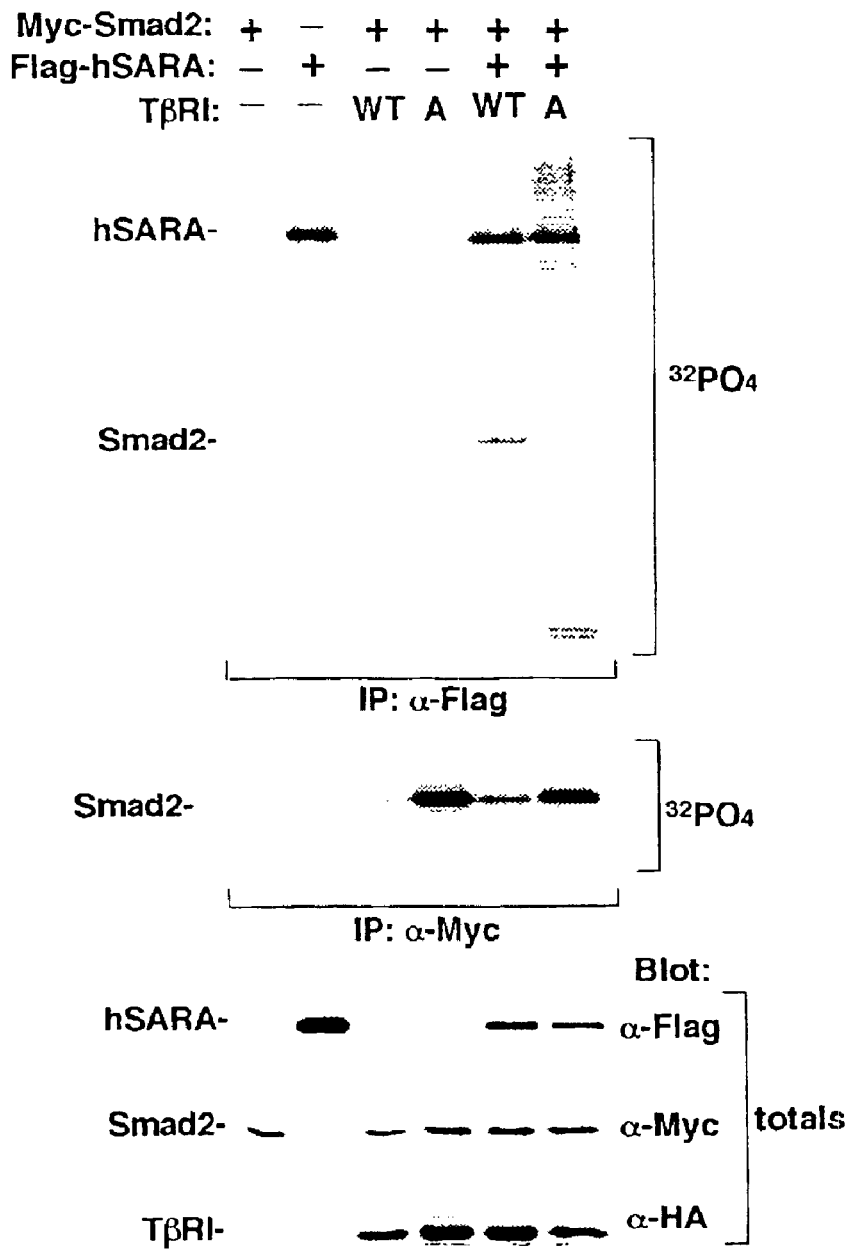
FIGS. 3–6 show immunoblots of lysates from COS cells transiently transfected with various combinations of Flag or Myc-tagged hSARA1, wild type (WT) or mutant (2SA) Myc or Flag-tagged Smad2, Smad4/HA and wild type (WT) or constitutively active (A) TβRI/HA, cell lysates being subjected to immunoprecipitation with anti-Flag or anti-Myc antibodies, as indicated. Confirmation of protein expression was performed by immunoblotting total cell lysates prepared in parallel for the indicated tagged protein (totals, bottom panels).

Previous findings have shown that activation of TGFβ signaling results in phosphorylation of Smad2 or Smad3 by type I receptors on C-terminal serine residues (Liu et al., 1997b; Macias-Silva et al., 1996). A constitutively active TGFβ type I receptor was prepared by substituting a threonine in the GS domain with an aspartate residue (Wieser et al., 1995). This activated type I receptor induces TGFβ signaling in the absence of type II receptors and ligand and regulates the phosphorylation and activation of Smad proteins in a manner similar to ligand (MaciasSilva et al., 1996; Wieser et al., 1995). COS cells were transfected withcombinations of Smad2, hSARA1 or both in the presence or absence of activated TβRI. Cells were then metabolically labelled with [$^{32}$P]phosphate and phosphorylation of either hSARA1 or Smad2 was assessed in immunoprecipitates. Analysis of SARA phosphorylation revealed that the protein was basally phosphorylated and the coexpression of the activated type I receptor did not appreciably affect the overall phosphorylation (FIG. 3). In contrast, analysis of Smad2 immunoprecipitated from total cell lysates showed that the activated type I receptor induced strong phosphorylation of the protein as described previously (Macias-Silva et al., 1996). These results suggest that SARA is not phosphorylated in response to TGFβ signaling.

Figure 4:
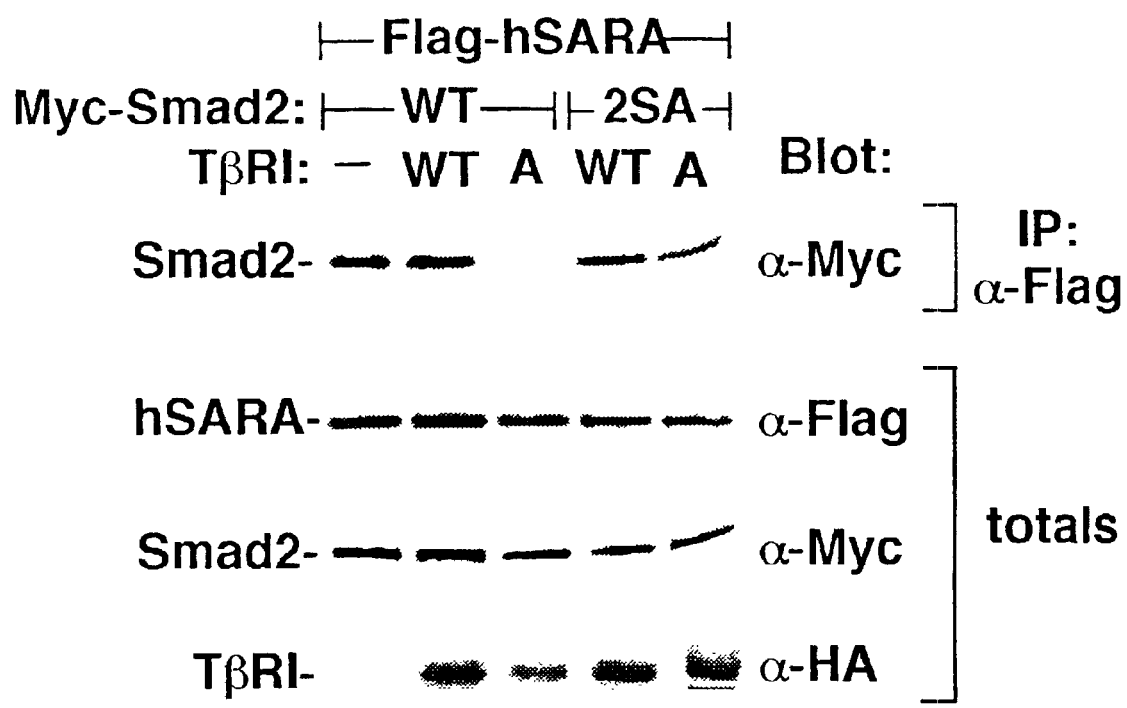

The phosphorylation state of Smad2 that coprecipitated with hSARA1 was examined. Interestingly, unlike the strong induction of Smad2 phosphorylation in the total cellular pool, phosphorylation of Smad2 associated with hSARA1 was not enhanced, but rather appeared to decrease in the presence of TGFβ signaling (FIG. 3). This suggested that receptor-dependent phosphorylation of Smad2 might induce dissociation from hSARA1. To examine this directly, the interaction of hSARA1 with wild type Smad 2 or a mutant version lacking the C-terminal phosphorylation sites (Smad2(2SA)) was analysed. In the absence of TGFβ signaling, association of hSARA1 with either Smad2 or Smad2(2SA) was comparable (FIG. 4). In contrast, in cells coexpressing the activated receptor, a significant decrease in the interaction of wild type Smad2 with hSARA1 was observed. However, hSARA1/Smad2(2SA) complexes were not reduced by the activated receptor. Together, these results suggest that hSARA1 is not phosphorylated in response to TGFβ signaling and that it preferentially interacts with the unphosphorylated form of Smad2.

Example 5

SARA and Smad4 form Mutually Exclusive Complexes with Smad2

Phosphorylation of Smad2 induces its interaction with Smad4 (Lagna et al., 1996; Zhang et al., 1997). hSARA1/

Figure 5:
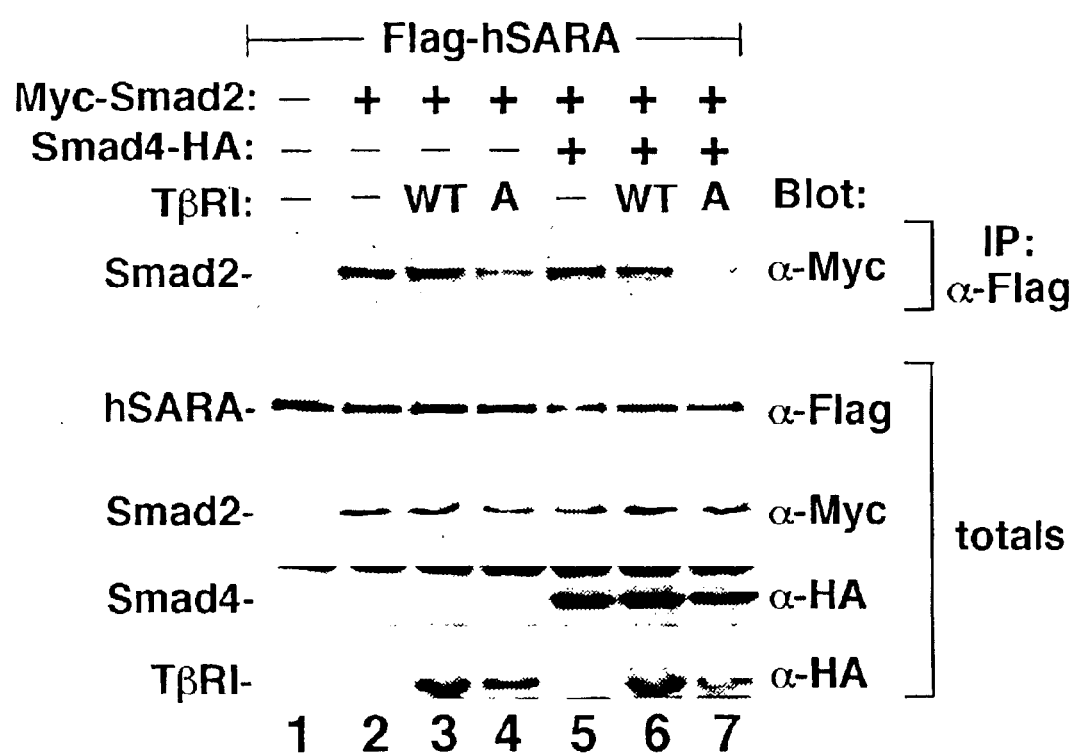
Figure 6:
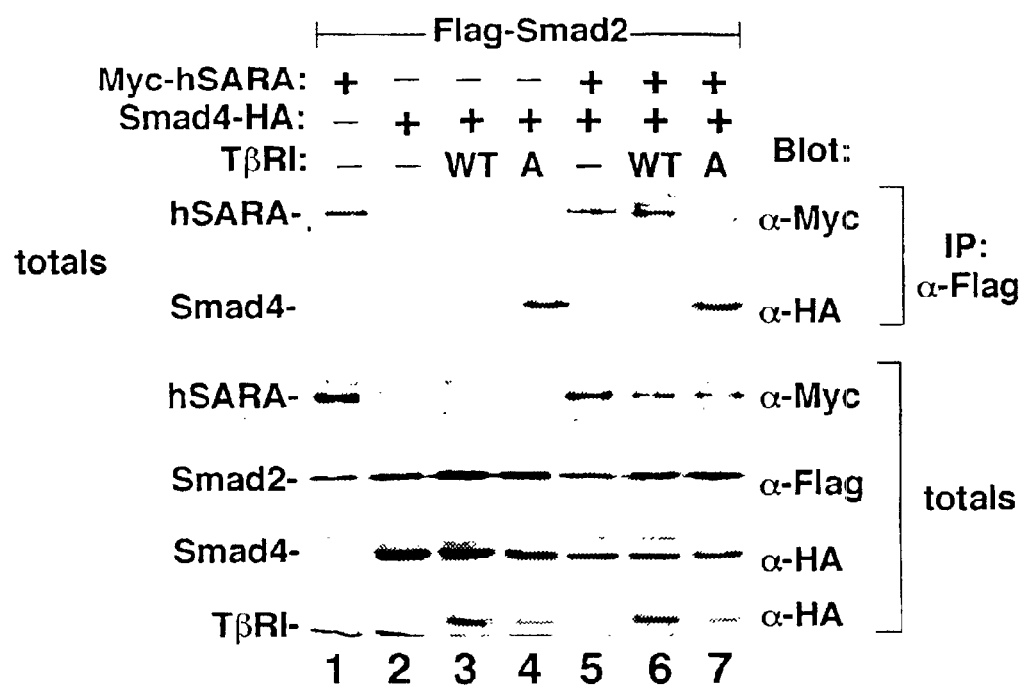

Smad2 complexes in COS cells coexpressing Smad4 were assessed. In unstimulated cells, the level of hSARA1/Smad2 complex formation was comparable either in the presence or absence of Smad4 (FIG. 5, lanes 3 and 6). However, upon activation of TGFβ signaling, dissociation of Smad2 from hSARA1 was significantly enhanced by coexpression of Smad4 (FIG. 5, lanes 4 and 7). These results indicated that phosphorylated Smad2 might preferentially interact with Smad4 rather than hSARA1 and suggested that Smad2 might form mutually exclusive complexes with either Smad4 or hSARA1. The formation of Smad2/Smad4 and Smad2/hSARA4 complexes in the same transfectants was then examined. Cell lysates were subjected to immunoprecipitation with anti-Flag antibodies directed towards tagged Smad2 and then immunoblotted for the presence of Smad4 and hSARA1. Consistent with previous findings (Lagna et al., 1996; Zhang et al., 1997), interaction of Smad4 with Smad2 was strongly stimulated by the activated type I receptor (FIG. 6, lane 3 and 4). Concomitant with the formation of Smad2/Smad4 complexes, the interaction of Smad2 with hSARA1 was disrupted by activation of signaling (FIG. 6, lanes 6 and 7). Thus, complexes of Smad2/hSARA1 and Smad2/Smad4 are mutually exclusive, supporting the notion that Smad4 may compete for Smad2 to enhance dissociation of hSARA1/Smad2 complexes. Together these results demonstrate that during TGFβ signaling, hSARA1/Smad2 complexes are transient and phosphorylation of Smad2 induces dissociation and formation of heteromeric complexes with Smad4.

Example 6 hSARA1 Regulates the Subcellular Localization of Smad2

The studies described above suggest that SARA functions upstream in the pathway and might control the subcellular localization of Smad2. To test this, an investigation was done to determine whether coexpression of hSARA1 might alter the localization of Smad2 in the TGFβ,responsive epithelial cell line, Mv1Lu, using confocal microscopy. Mv1Lu cells were used rather than COS since the Myc antibodies crossreacted with endogenous proteins in the COS and obscured nuclear staining of tagged proteins. In cells expressing hSARA1 alone, the protein displayed a punctate staining pattern that was present throughout the cytosolic compartment and was excluded from the nucleus (FIG. 7A). This localization of hSARA1 was in contrast to the diffuse staining typically observed for Smad2 in cells overexpressing the protein (FIG. 7B). Cells transiently transfected with both hSARA1 and Smad2 were examined. In these cells, the distribution of hSARA1 was indistinguishable from cells transfected with hSARA1 alone (FIG. 7D, left photo). In contrast, the localization of Smad2 in the presence of hSARA1 displayed a dramatic shift to a punctate pattern (compare FIG. 7B to 7D, centre photos). Moreover, analysis of these immunofluorescent staining patterns by confocal microscopy revealed that hSARA1 and Smad2 precisely colocalized in the cytosol (yellow stain, FIG. 7D, right photo). Interestingly, expression of Smad2 at much higher levels than hSARA1 reverted the distribution of Smad2 to that observed in cells transfected with Smad2 alone (data not shown). This supports the notion that elevating the amount of Smad2 can saturate hSARA1 and yield a diffuse distribution of Smad2 throughout the cell.

Studies were conducted to determine whether activation of TGFβ signaling induces nuclear translocation of Smad2 in the presence of hSARA1. As shown in FIG. 7, the localization of hSARA1 in the cytosolic compartment looked similar in the presence or absence of the constitutively active TGFβ type I receptor (compare FIG. 7D and E, left photos). However, TGFβ signaling caused a significant proportion of Smad2 to translocate to the nucleus (FIG. 7E, centre photo) and this correlated with a shift to an orangy-red colour in the cytosolic colocalization stain (FIG. 7E, right photo). Thus activation of TGFβ signaling induces Smad2 to dissociate from hSARA1 and translocate to the nucleus.

To confirm that the punctate localization of overexpressed SARA reflected that of the endogenous protein, the localization of endogenous SARA and Smad2 was examined in Mv1Lu cells. Analysis of the distribution of endogenous hSARA1 using affinityurified rabbit anti-hSARA1 antibodies revealed a punctate distribution that was similar to the pattern observed for transiently transfected, epitope-tagged hSARA1 (FIG. 7F, left photo). This staining was specific, since cells stained with preimmune antisera, or purified antibody blocked with the hSARA1 antigen, revealed no detectable staining in the cytosol, although some weak background staining was observed in the nucleus (data not shown). Examination of endogenous Smad2 distribution in the same cell using goat anti-Smad2 antibodies revealed a punctate distribution for Smad2 (FIG. 7F, centre photo) as published previously (aanknecht et al., 1998). Furthermore, analysis of hSARA1 and Smad2 together revealed extensive coiocalization of the two proteins (FIG. 7F, right photo). Colocalization was not complete and may reflect differences in the stoichiometry of hSARA1 versus Smad2 protein levels as suggested above, or the presence of additional regulatory mechanisms in the cell that control interaction of the endogenous proteins.

Taken together with the biochemical analysis, these results indicate that hSARA1 functions to anchor or recruit Smad2 to specific subcellular regions prior to activation by TGFβ signaling.

Example 7 hSARA1 Co-localises with TβRII

The positioning of hSARA1 upstream of Smad2 activation suggested to us that hSARA1 might recruit Smad2 to specific subcellular domains for phosphorylation and activation by the receptor. Interestingly, previous studies on the TGFβ receptor demonstrated clustering of the receptor complex into punctate domains that resembled those displayed by hSARA1 (Henis et al., 1994). To test whether hSARA1 might colocalize with TGFβ receptors, the subcellular localization of hSARA1 and TGFβ Mv1Lu receptors was investigated in Mv1Lu cells. Endogenous TGFβ receptors could not be detected, likely due to the low numbers of TGFβ receptors present on these cells and the even fewer number that are activated in the presence of ligand. The localization of hSARA1 in Mv1Lu cells cotransfected with TβRII and treated with TGFβ was therefore examined. In the absence of hSARA1, TβRII displayed a punctate staining pattern similar to the hSARA1 pattern (FIG. 8A, panels i and ii, respectively), as observed previously in COS cells. Furthermore, in cells coexpressing hSARA1 and TGFβ receptors, extensive colocalization of hSARA1 and TβRII was observed (FIG. 8A, panel iii). This colocalization was not complete. This may be due to a restricted distribution of hSARA1 in only a subset of the intracellular: compartments normally occupied by transmembrane receptors, which include the endoplasmic reticulum, Golgi and endocytic pathways. Thus, hSARA1 and the TGFβ receptors colocalize to common subcellular domains.

The colocalization of hSARA1 and the TGFβ receptors suggested the possiblity that hSARA1 may interact with the TGFβ receptor. To test this, a strategy was utilised similar to that employed to characterize the interaction of Smad2 with the TGFβ receptor (Macias-Silva et al., 1996). Briefly, COS cells were cotransfected with TGFβ receptors in the presence of hSARA1 and were affinity-labelled using [$^{125}$I] TGFβ. hSARA1 was then immunoprecipitated from the cell lysates and coprecipitating receptor complexes were resolved by SDS-PAGE and visualized by autoradiography or were quantitated using a gamma counter. Analysis of cells expressing wild type receptors type II and type I, revealed that receptor complexes coprecipitated with hSARA1 (FIG. 8B, lane 3). Furthermore, in the presence of kinase deficient type I receptor, there was a small increase in binding of hSARA1 to the receptor (FIG. 8B, lane 2). This is in contrast to Smad2, which only interacts with TGFβ, receptor complexes that contain kinase deficient type I receptors (Macias-Silva et al., 1996). These data suggest that hSARA1 associates with the TGFβ receptor.

Next examined was whether coexpression of Smad2 might enhance the interaction of hSARA1 with TGFβ receptors. In cells expressing wild type receptor I, no difference in the amount of receptor complexes that coprecipitated with hSARA1, either in the presence or absence of Smad2, was observed (FIG. 8B, compare lanes 3 and 5). In contrast, the association of hSARA1 with receptor complexes containing kinase-deficient type I receptors was enhanced by Smad2 (FIG. 8B, lane 4). This finding was consistent with the previous demonstration that kinase-deficient type I receptors stabilize interactions of Smad2 with the receptors. To investigate further the requirement for Smad2 in the interaction of hSARA1 with the receptor, a mutant of hSARA1, SARA (ΔSBD), that removes the Smad binding domain, was tested. Analysis of wild type hSARA1 interaction with receptor complexes containing kinase-deficient TβRI showed that wild type hSARA1 interacted with the receptor and this was enhanced approximately two-fold by Smad2 (FIG. 9A). The ΔSBD mutant of hSARA1 retained the capacity to associate with the receptor, although the efficiency of interaction was slightly reduced relative to wild type hSARA1. Importantly, unlike wild type hSARA1, binding of mutant hSARA1 to the receptor was not enhanced by coexpression of Smad2. Together, these data suggest that hSARA1 interacts with the TGFβ receptor independently of Smad2 binding and that Smad2 cooperates to enhance the association.

To further characterize the domains in SARA that mediate binding to the TGFβ receptor, the interaction of a panel of SARA mutants with the TGFβ receptor was tested. Interestingly, interaction with the TGFβ receptor was strongly suppressed in three mutants in which the FYVE domain was disrupted (FIG. 9B; Δ594, Δ664 and the internal deletion Δ597–665). Since the FYVE domain is required for the correct subcellular localization of SARA, it was postulated that, once bound to the membrane, other regions in SARA might contribute to the interaction with the receptor. To examine this possibility, several carboxy-terminal truncation mutants of hSARA1 were tested. Interestingly, deletion of the C-terminus downstream of position 750 suppressed receptor interaction, despite efficient expression of the truncated protein. This suggests that regions in the carboxy-terminus of SARA contribute to receptor interaction. In these analyses, the question of whether overexpression of Smad2 could rescue some interaction of SARA mutants with the receptor was also explored. For both the FYVE domain mutants and the C-terminal truncation, Smad2 expression was able to restore some interaction with the TGFβ receptor. it is likely that the high levels of protein and receptor expression that are achieved in COS cells can drive some receptor interaction, even in the absence of appropriate localization signals.

Example 8

A Modular Domain in SARA Mediates Association with Smads

To investigate the functional importance of SARA in TGFβ signaling, the domains in the protein that mediate both its localization to specific subcellular regions and its interaction with Smad2 were defined. To this end, a series of deletion mutants of hSARA1 were constructed and tested for their ability to interact with Smad2 in COS cells by immunoprecipitation followed by immunoblotting. As summarized in FIG. 10, loss of the first 665 amino acids of hSARA1, which included the double zinc finger/FYVE domain, did not interfere with hSARA1 binding to Smad2. However, further deletions (Δ1–704) completely abolished the interaction of Smad2 with hSARA1. To map the carboxy-terminal boundary of the Smad binding domain, a number of C-terminal truncations were also analyzed. Deletion of all residues downstream of position 750 did not affect Smad2 interaction with hSARA1, while an additional loss of 85 amino acids (Δ665–1323) completely abrogated binding to Smad2. To determine whether the region defined by this deletional analysis was sufficient to bind Smad2, the 85 amino acids referred to as the Smad Binding Domain (SBD) were linked to GST and the fusion protein was expressed in bacteria (GST-h SARA(665–750)). incubation of lysates prepared from cells expressing Smad2 or Smad3 with GST-SBD resulted in efficient binding of both Smads to the fusion protein (FIG. 11A). This interaction is likely direct, since bacterially expressed SBD associates efficiently with bacterially-produced Smad2 (data not shown). These studies thus define a novel domain in SARA that mediates interaction with Smad2 and Smad3 and which is located downstream of the FYVE domain.

The above-described analysis in COS cells showed that phosphorylation of Smad2 by the TGFβ receptor induced dissociation from SARA. To determine whether this reflects an alteration in the ability of the SBD to bind phosphorylated Smad2, the interaction of GST-SBD with Smad2 in lysates obtained from cells expressing Smad2 alone, or Smad2 together with either wild type or activated TGFβ type I receptor, was tested. As described previously, coexpression of activated type I receptors with the appropriate receptor-regulated Smad yields efficient phosphorylation of Smad protein. In lysates from cells expressing Smad2 alone or Smad2 with wild type receptors, efficient binding of Smad2 to GST-SBD was observed. In contrast, in the presence of activated TβRI, the interaction of Smad2 with GST-SBD was strongly reduced (FIG. 11B). This reduction correlated with receptor-dependent phosphorylation, since the phosphorylation site mutant, Smad2(2SA), interacted efficiently with GST-SBD, even in the presence of activated TβRI (data not shown). These data strongly support a mechanism whereby SARA interacts with unphosphorylated Smad2 and receptor-dependent phosphorylation induces dissociation by altering the affinity of Smad2 for the SBD.

Example 9

The FYVE Domain Controls the Subcellular Localization of SARA

The subcellular localization of a selection of the SARA mutants was analysed by immunofluorescence and confocal microscopy. Analysis of truncation mutants that removed the amino terminus upstream of the FYVE domain (Δ1–531) yielded wild type patterns of staining (FIG. 12, compare panels i and ii). However, a further deletion (Δ1–664) that disrupted the FYVE domain but did not interfere with the Smad binding domain, abolished the wild type staining pattern (FIG. 12, panel iii). Similar studies of the C-terminal domains showed that residues downstream of the FYVE domain (Δ665–1323) did not alter the localization of the mutant protein (FIG. 12, panel iv), while truncations within the FYVE domain (Δ596–1323) led to diffuse localization throughout the cell (FIG. 12, panel v). Of note, the Δ665–1323 mutant lacked the Smad binding domain, thereby indicating that interaction with Smad2 is not required for proper SARA localization. To confirm that FYVE domain function was required for localization of SARA, a mutant with a small internal deletion that removes the FYVE domain (Δ597–664) was tested. Consistent with the other mutants, localization of this protein was clearly disrupted (FIG. 12, panel vi). Since none of these mutants interfered with Smad binding, the FYVE domain appears to be required to maintain the normal localization of SARA but is not involved in mediating interactions with Smads.

Example 10

SARA-mediated Localization of Smad2 is Necessary for TGFβ Signaling

The availability of mutants of hSARA1 that interact with Smad2 but fail to target to the appropriate subcellular sites allowed the question of whether hSARA1-mediated localization of Smad2 was important to TGFβ signaling to be addressed. Whether SARA(Δ1–594) and SARA(Δ1–664), which bind Smad but fail to distribute to the correct subcellular domains, would mislocalize Smad2 was examined. Coexpression of either mutant with Smad2 showed that they were unable to recruit Smad2 to the normal SARA domains (FIG. 13A, panels i and ii). As expected, SARA(Δ1–704), which lacks a Smad binding domain, was unable to control Smad2 localization (FIG. 13A, panel iii). Whether these mutants could cause mislocalization of Smad2 was also examined. For this, cells were cotransfected with wild type hSARA1 and Smad2 either in the absence or presence of SARA(Δ1–594), SARA(Δ1–664) or SARA(Δ1–704). In control transfectants, performed in the absence of mutant hSARA1, hSARA1 and Smad2 were colocalized in punctate domains as described above (FIG. 13B, panel i). However, in the presence of either SARA(Δ1–594) or SARA(Δ1–664), the localization of wild type hSARA1 was normal, but the distribution of Smad2 was clearly disrupted and displayed a diffuse pattern (FIG. 13B, panels ii and iii, respectively). Moreover, coexpression of SARA(Δ1–704), which does not bind Smad2, resulted in Smad2 distribution that was indistinguishable from that of the wild type pattern (FIG. 13B, panel iv). Thus, SARA(Δ1–594) and SARA(Δ1–664) induce the mislocalization of Smad2.

Since SARA(Δ1–664) mislocalizes Smads and interferes with receptor association, we investigated whether this mutant would disrupt TGFβ signaling. To test this, we transiently transfected the TGFβ-responsive reporter gene 3TP-lux into Mv1Lu cells in the presence and absence of wild type or mutant versions of hSARA1. Expression of wild type hSARA1 had no effect on TGFβ signaling (FIG. 14). In contrast, transfection of SARA(Δ1–664) significantly inhibited TGFβ-dependent signaling at the lowest concentration of DNA tested, while transfection of higher doses completely abolished responsiveness of the cells. We also tested SARA(Δ1–704) which lacks a functional Smad binding domain and does not alter Smad2 localization. Transfection of this mutant had no effect on TGFβ signaling (FIG. 14). In addition to analysis of the 3TP promoter, we examined induction of the activin response element (ARE) from the *Xenopus* Mix.2 gene in HepG2 cells.

This ARE is stimulated by either TGFβ or activin signaling, which induces assembly of a DNA binding complex that is composed of Smad2, Smad4 and a member of the FAST family of forkhead DNA binding proteins. Since HepG2 cells do not possess endogenous FAST activity, wild type or mutants of hSARA1 were cotransfected with FAST2 and the ARE-lux reporter plasmid as described previously (Labbé et al., 1998). Expression of either SARA(1–Δ594) or SARA(1–Δ664), which interfere with or delete the FYVE domain, respectively, resulted in a strong suppression of TGFβ-dependent induction of the ARE (FIG. 15). However, none of the other mutants tested suppressed activation of this promoter. Since none of these latter mutants disturb the localization of hSARA1-Smad2 complexes, these data strongly suggest that recruitment of Smad2 to the receptor-containing subcellular domains is important for TGFβ signaling.

Example 11

Tissue Distribution of hSARA Expression

The 3'UTR of hSARA1 and a Smad2 cDNA fragment were used to probe a human multiple tissue Northern blot (Clontech). The results are shown in FIG. 16—hSARA1: upper panel and Smad2: lower panel. hSARA1 and Smad2 were ubiquitously expressed in the tissues examined; relatively low levels of hSARA1 were selected in liver. hSARA1 and Smad2 showed a similar expression pattern except in placenta, where proportionally more Smad2 message was observed. A single transcript of 5.0 kb is seen, corresponding to the full length hSARA1 cDNA.

SARA expression was examined in a variety of cell lines using RT-PCR analysis and the gene was found to be expressed in every cell line tested. These included HepG2 hepatoma cells, NBFL neuroblastoma cells, SW480 colorectal cancer cells, N1 H 3T3 fibroblasts, P19 embryonic carcinoma cells, MC3T3 calvarial cells and Mv1Lu lung epithelial cells (data not shown). hSARA1 appears to be a ubiquitously expressed partner for Smad2 and Smad3.

Example 12

Interaction of Endopenous hSARA1 and Smad2 in Mammalian Cells

Lysates from HepG2 cells, either untreated or treated with InM TGFβ, were immunoprecipitated with an affinity-purified, anti-hSARA1 rabbit polyclonal antibody and the immunoprecipitates were immunoblotted with a polyclonal, anti-Smad2 antibody (Macias-Silva et al., 1998). Controls were immunoprecipitated with pre-immune sera or N19 anti-Smad2/3 antibody. The results are shown in FIG. 17. In immunoprecipitates prepared with preimmune antisera, no Smad2 was detectable. Anti-hSARA1 immunoprecipitates clearly showed Smad2 coprecipitating with hSARA1. TGFβ treatment prior to lysis gave decreased association of Smad2 and SARA.

These results demonstrate that SARA is a specific partner of receptor-regulated Smads in the TGFβ/activin signaling pathway and further suggest that TGFβ signaling induces dissociation of SARA/Smad complexes.

REFERENCES

Abdollah, S., Macías-Silva, M., Tsukazaki, T., Hayashi, H., Attisano, L., and Wrana, J. L. (1997). TβRI phosphorylation of Smad2 on Ser 465 and 467 is required for Smad2/Smad4 complex formation and signaling. J. Biol. Chem. 272, 27678–27685.

Attisano, L. and Wrana, J. L. (1998). Mads and Smads in TGFβ signaling. Curr. Op. Cell Biol. 10, 188–194.

Attisano, L., Wrana, J. L., Cheifetz, S., and Massagué, J. (1992). Novel activin receptors: Distinct genes and alternative mRNA splicing generate a repertoire of serine/threonine kinase receptors. Cell 68, 97–108.

Bean, A. J., Siefert, R., Chen, Y. A., Sacks, R., and Scheller, R. H. (1997). Hrs-2 is an ATPase implicated in calcium-regulated secretion. Nature 385, 826–829.

Burd et al., (1998), Mol. Cell., 2, 157–162.

Chen, H. I. and Sudol, M. (1995). The WW domain of Yes-associated protein binds a proline-rich ligand that differs from the consensus established for Src homology 3-binding modules. Proc Natl Acad Sci USA 82, 7819–7823.

Chen, X., Rubock, M. J., and Whitman, M. (1996). A transcriptional partner for MAD proteins in TGF-β signaling. Nature 383, 691–696.

Chen, X., Weisberg, E., Fridmacher, V., Watanabe, M., Naco, G., and Whitman, M. (1997a). Smad4 and FAST-1 in the assembly of activin-responsive factor. Nature 389, 85–89.

Chen, Y., Bhushan, A., and Vale, W. (1997b). Smad8 mediates the signaling of the receptor serine kinase. Proc. Natl. Acad. Sci. USA 94, 12938–12943.

Chen, Y., Lebrun, J. -J., and Vale, W. (1996). Regulation of transforming growth factor β- and activin-induced transcription by mammalian Mad proteins. Proc. Natl. Acad. Sci. USA 93, 12992–12997.

Dennler, S., Itoh, S., Vivien, D., ten Dijke, P., Huet, S., and Gauthier, J. -M. (1998). Direct binding of Smad3 and Smad4 to critical TGFβ-inducible elements in the promoter of human plasminogen activator inhibitor-type 1 gene. EMBO J. 17, 3091–3100.

Dyson, S. and Gurdon, J. B. (1998). The Interpretation of Position in a Morphogen Gradient as Revealed by Occupancy of Activin Receptors. Cell 93, 557–568.

Faux, M. and Scott, J. D. (1996). Molecular glue: kinase anchoring and scaffold proteins. Cell 85, 9–12.

Gaullier et al., (1998), Nature, 394, 433–434.

Heldin, C. -H., Miyazono, K., and ten Dijke, P. (1997). TGF-β signaling from cell membrane to nucleus through SMAD proteins. Nature. 390, 465–471.

Henis, Y. I., Moustakas, A., Lin, H. Y., and Lodish, H. F. (1994). The type II and III transforming growth factor-β receptors form homo-oligomers. J. Cell Biol. 126, 139–154.

Hoodless, P. A., Haerry, T., Abdollah, S., Stapleton, M., O'Connor, M. B., Attisano, L., and Wrana, J. L. (1996). MADR1, a MAD-related protein that functions in BMP2 signaling pathways. Cell 85, 489–500.

Janknecht et al., (1998), Genes & Development, 12 2114–2119.

Kim, J., Johnson, K., Chen, H. J., Carroll, S., and Laughon, A. (1997). Drosophila Mad binds to DNA and directly mediates activation of vestigial by decapentaplegic. Nature 388, 304–308.

Komada, M. and Kitamura, N. (1995). Growth factor-induced tyrosine phosphorylation of Hrs, a novel 115-kilodalton protein with a structurally conserved putative zinc finger domain. Mol Cell Biol 15, 6213–6221.

Kretzschmar, M., Liu, F., Hata, A., Doody, J., and Massagué, J. (1997). The TGF-β family mediator Smad1 is phosphorylated directly and activated functionally by the BMP receptor kinase. Genes Dev. 11, 984–995.

Kretzschmar, M. and Massagué, J. (1998). SMADs: mediators and regulators of TGF-β signaling. Current Opinion in Genetics & Development 8, 103–111.

Labbé, E., Silvestri, C., Hoodless, P. A., Wrana, J. L., and Attisano, L. (1998). Smad2 and Smad3 positively and negatively regulate TGFβ-dependent transcription through the forkhead DNA binding protein, FAST2. Molecular Cell in press.

Lagna, G., Hata, A., Hemmati-Brivanlou, A., and Massagué, J. (1996). Partnership between DPC4 and SMAD proteins in TGF-β signaling pathways. Nature 383, 832–836.

Liu, F., Pouponnot, C., and Massagué, J. (1997a). Dual role of the Smad4/DPC4 tumor suppressor in TGFβ-inducible transcriptional complexes. Genes & Development 11, 3157–3167.

Liu, X., Sun, Y., Constantinescu, S. N., Karam, E., Weinberg, R. A., and Lodish, H. F. (1997b). Transforming growth factor β-induced phosphorylation of Smad3 is required for growth inhibition and transcriptional induclion in epithelial cells. Proc. Natl. Acad. Sci. USA 94, 10669–10764.

Macias-Silva, M., Abdollah, S., Hoodless, P. A., Pirone, R., Attisano, L., and Wrana, J. L. (1996). MADR2 is a substrate of the TGFβ receptor and its phosphorylation is required for nuclear accumulation and signaling. Cell 87, 1215–1224.

Mu, F. T., Callaghan, J. M., Steele-Mortimer, O., Stenmark, H., Parton, R. G., Campbell, P. L., McCluskey, J., Yeo, J. P., Tock, E. P., and Toh, B. H. (1995). EEA1, an early endosome-associated protein. EEA1 is a conserved alpha-helical peripheral membrane protein flanked by cysteine "fingers" and contains a calmodulin-binding IQ motif. J Biol Chem 270, 13503–13511.

Nakao, A., Imamura, T., Souchelnytskyi, S., Kawabata, M., Ishisaki, A., Oeda, E., Tamaki, K., Hanai, J. -i., Heldin, C. -H., Miyazono, K., and ten Dijke, P. (1997a). TGF-β receptor-mediated signaling through Smad2, Smad3 and Smad4. EMBO J. 16, 5353–5362.

Nakao, A., Röijer, E., imamura, T., Souchelnytskyi, S., Stenman, G., Heldin, C.-H., and ten Dijke, P. (1997b). Identification of Smad2, a human Mad-related protein in the transforming growth factor β signaling pathway. J. Biol. Chem. 272, 2896–2900.

Nakayama, T., Snyder, M. A., Grewal, S. S., Tsuneizumi, K., Tabata, T., and Christian, J. L. (1998). Xenopus Smad8 acts downstream of BMP-4 to modulate its activity during vertebrate embryonic patterning. Development 125, 857–867.

Nishimura, R., Kato, Y., Chen, D., Harris, S. E., Mundy, G. R., and Yoneda, T. (1998). Smad5 and DPC4 are key molecules in mediating BMP-2-induced osteoblastic differentiation of the pluripotent mesenchymal precursor cell line C2C12.J. Biol. Chem. 273, 1872–1879.

Pasteris, N. G., Cadle, A., Logie, L. J., Porteous, M. E., Schwartz, C. E., Stevenson, R. E., Glover, T. W., Wilroy, R.

S., and Gorski, J. L. (1994). Isolation and characterization of the faciogenital dysplasia (Aarskog-Scott syndrome) gene: a putative Rho/Rac guanine nucleotide exchange factor. Cell 79, 669–678.

Patki et al., (1998), Nature, 394, 433–4.

Patterson, G., Koweek, A., Wong, A., Liu, Y., and Ruvkun, G. (1997). The DAF-3 Smad protein antagonizes TGF-β-related receptor signaling in the C. elegans dauer pathway. Genes and Dev.

Pawson, T. and Scott, J. D. (1997). Signaling through scaffold, anchoring and adaptor proteins. Science 278, 2075–2080.

Piper, R. C., Cooper, A. A., Yang, H., and Stevens, T. H. (1995). VPS27 controls vacuolar and endocytic traffic through a prevacuolar compartment in Saccharomyces cerevisae. J Cell Biol 131, 603–617.

Savage, C., Das, P., Finelli, A., Townsend, S., Sun, C., Baird, S., and Padgett, R. (1996). The C. elegans sma-2, sma-3 and sma-4 genes define a novel conserved family of TGF-β pathway components. Proc. Natl. Acad. Sci. USA 93, 790–794.

Sekelsky, J. J., Newfeld, S. J., Raftery, L. A., Chartoff, E. H., and Gelbart, W. M. (1995). Genetic characterization and cloning of Mothers against dpp, a gene required for decapentaplegic function in Drosophila melanogaster. Genetics 139, 1347–1358.

Simonsen et al., (1998), Nature, 394, 494–495.

Souchelnytskyi, S., Tamaki, K., Engström, U., Wernstedt, C., ten Dijke, P., and Heldin, C. -H. (1997). Phosphorylation of Ser$^{465}$ and Ser$^{467}$ in the C Terminus of Smad2 Mediates Interaction with Smad4 and is Required for Transforming Growth Factor-β Signaling. J. Biol. Chem. 272, 28107–28115.

Topper, J. N., Cai, J., Qiu, Y., Anderson, K. R., Xu, Y. -Y., Deeds, J. D., Feeley, R., Gimeno, C. J., Woolf, E. A., Tayber, O., Mays, G. G., Sampson, B. A., Schoen, F. J., Gimbrone, M. A. J., and Falb, D. (1997). Vascular MADs: two novel MAD-related genes selectively inducible by flow in human vascular endothelium. Proc. Natl. Acad. Sci. USA 94, 9314–9319.

Weisman, L. S. and Wickner, W. (1992). Molecular characterization of VAC1, a gene required for vacuole inheritance and vacuole protein sorting. J Biol Chem 267, 618–623.

Wiedemann et al., (1998), Nature, 394, 426–427.

Wieser, R., Wrana, J. L., and Massague, J. (1995). GS domain mutations that constitutively activate TβR-I, the downstream signaling component in the TGF-β receptor complex. EMBO J. 14, 2199–2208.

Wrana, J. L., Attisano, L., Carcamo, J., Zentella, A., Doody, J., Laiho, M., Wang, X. -F, and Massagueé, J. (1992). TGF-β signals through a heteromeric protein kinase receptor complex. Cell 71, 1003–1014.

Wrana, J. L., Attisano, L., Wieser, R., Ventura, F., and Massague, J. (1994). Mechanism of activation of the TGF-β receptor. Nature 370, 341–347.

Yamamoto, A., DeWald, D. B., Boronenkov, I. V., Anderson, R. A., Emr, S. D., and Koshland, D. (1995). Novel PI(4)P 5-kinase homologue, Fab1p, essential for normal vacuole function and morphology in yeast. Mol Biol Cell 6, 525–539.

Yingling, J. M., Datto, M. B., Wong, C., Frederick, J. P., Liberati, N. T., and Wang, X. -F. (1997). Tumour Suppressor Smad4 is a Transforming Growth Factor β-Inducible DNA Binding Protein. Mol. Cell. Biol. 17, 7019–7028.

Zawel, L., Dai, J. L., Buckhaults, P., Zhou, S., Kinzler, K. W., Vogelstein, B., and Kern, S. E. (1998). Human Smad3 and Smad4 are sequence-specific transcription activators. Mol. Cell 1, 611–617.

Zhang, Y., Musci, T., and Derynck, R. (1997). The tumor suppressor Smad4/DPC4 as a central mediator of Smad function. Curr. Biol. 7, 270–276.

TABLE 1

| hSARA1 - Sequence ID NO:1 |
| --- |
| GCATACTGAATCAGCAGGACTGGCTGGTGGTGCAGCAGACATCATGAGTAAGCACCGA |
| GAAGTCTGTTCCTTATCACGTGTGTAAGGGGAAAAAGGTTTAAACAAGTCTCTTAAGT |
| GGTGTTTCCTCACCGATGGAGAATTACTTCCAAGCAGAAGCTTACAACCTGGGACAAG |
| GTGTTAGATGAATTTGAACAAAACGAAGATGAAACAGTTTCTTCTACTTTATTGGATA |
| CAAAGTGGAATAAGATTCTAGATCCCCCTTCTCACCGGCTGTCATTTAACCCTACTTT |
| GGCCAGTGTGAATGAATCTGCAGTTTCTAATGAGTCACAACCACAACTGAAAGTCTTC |
| TCCCTGGCTCATTCAGCTCCCCTGACCACAGAGGAAGAGGATCACTGTGCTAATGGAC |
| AGGACTGTAATCTAAATCCAGAGATTGCCACAATGTGGATTGATGAAAATGCTGTTGC |
| AGAAGACCAGTTAATTAAGAGAAACTATAGTTGGGATGATCAATGCAGTGCTGTTGAA |
| GTGGGAGAGAAGAAATGTGGAAACCTGGCTTGTCTGCCAGATGAGAAGAATGTTCTTG |
| TTGTAGCCGTCATGCATAACTGTGATAAAAGGACATTACAAAACGATTTACAGGATTG |
| TAATAATTATAATAGTCAATCCCTTATGGATGCTTTTAGCTGTTCACTGGATAATGAA |
| AACAGACAAACTGATCAATTTAGTTTTAGTATAAATGAGTCCACTGAAAAGATATGA |
| ATTCAGAGAAACAAATGGATCCATTGAATAGACCGAAAACAGAGGGGAGATCTGTTAA |
| CCATCTGTGTCCTACTTCATCTGATAGTCTAGCCAGTGTCTGTTCCCCTTCACAATTA |

TABLE 1-continued hSARA1 - Sequence ID NO:1

AAGGATGACGGAAGTATAGGTAGAGACCCCTCCATGTCTGCGATTACAAGTTTAACGG

TTGATTCAGTAATCTCATCCCAGGGAACAGATGGATGTCCTGCTGTTAAAAAGCAAGA

GAACTATATACCAGATGAGGACCTCACTGGCAAAATCAGCTCTCCTAGGACAGATCTA

GGGAGTCCAAATTCCTTTTCCCACATGAGTGAGGGGATTTTGATGAAAAAAGAGCCAG

CAGAGGAGAGCACCACTGAAGAATCCCTCCGGTCTGGTTTACCTTTGCTTCTCAAACC

AGACATGCCTAATGGGTCTGGAAGGAATAATGACTGTGAACGGTGTTCAGATTGCCTT

GTGCCTAATGAAGTTAGGGCTGATGAAAATGAAGGTTATGAACATGAAGAAACTCTTG

GCACTACAGAATTCCTTAATATGACAGAGCATTTCTCTGAATCTCAGGACATGACTAA

TTGGAAGTTGACTAAACTAAATGAGATGAATGATAGCCAAGTAAACGAAGAAAAGGAA

AAGTTTCTACAGATTAGTCAGCCTGAGGACACTAATGGTGATAGTGGAGGACAGTGTG

TTGGATTGGCAGATGCAGGTCTAGATTTAAAAGGAACTTGCATTAGTGAAAGTGAAGA

ATGTGATTTCTCCACTGTTATAGACACACCAGCAGCAAATTATCTATCTAATGGTTGT

GATTCCTATGGAATGCAAGACCCAGGTGTTTCTTTTGTTCCAAAGACTTTACCCTCCA

AAGAAGATTCAGTAACAGAAGAAAAAGAAATAGAGGAAAGCAAGTCAGAATGCTACTC

AAATATTTATGAACAGAGAGGAAATGAGGCCACAGAAGGGAGTGGACTACTTTTAAAC

AGCACTGGTGACCTAATGAAGAAAAATTATTTACATAATTTCTGTAGTCAAGTTCCAT

CAGTGCTTGGGCAATCTTCCCCCAAGGTAGTAGCAAGCCTGCCATCTATCAGTGTTCC

TTTTGGTGGTGCAAGACCCAAGCAACCTTCTAATCTTAAACTTCAAATTCCAAAGCCA

TTATCAGACCATTTACAAAATGACTTTCCTGCAAACAGTGGAAATAATACTAAAAATA

AAAATGATATTCTTGGGAAAGCAAAATTAGGGGAAAACTCAGCAACCAATGTATGCAG

TCCATCTTTGGGAAACATCTCTAATGTCGATACAAATGGGGAACATTTAGAAAGTTAT

GAGGCTGAGATCTCCACTAGACCATGCCTTGCATTAGCTCCAGATAGCCCAGATAATG

ATCTCAGAGCTGGTCAGTTTGGAATTTCTGCCAGAAAGCCATTCACCACGCTGGGTGA

GGTGGCTCCAGTATGGGTACCGGATTCTCAGGCTCCAAATTGCATGAAATGTGAAGCC

AGGTTTACATTCACCAAAAGGAGGCATCACTGCAGAGCATGTGGGAAGGTTTTCTGTG

CTTCCTGCTGTAGCCTGAAATGTAAACTGTTATACATGGACAGAAAGGAAGCTAGAGT

GTGTGTAATCTGCCATTCAGTGCTAATGAATGCTCAAGCCTGGGAGAACATGATGAGT

GCCTCAAGCCAGAGCCCTAACCCTAACAATCCTGCTGAATACTGTTCTACTATCCCTC

CCTTGCAGCAAGCTCAGGCCTCAGGAGCTCTGAGCTCTCCACCTCCCACTGTGATGGT

ACCTGTGGGAGTTTTAAAGCACCCTGGAGCAGAAGTGGCTCAGCCCAGAGAGCAGAGG

CGAGTTTGGTTTGCTGATGGGATCTTGCCCAATGGAGAAGTTGCTGATGCAGCCAAAT

TAACAATGAATGGAACTTCCTCTGCAGGAACCCTGGCTGTGTCACACGACCCAGTCAA

GCCAGTAACTACCAGTCCTCTACCAGCAGAGACGGATATTTGTCTATTCTCTGGGAGT

ATAACTCAGGTTGGAAGTCCTGTTGGAAGTGCAATGAATCTTATTCCTGAAGATGGCC

TTCCTCCCATTCTCATCTCCACTGGTGTAAAAGGAGACTATGCTGTGGAAGAGAAACC

ATCACAGATTTCAGTAATGCAGCAGTTGGAGGATGGTGGCCCTGACCCACTTGTATTT

GTTTTAAATGCAAATTTGTTGTCAATGGTTAAAATTGTAAATTATGTGAACAGGAAGT

GCTGGTGTTTCACAACCAAGGGAATGCATGCAGTGGGTCAGTCTGAGATAGTCATTCT

TABLE 1-continued hSARA1 - Sequence ID NO:1

TCTACAGTGTTTACCGGATGAAAAGTGTTTGCCAAAGGATATCTTTAATCACTTTGTG

CAGCTTTATCGGGATGCTCTGGCAGGGAATGTGGTGAGCAACTTGGGACATTCCTTCT

TCAGTCAAAGTTTCCTTGGCAGTAAAGAACATGGTGGATTCTTATATGTGACATCTAC

CTACCAGTCACTGCAAGACCTAGTACTCCCAACCCCACCTTACTTGTTTGGGATTCTT

ATCCAGAAATGGGAAACTCCTTGGGCTAAAGTATTTCCTATCCGTCTGATGTTGAGAC

TTGGAGCTGAATATCGACTTTATCCATGCCCACTATTCAGTGTCAGATTTCGGAAGCC

ATTGTTTGGAGAGACGGGGCATACCATCATGAATCTTCTTGCAGACTTCAGAAATTAC

CAGTATACCTTGCCAGTAGTTCAAGGTTTGGTGGTTGATATGGAAGTTCGGAAAACTA

GCATCAAAATTCCCAGCAACAGATACAATGAGATGATGAAAGCCATGAACAAGTCCAA

TGAGCATGTCCTGGCAGGAGGTGCCTGCTTCAATGAAAAGGCAGACTCTCATCTTGTG

TGTGTACAGAATGATGATGGAAACTATCAGACCCAGGCTATCAGTATTCACAATCAGC

CCAGAAAAGTGACTGGTGCCAGTTTCTTTGTGTTCAGTGGCGCTCTGAAATCCTCTTC

TGGATACCTTGCCAAGTCCAGTATTGTGGAAGATGGTGTTATGGTCCAGATTACTGCA

GAGAACATGGATTCCTTGAGGCAGGCACTGCGAGAGATGAAGGACTTCACCATCACCT

GTGGGAAGGCGGACGCGGAGGAACCCCAGGAGCACATCCACATCCAGTGGGTGGATGA

TGACAAGAACGTTAGCAAGGGTGTCGTAAGTCCTATAGATGGGAAGTCCATGGAGACT

ATAACAAATGTGAAGATATTCCATGGATCAGAATATAAAGCAAATGGAAAAGTAATCA

GATGGACAGAGGTGTTTTTCCTAGAAAACGATGACCAGCACAATTGCCTCAGTGATCC

TGCAGATCACAGTAGATTGACTGAGCATGTTGCCAAAGCTTTTTGCCTTGCTCTCTGT

CCTCACCTGAAACTTCTGAAGGAAGATGGAATGACCAAACTGGGACTACGTGTGACAC

TTGACTCAGATCAGGTTGGCTATCAAGCAGGGAGCAATGGCCAGCCCCTTCCCTCGCA

GTACATGAATGATCTGGATAGCGCCTTGGTGCCGGTGATCCATGGAGGGGCCTGCCAG

CTTAGTGAGGGCCCCGTTGTCATGGAACTCATCTTTTATATTCTGGAAAACATCGTAT

AAACAGAGAAGACTTCATTTTTTTCTGTTCAGACTTGTTGCAACAGCAGTCATACCCA

AATCATTTGCACTTTAAAACTGGAAGATTAAGCTTTTGTTAACACTATTAATGGGGTG

GGGAATAGGGTGGGAGTGGGGGTTTGGGAGACGGGTGGGAAAGGGTGGTTGGGGGGAC

CGATGTTCCATAATTCTAAGTCTTCTATGCATTGTCCACCAAGAAGATCTGGGCAGCT

TCTGTTCCTGCACAACAGTTATGCTATCCTTGCAGCTAATCCCCTTCTGTTACTGTTT

AGACAAGAATTCCGCTCCTCTCTCAAGATTTACTTATGGTCATGTGCTCAGAAATGCT

CAAATGGGTACAACCATCACCAAGGGTGGGATGGGAGGGCAGAGGGGAAATAAAATAT

AAAGCATCAAAAAAAAAAAAAAAAA

TABLE 2 hSARA1 - Sequence ID NO:2

MWIDENAVAEDQLIKRNYSWDDQCSAVEVGEKKCGNLACLPDEKNVLVVAVMHNCDKR

TLQNDLQDCNNYNSQSLMDAFSCSLDNENRQTDQFSFSINESTEKDMNSEKQMDPLNR

PKTEGRSVNHLCPTSSDSLASVCSPSQLKDDGSIGRDPSMSAITSLTVDSVISSQGTD

GCPAVKKQENYIPDEDLTGKISSPRTDLGSPNSFSHMSEGILMKKEPAEESTTEESLR

TABLE 2-continued hSARA1 - Sequence ID NO:2

SGLPLLLKPDMPNGSGRNNDCERCSDCLVPNEVRADENEGYEHEETLGTTEFLNMTEH

FSESQDMTNWKLTKLNEMNDSQVNEEKEKFLQISQPEDTNGDSGGQCVGLADAGLDLK

GTCISESEECDFSTVIDTPAANYLSNGCDSYGMQDPGVSFVPKTLPSKEDSVTEEKEI

EESKSECYSNIYEQRGNEATEGSGLLLNSTGDLMKKNYLHNFCSQVPSVLGQSSPKVV

ASLPSISVPFGGARPKQPSNLKLQIPKPLSDHLQNDFPANSGNNTKNKNDILGKAKLG

ENSATNVCSPSLGNISNVDTNGEHLESYEAEISTRPCLALAPDSPDNDLRAGQFGISA

RKPFTTLGEVAPVWVPDSQAPNCMKCEARFTFTKRRHHCRACGKVFCASCCSLKCKLL

YMDRKEARVCVICHSVLMNAQAWENMMSASSQSPNPNNPAEYCSTIPPLQQAQASGAL

SSPPPTVMVPVGVLKHPGAEVAQPREQRRVWFADGILPNGEVADAAKLTMNGTSSAGT

LAVSHDPVKPVTTSPLPAETDICLFSGSITQVGSPVGSAMNLIPEDGLPPILISTGVK

GDYAVEEKPSQISVMQQLEDGGPDPLVFVLNANLLSMVKIVNYVNRKCWCFTTKGMHA

VGQSEIVILLQCLPDEKCLPKDIFNHFVQLYRDALAGNVVSNLGHSFFSQSFLGSKEH

GGFLYVTSTYQSLQDLVLPTPPYLFGILIQKWETPWAKVFPIRLMLRLGAEYRLYPCP

LFSVRFRKPLFGETGHTIMNLLADFRNYQYTLPVVQGLVVDMEVRKTSIKIPSNRYNE

MMKAMNKSNEHVLAGGACFNEKADSHLVCVQNDDGNYQTQAISIHNQPRKVTGASFFV

FSGALKSSSGYLAKSSIVEDGVMVQITAENMDSLRQALREMKDFTITCGKADAEEPQE

HIHIQWVDDDKNVSKGVVSPIDGKSMETITNVKIFHGSEYKANGKVIRWTEVFFLEND

DQHNCLSDPADHSRLTEHVAKAFCLALCTQLKLLKGDGMTKLGLRVTLDSDQVGYQAG

SNGQHLPSQYMNDFDSDLVKMIHGGACQLSEGPVVMELIFYILENIV

TABLE 3 human SARA2 - Sequence ID NO:3

ACTCCCGGCCGGGGTAGCTCTTCACTCCTCAGCGCGACGTCGTGTCGAGTTCCCAAAA

AGCTCCGCAGGGGCTGTAGGGAGGTGATCTCATCCATTAACAGCTGTGTGTTGCCAGT

TCCCAAATCTTTATCTATCTCAGACTTCTCTCCTGCATTCCAGATTCTTATATTCAGC

TGCCTTTTGGATATCTCTCCCAGGATGTTCTCAAGGCATACAAGAATTAAATTCTGAA

TAAGTCTGCAGGTAGGATGGACAGTTATTTTAAAGCAGCTGTCAGTGACTTGGACAAA

CTCCTTGATGATTTTGAACAGAACCCAGATGAACAAGATTATCTCGCAGATGTACAAA

ATGCATATGATTCTAACCACTGCTCAGTTTCTTCAGAGTTGGCTTCCTCACAGCGAAC

TTCATTGCTCCCAAAAGACCAAGAGTGCGTTAATAGTTGTGCCTCATCAGAAACAAGC

TATGGAACAAATGAGAGTTCCCTGAATGAAAAAACACTCAAGGGACTTACTTCTATAC

AAAATGAAAAAAATGTAACAGGACTTGATCTTCTTTCTTCTGTGGATGTGGTACTTC

AGATGAAATCCAGCCGTTATATATGGGACGATGTAGTAAACCTATCTGTGATCTGATA

AGTGACATGGGTAACTTAGTTCATGCAACCAATAGTGAAGAAGATATTAAAAAATTAT

TGCCAGATGATTTTAAGTCTAATGCAGATTCCTTGATTGGATTGGATTTATCTTCAGT

GTCAGATACTCCCTGTGTTTCTTCAACAGACCATGATAGTGATACTGTCAGAGAACAA

CAGAATGATATCAGTTCTGAATTACAAAATAGAGAAATCGGAGGAATCAAAGAATTGG

GTATAAAAGTAGATACAACACTTTCAGATTCCTATAATTACAGTGGAACAGAAAATTT

TABLE 3-continued human SARA2 - Sequence ID NO:3

AAAAGATAAAAAGATCTTTAATCAGTTAGAATCAATTGTTGATTTTAACATGTCATCT

GCTTTGACTCGACAAAGTTCCAAAATGTTTCATGCCAAAGACAAGCTACAACACAAGA

GCCAGCCATGTGGATTACTAAAAGATGTTGGCTTAGTAAAAGAGGAAGTAGATGTGGC

AGTCATAACTGCCGCAGAATGTTTAAAAGAAGAGGGCAAGACAAGTGCTTTGACCTGC

AGCCTTCCGAAAAATGAAGATTTATGCTTAAATGATTCAAATTCAAGAGATGAAAATT

TCAAATTACCTGACTTTTCCTTTCAGGAAGATAAGACTGTTATAAAACAATCTGCACA

AGAAGACTCAAAAAGTTTAGACCTTAAGGATAATGATGTAATCCAAGATTCCTCTTCA

GCTTTACATGTTTCCAGTAAAGATGTGCCGTCCTCATTGTCCTGTCTTCCTGCGTCTG

GGTCTATGTGTGGATCATTAATTGAAAGTAAAGCACGGGGTGATTTTTTACCTCAGCA

TGAACATAAAGATAATATACAAGATGCAGTGACTATACATGAAGAAATACAGAACAGT

GTTGTTCTAGGTGGGGAACCATTCAAAGAGAATGATCTTTTGAAACAGGAAAAATGTA

AAAGCATACTCCTTCAGTCATTAATTGAAGGGATGGAAGACAGAAAGATAGATCCTGA

CCAGACAGTAATCAGAGCTGAGTCTTTGGATGGTGGTGACACCAGTTCTACAGTTGTA

GAATCTCAAGAGGGGCTTTCTGGCACTCATGTCCCAGAGTCTTCTGATTGTTGTGAAG

GTTTTATTAATACTTTTTCAAGCAATGATATGGATGGGCAAGACTTAGATTACTTTAA

TATTGATGAAGGCGCAAAAAGTGGCCCACTAATTAGTGATGCTGAACTTGATGCCTTT

CTGACAGAACAGTATCTTCAGACCACTAACATAAAGTCTTTTGAAGAAAATGTAAATG

ACTCTAAATCGCAAATGAATCAGATAGATATGAAAGGCTTAGATGATGGAAACATCAA

TAATATATATTTCAATGCAGAAGCAGGAGCTATTGGGGAAAGTCATGGTATTAATATA

ATTTGTGAAACAGTTGATAAACAAAATACAATAGAAAATGGCCTTTCTTTAGGAGAAA

AAAGCACTATTCCAGTTCAACAAGGGTTACCTACCAGTAAGTCTGAGATTACAAATCA

ATTATCAGTCTCTGATATTAACAGTCAATCTGTTGGAGGGGCCAGACCTAAGCAATTG

TTTAGCCTTCCATCAAGAACAAGGAGTTCAAAGGACCTGAATAAGCCAGATGTTCCAG

ATACAATAGAAAGTGAACCCAGCACAGCAGATACCGTTGTTCCAATCACTTGTGCTAT

AGATTCTACAGCTGATCCACAGGTTAGCTTCAACTCTAATTACATTGATATAGAAAGT

AATTCTGAAGGTGGATCTAGTTTCGTAACTGCAAATGAAGATTCTGTACCTGAAAACA

CTTGCAAAGAAGGCTTGGTTTTGGGCCAGAAACAGCCTACTTGGGTTCCTGATTCAGA

AGCTCCAAACTGTATGAACTGCCAAGTCAAATTTACTTTTACCAAACGGCGACACCAT

TGCCGAGCATGTGGGAAAGTATTTTGTGGTGTCTGTTGTAATAGGAAGTGTAAACTGC

AATATCTAGAAAAGGAAGCAAGAGTATGTGTAGTCTGCTATGAAACTATTAGTAAAGC

TCAGGCATTTGAAAGGATGATGAGTCCAACTGGTTCTAATCTTAAGTCTAATCATTCT

GATGAATGTACTACTGTCCAGCCTCCTCAGGAGAACCAAACATCCAGTATACCTTCAC

CAGCAACTTTGCCAGTCTCAGCACTTAAACAACCAGGTGTTGAAGGACTATGTTCCAA

AGAACAGAAGAGAGTATGGTTTGCAGATGGTATATTGCCCAATGGTGAAGTTGCAGAT

ACAACAAAATTATCATCTGGAAGTAAAAGATGTTCTGAAGACTTTAGTCCTCTCTCAC

CTGATGTGCCTATGACAGTAAACACAGTGGATCATTCCCATTCTACTACAGTGGAAAA

GCCAAACAATGAGACAGGAGATATTACAAGAAATGAGATAATTCAGAGTCCTATTTCT

CAGGTTCCATCAGTGGAAAAATTGTCTATGAACACAGGAAATGAGGGGTTACCTACTT

CTGGTTCATTTACACTAGATGATGATGTTTTTGCAGAAACTGAAGAACCATTTAGTCC

TABLE 3-continued human SARA2 - Sequence ID NO:3

```
TACTGGTGTCTTAGTTAACAGCAATTTACCTATTGCTAGTATTTCAGATTATAGGTTA
CTGTGTGATATTAACAAGTATGTCTGCAATAAGATTAGTCTTCTACCTAATGATGAGG
ACAGTTTGCCCCCACTTCTGGTTGCATCTGGAGAAAAGGGATCAGTGCCTGTAGTAGA
AGAACATCCATCTCATGAGCAGATCATTTTGCTTCTTGAAGGTGAAGGCTTTCATCCT
GTTACATTTGTCCTAAATGCTAATCTACTCGTGAATGTCAAATTCATATTTTATTCCT
CAGACAAATATTGGTACTTTTCAACCAATGGATTGCATGGCTTGGGACAGGCAGAAAT
TATTATTCTATTGTTATGTTTGCCAAATGAAGATACTATTCCTAAGGACATCTTCAGA
CTATTTATCACCATATATAAGGATGCTCTAAAAGGAAAATACATAGAAAACTTGGACA
ATATTACCTTTACTGAGAGTTTTCTCAGTAGCAAGGATCACGGAGGATTCCTGTTTAT
TACACCTACTTTTCAGAAACTTGATGATCTCTCATTACCAAGTAATCCTTTTCTTTGT
GGAATTCTTATCCAGAAGCTTGAGATTCCCTGGGCAAAGGTTTTTCCTATGCGTTTAA
TGTTGAGATTGGGTGCAGAATATAAAGCATATCCTGCTCCTCTAACAAGCATCAGAGG
CCGAAAACCTCTTTTTGGAGAAATAGGACACACTATTATGAACTTACTTGTTGACCTT
CGAAATTACCAGTATACCTTGCATAATATAGATCAACTGTTGATTCATATGGAAATGG
GAAAAAGCTGCATAAAAATACCACGGAAAAAGTACAGTGATGTAATGAAAGTACTAAA
TTCTTCCAATGAGCATGTCATTAGCATTGGAGCAAGTTTCAGTACAGAAGCAGATTCT
CATCTAGTCTGTATACAGAATGATGGAATTTATGAAACACAGGCCAACAGTGCCACTG
GCCATCCTAGAAAAGTGACAGGTGCAAGTTTTGTGGTATTCAATGGAGCTCTAAAAAC
ATCTTCAGGATTTCTTGCTAAGTCCAGCATAGTTGAAGATGGCTTAATGGTACAAATA
ACTCCAGAGACCATGAATGGCTTGCGGCTAGCTTTACGAGAACAGAAAGACTTTAAAA
TTACATGTGGGAAAGTTGATGCAGTAGACCTGAGAGAATACGTGGATATCTGCTGGGT
AGATGCTGAAGAAAAGGAAACAAAGGAGTTATCAGTTCAGTGGATGGAATATCATTA
CAAGGATTTCCAAGTGAAAAAATAAAACTGGAAGCAGATTTTGAAACCGATGAGAAGA
TTGTAAAATGTACCGAGGTGTTCTACTTTCTAAAGGACCAGGATTTATCTATTTTATC
AACTTCTTATCAGTTTGCAAAAGAAATAGCCATGGCTTGTAGTGCTGCGCTGTGCCCT
CACCTGAAAACTCTAAAAAGTAATGGGATGAATAAAATTGGACTCAGAGTTTCCATTG
ACACTGATATGGTTGAATTTCAGGCAGGATCTGAAGGCCAACTTCTGCCTCAGCATTA
TCTAAATGATCTTGATAGTGCTCTGATACCTGTGATCCATGGTGGGACCTCCAACTCT
AGTTTACCATTAGAAATAGAATTAGTGTTTTTCATTATAGAACATCTTTTTTAGTGAA
AGAATGTGCCATATTACATATTGCAACCTAATTTGTTAAAACTAACTCCAGCACTAAA
GCTGAAATGCCACAAACACTAAAAGTATAAATATGTCTGATTTTTGAAACACATAAGC
TTTGCTCTTTAGGCAGGAATGATCTTTTCAAATCATTAGCACAATATTTAAATATCTA
AAAATTTAAGAGATCCATACTTTCTGTAGCTTTACAATTAATTTAAGTACTAAAAAGA
CAAGGATTTCTTTTAAGAAATTTATAGCATTTACTGTGTTATTTAAATGCTAAGCCAA
AGTATCTGCACTTAGGTATACCTCTTTATGCCAATAATGATTTTAATGAAGGCTCTTT
TCAGATGTAACCTTATGAAGGAAATATCTGCTTTGTGTATATGCCAGTTAGAATACTG
GTTTCTAAAGTCTGTCAAATTGTATTTCAGTGGCACAAAAACCAGTTTTGAGGTCTTA
GACTTATAATTCTTTGAATAAAACTGATAACTTATTTGTATAATTGGAGTGGAGACCT
```

TABLE 3-continued human SARA2 - Sequence ID NO:3

ACCTCCATAATTAGATAAACTCTTTTTGGATTATAATCAGAATTTTGCCTTTTTTCTT
CTCAAATTATTACATATGTATGTATTATATATCCACATATATAGTTTTCCCTGATTAA
ATGGATATTAAAATAATTGCGGGTGCTTCAGGACTTTTTGCTTCTATATTTAAGTATA
TTGTTTTTATAGCAAGAACATATTCTGAATGTTTATAAATCTTTAATAATTTATATG
TAGGTAATATTTTTGTATCACAATGCATTATTTTTTTCCTCCTTTCCTTCCAAACTA
TACCACTGTATTTACCACTTCTAAGAGTGACTGACGACGGGCCAGATGACCCTTGAAG
TAGTCATTATGTAGCAATAAATGAAGCCTGAAACAGGTTTTTTTACTTCCACTTTAAT
CCTTAGAAATTTCTTGGCAACTTCGCATATTTTCATTGACACTGGTGTATAAGTATAA
ATTTAAATGAACTAATTACTTTTGCATATTTTAAATTCTTTATATGGTAGTTATTTTT
TATAACAGGATATTAACATAAGTTAAATCCTATGTATTTGAAATTGTTACAGAGCTTT
CCTCTTTACTTCAAACAGCAAAAAAGTGGGGGGCATATTGTAGTCCTGTCATTTAAGT
TATGTAAAAAATTTAATCATTATTTTGATGCTTTAAACATTCTCATGTGTAATATATG
TTTTTGTATCAAAAACACTCATATATTTCAAGAAAAAGAAATTATGTTAAATAGCCCT
GTTTTAAGAAAAATATTTATGAAGCATCTCAACTTGAAGATCAAGTCAAAGTTATAAC
TCAGGATCTGAGGTCTCAAGCTAGGAGAGACTGAGAATTTTAATCAGTTTGGGCATAT
AGTTTGGACTGAATCACATCTGTAGTACTTAGCCAAAGACAATTTGGAGGAGAATATC
AGCCTTCTGGAAGTAGCTACTTCCTGAACAATGTAAAGTGTCGCAGATATTCAATAAA
ATGGCAACCTGTTATAATTTGTGAAATTTATTGAAATGGTGTAAGATGAAAACAATTG
CATATCAAACCCAATTTATGTTTTCTAAATATAGTGTATGTATTCTGCCATGTAAGTA
ATTGAACAGTCTTAAAATAACCAAATGGTAGAGGGCTGTTCCATGATGGGACAGCTTT
GGATTTGTTTTCATAAAATCTCTACATTCAATAAAAATTGGAATTATGTGCCTGAAGT
TTGGAGGCACATTTTGAAGT

TABLE 4 human SARA2 - Sequence ID NO:4

MDSYFKAAVSDLDKLLDDFEQNPDEQDYLQDVQNAYDSNHCSVSSELASSQRTSLLPK
DQECVNSCASSETSYGTNESSLNEKTLKGLTSIQNEKNVTGLDLLSSVDGGTSDEIQP
LYMGRCSKPICDLISDMGNLVHATNSEEDIKKLLPDDFKSNADSLIGLDLSSVSDTPC
VSSTDHDSDTVREQQNDTSSELQNREIGGIKELGIKVDTTLSDSYNYSGTENLKDKKI
FNQLESIVDFNMSSALTRQSSKMFRAKDKLQHKSQPCGLLKDVGLVKEEVDVAVITAA
ECLKEEGKTSALTCSLPKNEDLCLNDSNSRDENFKLPDFSFQEDKTVIKQSAQEDSKS
LDLKDNDVIQDSSSALHVSSKDVPSSLSCLPASGSMCGSLIESKARGDFLPQHEHKDN
IQDAVTIHEEIQNSVVLGGEPFKENDLLKQEKCKSILLQSLIEGMEDRKIDPDQTVIR
AESLDGGDTSSTVVESQEGLSGTHVPESSDCCEGFINTFSSNDMDGQDLDYFNIDEGA
KSGPLISDAELDAFLTEQYLQTTNIKSFEENVNDSKSQMNQIDMKGLDDGNINNIYFN
AEAGAIGESHGINIICETVDKQNTIENGLSLGEKSTIPVQQGLPTSKSEITNQLSVSD
INSQSVGGARPKQLFSLPSRTRSSKDLNKPDVPDTIESEPSTADTVVPITCAIDSTAD
PQVSFNSNYIDIESNSEGGSSFVTANEDSVPENTCKEGLVLGQKQPTWVPDSEAPNCM

TABLE 4-continued

| human SARA2 - Sequence ID NO:4 |
|---|
| NCQVKFTFTKRRHHCRACGKVFCGVCCNRKCKLQYLEKEARVCVVCYETISKAQAFER |
| MMSPTGSNLKSNHSDECTTVQPPQENQTSSIPSPATLPVSALKQPGVEGLCSKEQKRV |
| WFADGILPNGEVADTTKLSSGSKRCSEDFSPLSPDVPMTVNTVDHSHSTTVEKPNNET |
| GDITRNEIIQSPISQVPSVEKLSMNTGNEGLPTSGSFTLDDDVFAETEEPSSPTGVLV |
| NSNLPIASISDYRLLCDINKYVCNKISLLPNDEDSLPPLLVASGEKGSVPVVEEHPSH |
| EQIILLLEGEGFHPVTFVLNANLLVNVKFIFYSSDKYWYFSTNGLHGLGQAEIIILLL |
| CLPNEDTIPKDIFRLFITIYKDALKGKYIENLDNITFTESFLSSKDHGGFLFITPTFQ |
| KLDDLSLPSNPFLCGILIQKLEIPWAKVFPMRLMLRLGAEYKAYPAPLTSIRGRKPLF |
| GEIGHTIMNLLVDLRNYQYTLHNIDQLLIHMEMGKSCIKIPRKKYSDVMKVLNSSNEH |
| VISIGASFSTEADSHLVCIQNDGIYETQANSATGHPRKVTGASFVVFNGALKTSSGFL |
| AKSSIVEDGLMVQITPETMNGLRLALREQKDFKITCGKVDAVDLREYVDICWVDAEEK |
| GNKGVISSVDGISLQGFPSEKIKLEADFETDEKIVKCTEVFYFLKDQDLSILSTSYQF |
| AKETAMACSAALCPHLKTLKSNGMNKIGLRVSIDTDMVEFQAGSEGQLLPQHYLNDLD |
| SALIPVIHGGTSNSSLPLEIELVFFIIEHLF |

TABLE 5

| XSARA1 - Sequence ID NO:5 |
|---|
| CTGTAAGTTTGACTATGTAGGAAAGCATTTCTGTTATCTATGAAGTATGTTTTAGAGT |
| CAGACCAATAACTAAACGGTTTTCTTTTTTTTGTTTATTTCCCCTCAGATGAGACTGT |
| CTCTCCAAAGCTATTAGATGCTAAGTGGAATCAAATCTTAGAACCGCATTCACATAAA |
| GTCGCTGATAACTCCGCCCTTGACAATGTCTGTAAATCAATCATTGCTATTGAAGCTC |
| ATCTCAAAGTCAGGTCACCCGGCTTGTCAGCCCTTGTGAGGTCCACATATGTGAATGG |
| AGAAGTAGGTATTGTGGCACCTGAAATGCCCAAAATGGTGATAGGAGACACCATTATG |
| GCAGAGGATTCACTTTTTAACAACACTGGTCCCTCTGAAATTGTATGCAACCCATCTA |
| CTGTGGAGAGTCAAAGTTTACAAGCTTTAGATGATCAATCAGTGAATATTCACAATGA |
| AAAAAGTGTTCTGCTCGCTGATGGCTTTTCACCATGCAGTAGCCCCAAAAGTATTATA |
| AACTTTGACTGCTTGACCATGGATAACGAAATGCCTTTGCACAGTCAAATGAGTGTTG |
| ATGACAATGACAAAGAAACTGTAACAATTTCAGTCCTTCCAACAATCATACAGGATAC |
| TAGTAACGTAAGCACAGACCCAGCTATCAATAAACCTGGCACTAAAGAACCCCATAGA |
| GCATTAAAGGAAACCACATCAGTTATTCTGCCTGAAATAAAGCCTTACTCCACATGTG |
| CTGCCCTTTCGTTTGAAAATAACAATAAGGTTCCCAGTTATCAATTAAATAATACAGA |
| TCTACTCAGCGTTTCACCAGTGGTTGAAGCATGTAGTGAGCAGCAGCAAAAACATACA |
| TCTTCCTTGCATGAAGAAAAACTTTTTGAAGGTGTTTCTGCAACGGAGTCCTTTGCAG |
| CCACTGCTGCGGAAACTGTACTGGATAATGAGGCTCTCCGTAGTGCTGAATTCTTTGA |
| CATTGTTGTAAAGAACTTTTCTGACTCTTGTGTGATTAATGGCGACTTGACTAAAAGT |
| TGTGGCCTCTCTCAAGAAAGCAATGAAAAGTTTTGTGCAAGTAAAGAGTTTGAAGGAG |
| GGGTAGATGCTAATGTCTTGTTGGAAAATGCATGTGTAGCTTATAAAGAAGCAATAGA |
| TTTGCCTGAAGAAAATGGAACTAATGCACCAATGTCTCTGTACAATGGGTGTGATTCC |

TABLE 5-continued

XSARA1 - Sequence ID NO:5

TATGGAATGAAAAACCCAGCCGTAGCTCAAAACCCAAAGAATTTACCTTCAAAAGAAG

ATTCTGTGACAGAAGAAAAAGAAATTGAAGAAAGCAAGTCAGAATACTATACTGGTGT

TTATGAACAACAAAGAGAAGATGATGTTACAGAGAGAGGTGGACTTCTGTTAAATGCT

AAGGCTGACCAAATGAAGAACAATTTGCATAGTCTTTGTAATCAGGTTCCATCCATGC

ATGGGCAAACATCACCAAAAAAGGGCAAGATTGTGCAATCTCTCAGTGTTCCATACGG

TGGAGCACGCACTAAGCAGCCAACTCATCTCAAACTCCATATTCCAAAGCCATTGTCT

GAAATGTTGCAGAGCGATCTCATTCCTCCAAATGCTGGCTGCAGCTCTAAATACAAAA

ATGACATGTTAAACAAATCAAATCAGGGGATAACCTGATTTCAGAATCACTGCGTGA

GGATTCTGCAGTGCGCAGCCCTGTTACTGATGCTAATGGTGATTTCCCTGGAGAATAC

AGGGGACCTGGCAGCTTGTGCCTTGCAGTGTCTCCAGACAGCCCAGACAACGATCTGC

TTGCCGGGCAGTTTGGGGTACCCATCTCTAAGCCATTTACTACTCTAGGGGAAGTGGC

TCCAGTCTGGGTGCCAGATTCCCAAGCACCAAACTGCATGAAGTGCGAGGCCAGATTT

ACATTTACCAAAAGGAGGCATCACTGCCGAGCTTGTGGAAAGGTGTTCTGTGCTGCTT

GTTGCAGTCTAAAATGCAAACTACAGTACATGGATAAAAAGGAGGCTCGTGTGTGTGT

TATTTGTCATTCTGTGCTTATGAATGCTCAAGCATGGGAGAACATGTTAAGTGCATCG

GTCCAAAGCCCAAATCCAAATAATCCTGCTGAATACTGCTCAACTATCCCTCCGATGC

AGCAGGCACAAGCTTCAGGAGCACTGAGTTCCCCACCTCCCACTGTCATGGTGCCAGT

GGGTGTGTTAAAACATCCAGGAACTGAAGGGTCACAGTCAAAGGAACAGCGCCGTGTT

TGGTTTGCTGATGGAATATTACCCAACGGAGAGACTGCTGACTCAGATAATGCAAACG

TAACTACAGTGGCTGGGACACTTACTGTGTCACATACCAACAATTCCACATCTTCAGA

GTCTGAGAACACCTCTGGATTCTGTGGAAGTATAACTCAGGTTGGCAGTGCAATGAAC

CTTATTCCAGAAGATGGGCTTCCTCCTATACTAATCTCTACTGGAGTAAAAGGAGATT

ACGCAGTTGAGGAACGCCCTTCCCAGATGTCTGTGATGCAGCAACTAGAGGAAGGAGG

ACCAGATCCTTTGGTTTTTGTTCTAAATGCAAATCTTTTGGCCATGGTTAAGATCGTG

AACTATGTTAACAGGAAATGCTGGTGCTTTACTACAAAGGGAATGCATGCAGTGGGCC

AGGCTGAGATCGTAATCCTGTTGCAGTGCCTGCCTGATGAGAAGTGCCTGCCGAGGGA

CCTGTTTAGCCATTTTGTTGAGCTGTATCAGGAGGCAATTGCAGGTAATGTAGTGGGG

AACCTGGGGCATTCCTTCCTCAGCCAGAGTTTCCTGGGTAGTAAGGATCATGGTGGAT

TTCTTTATGTTGCACCAACCTACCAGTCCCTCCAGGACCTGGTTCTTCCTGCAGAGCC

GTACTTGTTTGGAATCCTTATTCAAAAGTGGGAGACTCCATGGGCCAAAGTGTTCCCC

ATTCGGCTTATGCTGCGTTTAGGTGCAGAATACAGATTGTACCCATGTCCACTCTTCA

GTGTTCGATACAGAAAACCTCTGTTTGGGAAACCGGACACACCATCATTAATGTTCT

AGCCGATTTCAGAAACTATCAGTATACTCTGCCAGTGGTGCAGGGCTTGGTGGTGGAT

ATGGAAGTCAGAAAAACTAGCATTAAAATCCCCAGCAATAGATACAATGAGATGATGA

AAGCAATGAACAAATCCAATGAGCATGTGTTGGCCATAGGAGCATGCTTCAACCAGAT

GGCAGACTCTCACCTTGTGTGTGTGCAAAACGATGATGGCAATTACCAGACCCAGGCA

ATTAGTATCCACAAACAACCACGTAAAGTGACCGGGGCCAGCTTCTTTGTCTTCAGTG

GTGCACTAAAGTCTTCTTCCGGATACCTGGCCAAATCCAGCATAGTAGAAGATGGGGT

AATGGTTCAGATCACCGCAGAGAGCATGGATGCCCTCAGACAGTCCCTTCGGGAGATG

TABLE 5-continued

XSARA1 - Sequence ID NO:5

AAGGATTTCACCATTACATGTGGAAAAGCTGATGCAGAGGAGTCACAGGAACATGTCT

ATGTCCAGTGGGTGGAGGATGACAAGAACTTTAACAAAGGAGTTTTTAGTCCAATCCA

TGGCAAATCAATGGAGTCTGTGACCAGCGTCAAGATTTTTCATGGCTCAGAATACAAA

GCTAGTGGAAAAATAATTCGCTGGATAGAGGTCTTCTTTCTGGACAATGAGGAGCAAC

AGAGTGGCCTGAGTGACCCTGCTGATCACAGCCGACTCACTGAAAATGTGGCCAAAGC

ATTCTGTTTAGCGCTTTGCCCACACCTCAAGCTACTGAAGGAAGATGGAATGACCAGG

TTAGGTCTGCGGGTGTCACTGGACTCAGACCAGGTTGGATACCAAGCTGGGAGCAATG

GGCAACTCCTGCCTGCCCGATACACCAATGATTTGGATGGTGCTTTGGTACCAGTGAT

ACACGGGGCACATGCCAGTTAAGTGAAGGGCCTGTCAGTATGGAGCTGATATTTTAT

ATCCTTGAGAACATCTCCTAGGAAAGACACATGTGTCTCCTCACAAACTGCCATCGCC

CAAACCATTTGCACTTTAACCGCAAAAGATTCATTTTTCTTTTCTTTTGCTAACACTA

GTATTAGGTCAGGGTGCGAGAGGCAGACACCTGAACTCTTAAACCTTCTATGCATTTT

CACAGTAAGGATCAAGCTGCAGCTGGGAATTTCCTGTTACTAATCCAATGTGGGACGT

TAGAAGTGATCGGTGGCACTGACTATCTAGCTGTTCAACCTTCTCTGGCTCCTCTAAG

GACTCTAGTGCCAGGGGGTGAGACATTCAAGTTTAAAACGAAAACTCTAAATACAATC

AGGAATCTCACTCTGACCTCATTTAAATCATCACTGCGACTTTTTTTCCTGCTCGCAT

TCTTTATTTTGCATCTTACTCAAGTTTACATTGTCAAGACCAGCCTAAGCCTTCAGTC

CTTTCTCAATTAAACTACTCGTGCATGGCAAGGAGACTTTCGTTGCACAGCCTGAAAT

ATACCAATCACTTCCCAAACCACAAGCATGAATCCAACGTTTTCCTGACTGGTTGGCT

CTGCTGTGAAAGGGACAGCAATATTATTTTTCTACAGTTGACAAAACTTTTGTCTATG

TCTGTGTCTCTCATGGGGATTTGTTGCCTGATGGGCAGCCTCCGGAGAGAAGAATTC

CACCCGTGTGTAATATACAGTCTAAGTGTATGGTCTGCTATGTAACACCTGTTGCGCA

GTGCAAATGCACTGACTCTCTGGAAGGCTATAGAGTTTTAAAAACGGTTAGTCTTTTA

AAAAAAAAA

TABLE 6

XSARA1 - Sequence ID NO:6

MPKMVIGDTIMAEDSLFNNTGPSEIVCNPSTVESQSLQALDDQSVNIHNEKSVLLADG

FSPCSSPKSIINFDCLTMDNEMPLHSQMSVDDNDKETVTISVLPTIIQDTSNVSTDPA

INKPGTKEPHRALKETTSVILPEIKPYSTCAALSFENNNKVPSYQLNNTDLLSVSPVV

EACSEQQQKHTSSLHEEKLFEGVSATESFAATAAETVLDNEALRSAEFFDIVVKNFSD

SCVINGDLTKSCGLSQESNEKFCASKEFEGGVDANVILENACVAYKEAIDLPEENGTN

APMSLYNGCDSYGMKNPAVAQNPKNLPSKEDSVTEEKEIEESKSEYYTGVYEQQREDD

VTERGGLLLNAKADQMKNNLHSLCNQVPSMHGQTSPKKGKIVQSLSVPYGGARTKQPT

HLKLHIPKPLSEMLQSDLIPPNAGCSSKYKNDMLNKSNQGDNLISESLREDSAVRSPV

TDANGDFPGEYRGPGSLCLAVSPDSPDNDLLAGQFGVPISKPFTTLGEVAPVWVPDSQ

APNCMKCEARFTFTKRRHHCRACGKVFCAACCSLKCKLQYMDKKEARVCVICHSVLMN

AQAWENMLSASVQSPNPNNPAEYCSTIPPMQQAQASGALSSPPPTVMVPVGVLKHPGT

TABLE 6-continued

XSARA1 - Sequence ID NO:6

EGSQSKEQRRVWFADGILPNGETADSDNANVTTVAGTLTVSHTNNSTSSESENTSGFC

GSITQVGSAMNLIPEDGLPPILISTGVKGDYAVEERPSQMSVMQQLEEGGPDPLVFVL

NANLLAMVKIVNYVNRKCWCFTTKGMHAVGQAEIVILLQCLPDEKCLPRDLFSHFVEL

YQEAIAGNVVGNLGHSFLSQSFLGSKDHGGFLYVAPTYQSLQDLVLPAEPYLFGILIQ

KWETPWAKVFPIRLMLRLGAEYRLYPCPLFSVRYRKPLFGETGHTIINVLADFRNYQY

TLPVVQGLVVDMEVRKTSIKIPSNRYNEMMKAMNKSNEHVLAIGACFNQMADSHLVCV

QNDDGNYQTQAISIHKQPRKVTGASFFVFSGALKSSSGYLAKSSIVEDGVMVQITAES

MDALRQSLREMKDFTITCGKADAEESQEHVYVQWVEDDKNFNKGVFSPIDGKSMESVT

SVKIFHGSEYKASGKIIRWIEVFFLDNEEQQSGLSDPADHSRLTENVAKAFCLALCPH

LKLLKEDGMTRLGLRVSLDSDQVGYQAGSNGQLLPARYTNDLDGALVPVIHGGTCQLS

EGPVSMELIFYILENIS*

TABLE 7

XSARA2 - Sequence ID NO:7

AGTTTTATTTTCAGAAGACGTTGCATCTTTATTTTAAACATTAAGTTTCACTATGTAG

TAAAACATTACTGTTGTATATACAGTATGTTGTAGACATATAACGTAACTGTTTGCTT

TGTGCTTTCTTTCCTCCTCAGATGAAACTGTCTTTCCAAAGCTGTTAGATGCTAAGTG

GAATCAATTCTTAGAACCACATTCGCATAAAGTCACTGATAAACCAGCTCTTGACAAT

GTCTGTAAATCAATCATTGCTATTGAAGCTCATCTCAAAGTCAGGTCACCCAGCTTGA

CAGCCCTTGCAAGGTCCACATATGTGAATGGAGAAGTAGGTATTGTGACTCCTGAAAT

GCCTAAAATGGTGATAGGAGACACCGATATGGCAGAGGATTCACTTTTTAACACTGGT

CCCTCTGAAATTGTATGCAACTCTATTGTGGAGAGTCAAAGTTTAGAAGTTTTAGATG

ATGTACCAGTGAGTATTAACAATGAAAAAAGTGTTCTTCTTGATGATGGATTTTCTCC

GTACAGTAGCCCCAAAAGTGTTCTAAACTCTGCTTGCTTGACCATGAATAACGGAAAG

CCCTCACACGGTCAAAAAATTGTTAATGACCAAGATAAACAAGCTGTAACAATTTCAG

TCCTTCCAATGATCATACAGGATACTACTAACGTAAGCACAGACCCAGCTTTCAATAA

ATCTGGCACTGAAGAAGCTTATAGTGCATTAAAACAAACCACATCAGTTATTCTGCCT

GAAATAAAGCCTTATTCCATACAGGCTGCCCTTTCATGTGAAAATATCAACAAGATAC

CCAGATGTCAATTAAATAATACAGATCTACTCAGCATTTCACCAGTGGTTGAAGCATG

TAGTGAGAAGCAGCAAAATCATACAACTTCCTTGCATGAAAAAAAACTTGCAGCTGTG

TCTGCAACTGCGTTCTTTCCAGTCACTGCTGCTGAAACTGTACTAGGTAATGAAGCTC

TCCATAGTGCTGATTTTTTTGACATTGTTGTAAAGAACGTTTCTGACTCGTGTGTGTT

TAATGGTGACCTAACTAGAACTAATGGACTCTCACAAGAAAACAATGAAATGTTTTAT

GCAAGTAAAGAGTTGGAAGGAGGGGTAGATGCTAATATCTTATTGGAAGATGCATGCA

TAGCTTATAAAGAAAGAATAGATTTGTCTGAAGAAAATGGAACTAATGCACCAATGTA

TCTGTACAATGGGTGTGATTCCTATGGAATGAAAAACCCTGCTGTACGTCAAAACCCA

AAGAATTTACCATCAAAAGAAGATTCTGTGACAGAAGAAAAAGAAATTGAAGAAAGCA

AGTCAGAATACTATTCTGGTGTTTATGAACAACAGAAGGAAGATGACATAACTGAGAG

TABLE 7-continued

XSARA2 - Sequence ID NO:7

AGGTGGAGTCTTGTTAAATGCCAAGGTTGACCAAATGAAGAACAGTTTGCATAGTCTT
TATAATCCGGTTCCATCCATGCATGGGCAAACCTCACCAAAAAAGGGCAAGATTGTGC
AATCCCTCAGTGTTCCATATGGTGGAGCTCGCCCCAAGCAGCCAACTCATCTCAAACT
CAATATTCCACAGCCATTGTCTGAAATGTTACAGTGTGATCTCATTCCGCCAAATGCT
GGATGCAGCTCTAAAAACAAAAATGACATGTTAAACAAATCAAATCGGGGGATAACC
TGATTTCAGAATCACTACGTGAGGAAGTGCACAGCCCTGTTACTGATACAAATGGTGA
AGTCCCTCGAGAAAACAGGGGACCTGGCAGCCTGTGCCTTGCAGTGTCTCCAGACAGC
CCTGACAATGATCTGCTTGCTGGACAGTTTGGGGTACCCATCTCTAAGCCATTTACTA
CTCTAGGGGATGTGGCTCCAGTCTGGGTGCCAGATTCCCAAGCACCAAACTGCATGAA
GTGCGAGGCCAGATTTACATTTACCAAAAGGAGGCATCACTGCCGAGCTTGTGGAAAG
GTATGTAAAGAAATGTGGTGTTTCATCAGGGCAACAGTAATCACGGCAAATTATTCAT
AACAAAATGTGTTCAGCAGATTCAGTTAAAGTAGACTTATAAGTTACACAGTAACAAT
TCATCTGCTCAGCCTCATTTTGAAGTAGATAAAATATATTTTATTAGGAAACTCTGGG
GAGATATAAGGGAAAGCTTGCCTAAAAGTAGATGTTCTGTATATTATTTGGTAGTCAA
AGATGATTTCATGAAAAAAGGTTATTTGTAAAAAGTACAAAATGGGTAGAGACTAGAC
AATAAAAAGTAAGGAGTAAAAAACTAGGTATGTAACGTATATTAAAATAATTTTATGA
TTTTAATATTTACTGCACATTTTCTACAGTGCAGTGATTTGTATAACCATGCAATTAT
CAAATGCTTAGTGCCTTCACACAAAGTGCCTTTAATAAAAATTATTTTATAAATTATC
ATATTTTCTTTATATGTAGTCATCATCTTTTTTGTCTCATTTCTTGGAATCGTTCTAC
TTATGTTCTACTGATATGTTTTTTACCCGAGACCTATCTTGTCCTCTAAAGTAATTGG
CTTGTCAACTGGCTGTAGGGGATTTTCAGAGTTATAGCTTAGTACTGTTAATGAGCC
ATAGGTTGAAATAGTGCTCTAGATTTACATGTTGTACAACAGTTATTGCAATATGTGT
AGGGGGGGGG

TABLE 8

XSARA2 - Sequence ID NO:8

MPKMVIGDTDMAEDSLFNTGPSEIVCNSIVESQSLEVLDDVPVSINNEKSVLLDDGFS
PYSSPKSVLNSACLTMNNGKPSHGQKIVNDQDKEAVTISVLPMIIQDTTNVSTDPAFN
KSGTEEAYSALKQTTSVILPEIKPYSIQAALSCENINKIPRCQLNNTDLLSISPVVEA
CSEKQQNHTTSLHEKKLAAVSATAFFPVTAAETVLGNEALHSADFFDIVVKNVSDSCV
FNGDLTRTNGLSQENNEMFYASKELEGGVDANILLEDACIAYKERIDLSEENGTNAPM
YLYNGCDSYGMKNPAVRQNPKNLPSKEDSVTEEKEIEESKSEYYSGVYEQQKEDDITE
RGGVLLNAKVDQMKNSLHSLYNPVPSMHGQTSPKKGKIVQSLSVPYGGARPKQPTHLK
LNIPQPLSEMLQCDLIPPNAGCSSKNKNDMLNKSNRGDNLISESLREEVHSPVTDTNG
EVPRENRGPGSLCLAVSPDSPDNDLLAGQFGVPISKPFTTLGDVAPVWVPDSQAPNCM
KCEARFTFTKRRHHCRACGKVCKEMWCFIRATVITANYS

TABLE 9

```
hSARA    HWIDENAVAEDQLIKRNYSWDDQCSAVEMGEKKCGMLACLPDEKNVLVVAVMHHCDKRILQNDLQDCNNYNSQSLMD    77
XSARA    MPKHVIGDTIMAEDSLFNNIGPSEIVQNPSTMESQ---SLQALDDQS-----VNIHNEKSVILLADGFSPCSSP--KSIIN   70 hSARA    AFSCSLDNENRQTDQFSFSINESTEKDMNSEKQMDPLNRPKTEGRSVNHLCPTSSDSLASVCSPSQLKDDGSIGRDPSNS  157
XSARA    FDCLTMDN---------------EMPLHSQMSVDDNDK---ETVLISVLPTIIQDTSNVSIDDPAINKP----GTKEPHR  127 hSARA    AITSLTVDSVISSQGTDGCHAVKKGHN-YIPDEDLTGKISSPRTDLGSPNSFSHMSTGILMKKEPAEESTTEEESLRSGLP  236
XSARA    ALKETISVILPEIKPYSTCAALSFENNNKVPSYQLN------NTDLLS---YSPVYLACSPQQQKHTSSLHEEEKLFEGVS  198 hSARA    LLLKPDMPNGSGRNNDCERCSDCLVPNEVRADENEGYEHEETLGTTEFLNMTEHFSESQDMINWKLTKLNEMNDSQVNEE  316
XSARA    ATES---------------------FAATAAEDTVLDNEALRSAEFFDIVVKNFSDSCVINGDLTKSCGLS----DES   250 hSARA    KEKFLQISQPEDTNGDSGGQCVGLADAGLDLKGTCISESEECDFSTVIDTHAANYLSNGCDSYGMQDPGVSFVPKTLPSK  396
XSARA    NEKFCASKEPE------GG-----VDANVILENACVAYKEAIDLPEENGTNAPMSLYNGCDSYGMKNPAVAQNPKNLPSK  319 hSARA    EDSVTEEKEIEESKSECYSNIYEQ-RGNEATEGSGLLLNSTGDLMKKNYLHNFQSQVPSVLGQSSPKVVASLPSISVPFG  475
XSARA    EDSVTEEKEIEESKSEYYTGVYEQQREDDVTERGGLLLNAKADQMKNN--LHSLQNDVPSMHGOTSPKKGKIVQSLSVPYG  398 hSARA    GARPKQPSNLKLQIPKPLSDHLQND-FPANSGNNTKNKNDILGKAKLGENSATNVCSP-SLGNISNVDTNGEHLESVEAE  553
XSARA    GARTKQPTHLKLHIPKPLSEMLQSDLIEPNAGCSSKYKNDMLNKSNQGDNLISESLREDSAVRSPVTDANGDFPGEVRGP  478 primer 1 ——>
hSARA    ISTRPCLALAPDSPDNDLRAGQFGISAHKPFTTLGEVAPVWVPDSQAPNCMKCEARFTFTKRRHHCRACGKV FCASCCSL  633
XSARA    GS--LCLAVSPDSPDNSLLAGQFGVPISKPFTTLGEVAPVWVPDSQAPNCMKCEARFTFTKRRHHCRACGKV FCAACCSL  556

*
hSARA    KCKILYMDRKEARVCVICHSVLMNAQAWENMHSASSQSPNPNNPAEYCSTIPPLQQAQASGALSSPPPTVMVPVGVLKHP  713
XSARA    KCKLQYMDKKEARVCVICHSVLMNAQAWENMLSASVQSPNPNNPAEYCSTIPPMQQAQASGALSSPPPTVMVPVGVLKHP  636
                                            <—— primer 2 hSARA    GAEVAQPREQRRVWFADGILPNGEVADAAKLIMNGTSSAGTLAVSHDPVKPVTISPLPAETDIQLFSGSITQVGSPVGSA  793
XSARA    GTEGSQSKEQRRVWFADGILPNGETADSD--NANVTTVAGTLTVSHTNNSTSSES-----ENTSGFCGSITOVG----SA  705 hSARA    MNLIPEDGLPPILISTGVKGDYAVEEKPSQISVHQQLEDGGPDPLVFVLNANLLSMVKIVNYVNRKCWCFTTKGMHAVGQ  873
XSARA    MNLIPEDGLPPILISTGVKGDYAVEERPSOMSVHOOLEEGGPDPLVFVLNANLLSMVKIVNYVNRKCWCFTTKGMHAVGO  785 hSARA    SEIVILLQCLPDEKCLPKDIFNHFVQLYRDALAGNVVSNLGHSHFSQSFLGSKEHGGFLYVTSITYQSLQDLVLPTPPYLF  953
XSARA    AEIVILLQCLPDEKCLPRDLFSHFVELYQEAIAGNVVGNLGHSFLSQSFLGSKDHGGFLYVAPTYQSLQDLVLPAEPYLF  865 hSARA    GILIQKWETPWAKVFPIRLMLRLGAEYRLYPCPLFSVRFRKPLPGETGHTIMNLLADFRNYQYTLPVVQGLVVDMEVRKT  1033
XSARA    GILIOKWETPWAKVFPIRLMLRLGAEYRLYPCPLFSVRYRKPLPGETGHTIINVLADFRNYOYTLPVVOGLVVDMEVRKT   945 hSARA    SIKIPSNRYNEMHKAMNKSNEHVLAGGACFNEKADSHLVCVQNDDGNYQTQAISIHNQPRKVTGASFFVFSGALKSSSGY  1113
XSARA    SIKIPSNRYNEMHKAMNKSNEHVLATGACFNQHADSHLVCVQNDDGNYQTQAISIHRQPRKVTGASFFVFSGALKSSSGY  1025 hSARA    LAKSSIVEDGVHVQITAENMDSLRQALREMKDFTITCGKADAEEPQEHIHIQWVDDDKNVSKGVVSPIDGKSMETITNVK  1193
XSARA    LAKSSIVEDGVHVOITAESMDALROSLREMKDFTITCGKADAEESOEHVYVOWVEDDKNFNKGVFSPIDGKSMESVTSVK  1105 hSARA    IFHGSEYKANGKVIRWTEVFFLENDDQHNCLSDPADHSRLTEHVAKAFCLALCPHLKLLKEDGNTKLGLRVT LDSDQVGY  1273
XSARA    IFHGSEYKASGKIIRWTEVFFLENEEQQSGLSDPADHSRLTENVAKAFCLALCPHLKLLKEDGMTRLGLRVS LDSDQVGY  1185 hSARA    QAGSNGQFLPSQYMNDLDSALVPVIHGGACQLSEGPVVMELIFYILENIV-  1323
XSARA    QAGSNGQLLPARYTNDLDGALVPVIHGGTCQLSEGPVSMELIFYILENIS-  1235
```

TABLE 10

```
hSARA      587   LGEVAPVWVFDSQAPNCMKCEARF-TFTKRRHHCRACGKVFQASCCSLKCKILYADKK-EARVCVICHSVL   655
XSARA      510   LGEVAPVWVPDSQAPNCMKCEARF-TFTKRRHHCRACGKVFQAACCSLKCKLCYADKK-EARVCVICHSVL   578
KIAA0305   737   LGQKQPIWVPDSEAPNCMNCQMKF-NSTTKRRHHCKACGHVVCGKCSEFRARIVMYDNNR-SNRVCTDCYVAL  800
FGD1       720   LGKRAPTPIREKEVTMCMRCQEPFNSTTKRRHHCKACGHVVCGKCSEFRARIVMYDNNR-SNRVCTDCYVAL  485
Hrs        153   AAERAPQWVD---AEECHRCRVQF-GVVTRKHHCRACGQIFCGKCSSKYSTIPKFGIEKEMRVCEPCYEQL   219
Hrs-2      153   AAERAPQWVD---AEECHRCRVQF-GVVTRKHHCRACGQIFCGKCSSKYSTIPKFGIEKEMRVCEPCYEQL   219
EEA-1     1341   TOALNRKWAEDNEVQNCMALGKGF-SVTVRRHHCRCCGNIFCAECSAKNALTPSSKK--PVRVQDACFNDL  1408

CONSENSUS        -----P-W-------C--C---F-----R/K HHCRACG-Y/I FC G/A C C/S ---------------RVC--C---L
```

I claim:

1. An isolated polynucleotide comprising a nucleotide sequence encoding a SARA protein, wherein the nucleotide sequence is selected from the group consisting of
   (a) a nucleotide sequence encoding the amino acid sequence of Sequence ID NO:2; and
   (b) a nucleotide sequence encoding the amino acid sequence of Sequence ID NO:4.

2. The isolated polynucleotide of claim 1 comprising the nucleotide sequence of Sequence ID NO:1 or a degeneracy equivalent thereof.

3. The isolated polynucleotide of claim 1 comprising the nucleotide sequence of Sequence ID NO:3 or a degeneracy equivalent thereof.

4. The isolated polynucleotide of claim 1 wherein the polynucleotide is a polydeoxyribonucleotide.

5. The isolated polynucleotide of claim 1 wherein the polynucleotide is a polyribonucleotide.

6. A recombinant vector comprising the isolated polynucleotide of claim 1.

7. A host cell comprising the recombinant vector of claim 6.

8. A process for recombinantly producing a SARA protein or a fragment thereof comprising culturing the host cell of claim 7 under conditions whereby the SARA protein or fragment thereof is expressed and isolating the expressed SARA protein or fragment thereof.

9. An isolated SARA protein comprising the amino acid sequence of Sequence ID NO:2 or Sequence ID NO:4.

* * * * *